(12) United States Patent
Hahn et al.

(10) Patent No.: US 11,377,417 B2
(45) Date of Patent: Jul. 5, 2022

(54) BRANCHED 3-PHENYLPROPIONIC ACID DERIVATIVES AND THEIR USE

(71) Applicant: Bayer Intellectual Property GmbH, Monheim (DE)

(72) Inventors: Michael Hahn, Langenfeld (DE); Thomas Lampe, Duesseldorf (DE); Johannes-Peter Stasch, Solingen (DE); Karl-Heinz Schlemmer, Wuppertal (DE); Frank Wunder, Wuppertal (DE); Volkhart Min-Jian Li, Velbert (DE); Eva Maria Becker-Pelster, Wuppertal (DE); Friederike Stoll, Duesseldorf (DE); Andreas Knorr, Erkrath (DE); Elisabeth Woltering, Hilden (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 16/904,786

(22) Filed: Jun. 18, 2020

(65) Prior Publication Data

US 2020/0385335 A1 Dec. 10, 2020

Related U.S. Application Data

(60) Continuation of application No. 16/230,957, filed on Dec. 21, 2018, now abandoned, which is a continuation of application No. 16/001,146, filed on Jun. 6, 2018, now Pat. No. 10,259,776, which is a continuation of application No. 15/158,331, filed on May 18, 2016, now Pat. No. 10,023,528, which is a division of application No. 14/304,171, filed on Jun. 13, 2014, now abandoned, which is a continuation of application No. 13/431,934, filed on Mar. 27, 2012, now Pat. No. 8,796,335.

(30) Foreign Application Priority Data

Apr. 13, 2011 (DE) .......................... 102011007272.1

(51) Int. Cl.
| | | |
|---|---|---|
| C07C 231/14 | (2006.01) |
| A61K 45/06 | (2006.01) |
| C07C 235/38 | (2006.01) |
| C07C 233/55 | (2006.01) |
| A61K 31/196 | (2006.01) |
| A61K 9/00 | (2006.01) |

(52) U.S. Cl.
CPC .......... *C07C 231/14* (2013.01); *A61K 9/0053* (2013.01); *A61K 31/196* (2013.01); *A61K 45/06* (2013.01); *C07C 233/55* (2013.01); *C07C 235/38* (2013.01); *C07C 2601/02* (2017.05); *C07C 2601/04* (2017.05); *C07C 2601/08* (2017.05)

(58) Field of Classification Search
None
See application file for complete search history.

(56) References Cited

U.S. PATENT DOCUMENTS

| | | | |
|---|---|---|---|
| 3,916,899 A | 11/1975 | Theeuwes et al. |
| 4,063,064 A | 12/1977 | Saunders et al. |
| 4,088,864 A | 5/1978 | Theeuwes et al. |
| 4,111,202 A | 9/1978 | Theeuwes |
| 4,327,725 A | 5/1982 | Cortese et al. |
| 4,765,989 A | 8/1988 | Wong et al. |
| 5,041,453 A | 8/1991 | Huang et al. |
| 5,648,368 A | 7/1997 | Egbertson et al. |
| 5,693,650 A | 12/1997 | Muller et al. |
| 5,811,429 A | 9/1998 | Connell et al. |
| 5,935,984 A | 8/1999 | Goldmann et al. |
| 6,667,334 B1 | 12/2003 | Neises et al. |
| 6,693,102 B2 | 2/2004 | Stasch et al. |
| 6,743,798 B1 | 6/2004 | Straub et al. |
| 6,833,364 B1 | 12/2004 | Straub et al. |
| 6,835,752 B2 | 12/2004 | Tani et al. |
| 6,884,821 B1 | 4/2005 | Shinoda et al. |
| 7,005,440 B1 | 2/2006 | Jayyosi et al. |
| 7,166,616 B2 | 1/2007 | Harris |
| 7,173,037 B2 | 2/2007 | Alonso-Alija et al. |
| 7,176,204 B2 | 2/2007 | Miyachi et al. |
| 7,238,716 B2 | 7/2007 | Momose et al. |
| 7,241,785 B2 | 7/2007 | Momose et al. |
| 7,244,861 B2 | 7/2007 | Matsuura et al. |
| 7,368,578 B2 | 5/2008 | Momose et al. |
| 7,371,777 B2 | 5/2008 | Clark et al. |
| 7,425,649 B2 | 9/2008 | Kuo et al. |
| 7,465,825 B2 | 12/2008 | Van Zandt et al. |
| 7,491,748 B2 | 2/2009 | Tani et al. |
| 7,674,825 B2 | 3/2010 | Alonso-Alija et al. |

(Continued)

FOREIGN PATENT DOCUMENTS

| | | |
|---|---|---|
| CA | 2129374 A1 | 2/1995 |
| CN | 101056850 A | 10/2007 |

(Continued)

OTHER PUBLICATIONS

Schafer, S. et al., "Failure is an Option: Learning from Unsuccessful Proof-of-Concept Trials," Drug Discovery Today, Nov. 2008, 13, 913-916.

Horig, H. et al., "From Bench to Clinic and Back: Perspective on the 1st IQPC Translational Research Conference," Journal of Translational Medicine, Dec. 2004, 2, 44.

(Continued)

*Primary Examiner* — Po-Chih Chen
(74) *Attorney, Agent, or Firm* — Quarles & Brady LLP

(57) ABSTRACT

The present application relates to novel 3-phenylpropionic acid derivatives which carry a branched or cyclic alkyl substituent in the 3-position, to processes for their preparation, to their use for the treatment and/or prevention of diseases and to their use for preparing medicaments for the treatment and/or prevention of diseases, in particular for the treatment and/or prevention of cardiovascular diseases.

6 Claims, No Drawings

(56) References Cited

U.S. PATENT DOCUMENTS

| | | | |
|---|---|---|---|
| 7,816,367 | B2 | 10/2010 | Akerman et al. |
| 7,998,988 | B2 | 8/2011 | Bartel et al. |
| 8,097,610 | B2 | 1/2012 | Itai |
| 8,796,335 | B2 | 8/2014 | Hahn |
| 8,802,686 | B2 | 8/2014 | Lucking et al. |
| 8,981,104 | B2 | 3/2015 | Hahn et al. |
| 9,018,258 | B2 | 4/2015 | Lampe et al. |
| 9,018,414 | B2 | 4/2015 | Lampe et al. |
| 10,905,667 | B2 | 2/2021 | Stroyer et al. |
| 2003/0105097 | A1 | 6/2003 | Simon et al. |
| 2003/0161882 | A1 | 8/2003 | Waterman |
| 2005/0187266 | A1 | 8/2005 | Su |
| 2005/0234066 | A1 | 10/2005 | Bailey et al. |
| 2006/0167044 | A1 | 7/2006 | Damiano |
| 2007/0026065 | A1 | 2/2007 | Benke et al. |
| 2011/0034450 | A1 | 2/2011 | Hahn et al. |
| 2011/0092554 | A1 | 4/2011 | Chesworth et al. |
| 2011/0130445 | A1 | 6/2011 | Lampe et al. |
| 2012/0028971 | A1 | 2/2012 | Lampe et al. |
| 2012/0172448 | A1 | 7/2012 | Lampe et al. |
| 2013/0079412 | A1 | 3/2013 | Hahn et al. |
| 2014/0142069 | A1 | 5/2014 | Lampe et al. |
| 2014/0309307 | A1 | 10/2014 | Hahn et al. |
| 2015/0152050 | A1 | 6/2015 | Lampe et al. |
| 2019/0224176 | A1 | 7/2019 | Kolkhof et al. |
| 2020/0237648 | A1 | 7/2020 | Stroyer et al. |
| 2021/0113504 | A1 | 4/2021 | Stroyer et al. |

FOREIGN PATENT DOCUMENTS

| | | |
|---|---|---|
| CN | 101116660 A | 2/2008 |
| DE | 3417113 C2 | 2/1989 |
| EP | 0277092 B1 | 8/1988 |
| EP | 0608709 A1 | 8/1994 |
| EP | 0783299 A1 | 7/1997 |
| EP | 1024793 | 8/2000 |
| EP | 1229010 A1 | 8/2002 |
| EP | 1285908 A1 | 2/2003 |
| EP | 2179992 A1 | 4/2010 |
| EP | 2179993 A1 | 4/2010 |
| WO | 961190 A1 | 4/1996 |
| WO | 96/12473 A1 | 5/1996 |
| WO | 96/30036 A1 | 10/1996 |
| WO | 00/6568 A1 | 2/2000 |
| WO | 00/06569 A1 | 2/2000 |
| WO | 0050398 A2 | 8/2000 |
| WO | 00/64888 A1 | 11/2000 |
| WO | 0100183 A2 | 1/2001 |
| WO | 0224633 A1 | 3/2002 |
| WO | 02/42301 A1 | 5/2002 |
| WO | 03/095451 A1 | 11/2003 |
| WO | 2004/099170 A2 | 11/2004 |
| WO | 2006/050097 A1 | 5/2006 |
| WO | 2006055625 A2 | 5/2006 |
| WO | 2006/072367 A1 | 7/2006 |
| WO | 2006077217 A1 | 7/2006 |
| WO | 2009127338 A1 | 10/2009 |
| WO | 2009156484 A2 | 12/2009 |
| WO | 2010/060564 A1 | 6/2010 |
| WO | 2011/147809 A1 | 12/2011 |
| WO | 2012/004258 | 1/2012 |
| WO | 2012/028647 A1 | 3/2012 |
| WO | 2012/059549 A1 | 5/2012 |
| WO | 2012076466 A2 | 6/2012 |
| WO | 2012/139888 A1 | 10/2018 |
| WO | 2019105881 A1 | 6/2019 |
| WO | 2020020790 A1 | 1/2020 |
| WO | 2020245342 A1 | 12/2020 |

OTHER PUBLICATIONS

Nossaman et al., "Stimulators and Activators of Soluble Guanylate Cyclase: Review and Potential Therapeutics Indications," Critical Care Research and Practice, 2012, pp. 1-12.

Egenov et al., "NO-Independent Stimulators and Activators of Soluble Guanylate Cyclase: Discovery and Therapeutic Potential," Nature Reviews Drug Discovery, Sep. 2006, vol. 5, No. 9, pp. 755-768.

Hayashi, "Rhodium-Catalyzed Asymmetric 1,4-Addition of Organoboronic Acids and Their Derivatives to Electron Deficient Olefins," Synlett, 2002, No. SI, pp. 879-887.

Mase et al., "Synthesis of a Musarnic Receptor Antagonist via a Diastereoselective Michael Reaction, Selective Deoxyfluorination and Aromatic Metal-Halogen Exchange Reaction," The Journal of Organic Chemistry, Sep. 7, 2001, vol. 66, No. 20, pp. 6775-6786.

Moradi et al., "Palladium-Catalyzed α-Arylation of Esters," Journal of the American Chemical Society, Jul. 27, 2001, vol. 123, No. 33, pp. 7996-8002.

Saki et al., "Rhodium-Catalyzed Conjugate Addition of Aryl- or 1-Alkenylboronic Acids to Enones," Organometallics, Sep. 30, 1997, vol. 16, No. 20, pp. 4229-4231.

Schmidt et al., "NO-and Haem-Independent Soluble Guanylate Cyclase Activators," Handbook of Experimental Pharmacology, Springer Verlag (publisher), Berlin and Heidelberg Germany, 2009, vol. 191, pp. 309-339.

Stasch et al., "NO- and Haem-Independent Activation of Soluble Guanylyl Cyclase: Molecular Basis and Cardiovascular Implications of a New Pharmacological Principle," British Journal of Pharmacology, Jul. 2002, vol. 136, No. 5, pp. 773-783.

Stasch et al., "Targeting the Heme-Oxidized Nitric Oxide Receptor for Selective Vasodilatation of Diseased Blood Vessels," The Journal of Clinical Investigation, Sep. 2006, vol. 116, No. 9, pp. 2552-2561.

Varchi et al., "Copper Catalyzed Conjugate Addition of Highly Functionalized Arylmagnesium Compounds to Enones," Tetrahedron, Apr. 28, 2000, vol. 56, Issue 18, pp. 2727-2731.

Weintraub et al., "Syntheses of Steroidal Vinyl Ethers Using Palladium Acetate-Phenanthroline as Catalyst," Journal of Organic Chemistry, 1997, vol. 62, No. 5, pp. 1560-1562.

Wolfe et al., "Palladium-Catalyzed Amination of Aryl Halidesand Aryl Tritiates: N-Hexyl-2-Methyl-4-Methoxyaniline and N-Methyl-N-(4-Chlorophenyl) Aniline," Organic Syntheses, Coll. 2004, vol. 10, pp. 423; 2002, vol. 78, pp. 23, 8 pages.

Demko et al., "Preparation of 5-Substituted 1H-Tetrazoles from Nitrites in Water," Journal of Organic Chemistry, Nov. 3, 2001, vol. 66, No. 24, pp. 7945-7950.

Patani et al., "Bioisosterism: A Rational Approach in Drug Design," Chemical Reviews, 1996, vol. 96, No. 8, pp. 3147-3176.

Stasch et al., "Renal Effects of Soluble Guanylate Cyclase Stimulators and Activators: A Review of the Preclinical Evidence," Current Opinion in Pharmacology, 2015, 21, pp. 95-104.

Sandner et al., "The Potential of sGC Modulators for the Treatment of Age-Related Fibrosis: A Mini-Review," Gerontology, 2017, 63, pp. 216-227.

Gheorghiade et al., "Soluble Guanylate Cyclase: Potential Therapeutic Target for Heart Failure," Heart Fail Rev, 2013, 18, pp. 123-134.

Sandner et al., "Anti-Fibrotic Effects of Soluble Guanylate Cyclase Stimulators and Activators: A Review of the Preclinical Evidence," Respiratory Medicine, 2017, 122, pp. S1-S9.

Breitenstein et al., "Novel sGC Stimulators and sGC Activators for the Treatment of Heart Failure," Heart Failure Handbook of Experimental Pharmacology, 2016, pp. 225-241.

Stasch et al., "Soluble Guanylate Cyclase as an Emerging Therapeutic Target in Cardiopulmonary Disease," Circulation, May 21, 2011, pp. 2263-2273.

FDA World Health Organization, "FDA Approves Bayer's New Class of Drug ADEMPAS (Riociguat) Tablets to Treat Adults with PAH and Persistent, Recurrent or Inoperable CTEPH," CISION PR Newswire, Oct. 8, 2013, 18:54 ET, 8 pages.

Krieg et al., "BAY 58-2667, A Nitric Oxide-Independent Guanylyl Cyclase Activator, Pharmacologically Post-Conditions Rabbit and Rat Hearts," 2009, European Heart Journal, 30, pp. 1607-1613.

Evgenov, Oleg V. et al., "Inhaled Agonists of Soluble Guanylate Cyclase Induce Selective Pulmonary Vasodilation," American Journal of Respiratory and Critical Care Medicine, vol. 176, 2007, pp. 1138-1145.

(56) References Cited

OTHER PUBLICATIONS

Rashmi Sareen et al., "An Insight to Osmotic Drug Discovery," Current Drug Discovery, Bd. 9, Nr. 3, 1, Apr. 2012 (Apr. 1, 2012), Seiten 285-296.

Montani et al., "Updated Clinical Classification of Pulmonary Hypertension," Pulmonary Circulation: Diseases and their Treatment, 2011, Third Edition, pp. 197-206, Hodder Arnold, United Kingdom.

Verma et al., "Osmotically Controlled Oral Drug Delivery," Drug Development and Industrial Pharmacy, 2000; 26:695-708.

Malaterre et al., "Oral Osmotically Driven Systems: 30 Years of Development and Clinical Use," European Journal of Pharmaceutics and Biopharmaceutics, 2009; 73:311-323.

Hoeper et al., "Diagnosis, Assessment, and Treatment of Non-Pulmonary Arterial Hypertension Pulmonary Hypertension," J. Am. Coll. Cardiol., 2009; 54 (1): 85-96.

Kumar et al., "An Overview of Recent Patents on Oral Osmotic Drug Delivery Systems," Recent Patents on Drug Delivery & Formulation, 2007; 1:236-255.

Kaushal et al., "An Update on Osmotic Drug Delivery Patents," Pharmaceutical Technology, 2003; 13(1):8-97.

Verma et al., "Formulation Aspects in the Development of Osmotically Controlled Oral Drug Delivery Systems," Journal of Controlled Release, 2002; 79:7-27.

BRANCHED 3-PHENYLPROPIONIC ACID DERIVATIVES AND THEIR USE

This application is a continuation of U.S. application Ser. No. 16/230,957 filed on Dec. 21, 2018, the content of which is incorporated herein by reference in its entirety, which is a continuation of U.S. application Ser. No. 16/001,146, filed on Jun. 6, 2018, now U.S. Pat. No. 10,259,776, which is a continuation U.S. application Ser. No. 15/158,331, filed on May 18, 2016, now U.S. Pat. No. 10,023,528, which is a divisional of U.S. application Ser. No. 14/304,171, filed on Jun. 13, 2014, which is a continuation of U.S. application Ser. No. 13/431,934 filed on Mar. 27, 2012, now U.S. Pat. No. 8,796,335, which claims priority to German Application No. 102011007272.1, filed Apr. 13, 2011.

The present application relates to novel 3-phenylpropionic acid derivatives which carry a branched or cyclic alkyl substituent in the 3-position, to processes for their preparation, to their use for the treatment and/or prevention of diseases and to their use for preparing medicaments for the treatment and/or prevention of diseases, in particular for the treatment and/or prevention of cardiovascular diseases.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment [O. V. Evgenov et al., Nature Rev. Drug Disc. 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO-independent and selective activation of the haem-containing sGC. In addition, the sGC stimulators in combination with NO have a synergistic effect on sGC activation based on a stabilization of the nitrosyl-haem complex. The exact binding site of the sGC stimulators at the sGC is still being debated. If the haem group is removed from the soluble guanylate cyclase, the enzyme still has a detectable catalytic basal activity, i.e. cGMP is still being formed. The remaining catalytic basal activity of the haem-free enzyme cannot be stimulated by any of the stimulators mentioned above [Evgenov et al., ibid.].

In addition, NO- and haem-independent sGC activators, with BAY 58-2667 as prototype of this class, have been identified. Common characteristics of these substances are that in combination with NO they only have an additive effect on enzyme activation, and that the activation of the oxidized or haem-free enzyme is markedly higher than that of the haem-containing enzyme [Evgenov et al., ibid.; J. P. Stasch et al., Br. J. Pharmacol. 136 (2002), 773; J. P. Stasch et al., J. Clin. Invest. 116 (2006), 2552]. Spectroscopic studies show that BAY 58-2667 displaces the oxidized haem group which, as a result of the weakening of the iron-histidine bond, is attached only weakly to the sGC. It has also been shown that the characteristic sGC haem binding motif Tyr-x-Ser-x-Arg is absolutely essential both for the interaction of the negatively charged propionic acids of the haem group and for the action of BAY 58-2667. Against this background, it is assumed that the binding site of BAY 58-2667 at the sGC is identical to the binding site of the haem group [J. P. Stasch et al., J. Clin. Invest. 116 (2006), 2552].

The compounds described in the present invention are now likewise capable of activating the haem-free form of soluble guanylate cyclase. This is also confirmed by the fact that these novel activators firstly have no synergistic action with NO at the haem-containing enzyme and that secondly their action cannot be blocked by the haem-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., Nature Rev. Drug Disc. 5 (2006), 755; J. P. Stasch et al., J. Clin. Invest. 116 (2006), 2552].

It was thus an object of the present invention to provide novel compounds which act as activators of soluble guanylate cyclase in the manner described above and can be used as such in particular for the treatment and prevention of cardiovascular disorders.

WO 00/64888-A1, EP 1 216 980-A1, EP 1 285 908-A1, EP 1 348 698-A1, EP 1 375 472-A1, EP 1 452 521-A1, US 2005/0187266-A1 and US 2005/0234066-A1 describe various arylalkanecarboxylic acid derivatives as PPAR agonists for treating diabetes, dyslipidaemia, arteriosclerosis, obesity and other disorders. EP 1 312 601-A1 and EP 1 431 267-A1 disclose substituted arylalkanecarboxylic acids as $PGE_2$ receptor antagonists for the treatment, for example, of states of pain, urological disorders, Alzheimer's disease and cancer. Furthermore, WO 2005/086661-A2 claims arylalkanecarboxylic acids as GPR40 modulators for the treatment of diabetes and dyslipidaemias, and WO 2004/099170-A2, WO 2006/050097-A1 and WO 2006/055625-A2 describe phenyl-substituted carboxylic acids as PTP-1B inhibitors for the treatment of diabetes, cancer and neurodegenerative disorders. Furthermore, individual phenylacetamido-substituted phenylalkanecarboxylic acids which, in the form of non-covalent mixtures improve the delivery of active peptide compounds within the body are known from WO 96/12473-A1 and WO 96/30036-A1. WO 2009/067493-A2 claims 3,5-disubstituted phenylacetic acid derivatives for the treatment of Alzheimer's disease. WO 2009/127338-A1 and WO 2010/102717-A1 disclose oxoheterocyclically substituted carboxylic acid derivatives which act as activators of soluble guanylate cyclase.

The present invention provides compounds of the general formula (I)

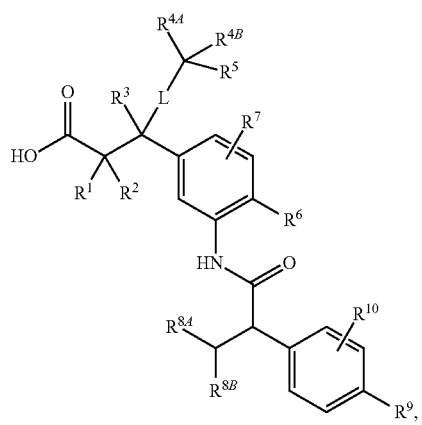

in which
$R^1$, $R^2$ and $R^3$ independently of one another represent hydrogen or methyl,
L represents a bond or represents —$CH_2$—,
$R^{4A}$ and $R^{4B}$ independently of one another represent methyl, trifluoromethyl or ethyl
or
$R^{4A}$ and $R^{4B}$ are attached to one another and together with the carbon atom to which they are attached form a cyclopropyl or cyclobutyl ring which may be substituted up to two times by fluorine,
$R^5$ represents hydrogen, fluorine, methyl or methoxy,
$R^6$ represents hydrogen, fluorine, chlorine, bromine, cyano, methyl, trifluoromethyl, ethyl, methoxy or trifluoromethoxy,
$R^7$ represents hydrogen, fluorine, chlorine or methyl,
$R^{8A}$ represents methyl or ethyl,
$R^{8B}$ represents trifluoromethyl,
or
$R^{8A}$ and $R^{8B}$ are attached to one another and together with the carbon atom to which they are attached form an optionally difluoro-substituted cyclopentyl ring of the formula

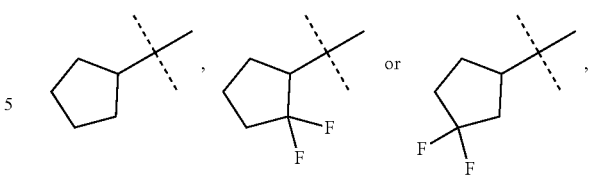

$R^9$ represents fluorine, chlorine, bromine, cyano, ($C_1$-$C_4$)-alkyl, ($C_2$-$C_4$)-alkenyl, cyclopropyl or cyclobutyl, where ($C_1$-$C_4$)-alkyl and ($C_2$-$C_4$)-alkenyl may be substituted up to three times by fluorine
and
cyclopropyl and cyclobutyl may be substituted up to two times by fluorine,
and
$R^{10}$ represents hydrogen, fluorine, chlorine, methyl, trifluoromethyl, ethyl or methoxy,
and salts, solvates and solvates of the salts thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Preferred salts in the context of the present invention are physiologically acceptable salts of the compounds according to the invention. Salts which are not themselves suitable for pharmaceutical uses but can be used, for example, for isolation, purification or storage of the compounds according to the invention are also included.

Physiologically acceptable salts of the compounds according to the invention include in particular salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylpiperidine, N-methylmorpholine, arginine, lysine and 1,2-ethylenediamine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers or diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

As prodrugs, the present invention comprises in particular hydrolysable ester derivatives of the carboxylic acids of the formula (I) according to the invention. These are to be understood as meaning esters which can be hydrolysed to the free carboxylic acids, as the compounds that are mainly active biologically, in physiological media, under the conditions of the biological tests described later and in particular in vivo by enzymatic or chemical routes. ($C_1$-$C_4$)-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

($C_1$-$C_4$)-Alkyl in the context of the invention represents a straight-chain or branched alkyl radical having 1 to 4 carbon atoms. The following may be mentioned by way of example and by way of preference: methyl, ethyl, n-propyl, isopropyl, n-butyl, isobutyl, sec-butyl and tert-butyl.

($C_1$-$C_4$)-Alkenyl and ($C_2$-$C_3$)-alkenyl in the context of the invention represent a straight-chain or branched alkenyl radical having a double bond and 2 to 4 and 2 or 3 carbon atoms, respectively. A straight-chain or branched alkenyl radical having 2 or 3 carbon atoms is preferred. The following may be mentioned by way of example and by way of preference: vinyl, allyl, n-prop-1-en-1-yl, iso-propenyl, n-but-1-en-1-yl, n-but-2-en-1-yl, n-but-3-en-1-yl, 2-methyl-prop-1-en-1-yl and 2-methyl-prop-2-en-1-yl.

In the context of the present invention, all radicals which occur more than once are defined independently of one another. If radicals in the compounds according to the invention are substituted, the radicals may be mono- or polysubstituted, unless specified otherwise. Substitution by one, two or three identical or different substituents is preferred. Particular preference is given to substitution by one or two identical or different substituents.

In the context of the present invention, preference is given to compounds of the formula (I) in which
$R^1$ represents hydrogen or methyl,
$R^2$ represents hydrogen,
$R^3$ represents hydrogen or methyl,
L represents a bond or represents —$CH_2$—,
$R^{4A}$ and $R^{4B}$ both represent methyl or are attached to one another and together with the carbon atom to which they are attached form a cyclopropyl or cyclobutyl ring which may be substituted up to two times by fluorine,
$R^5$ represents hydrogen, fluorine, methyl or methoxy,
$R^6$ represents fluorine, chlorine, methyl or ethyl,
$R^7$ represents hydrogen or fluorine,
$R^{8A}$ represents methyl,
$R^{8B}$ represents trifluoromethyl,
or
$R^{8A}$ and $R^{8B}$ are attached to one another and together with the carbon atom to which they are attached form a difluoro-substituted cyclopentyl ring of the formula

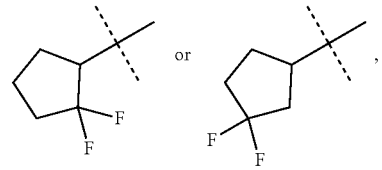

$R^9$ represents fluorine, chlorine, ($C_1$-$C_4$)-alkyl, ($C_2$-$C_3$)-alkenyl, cyclopropyl or cyclobutyl, where
  ($C_1$-$C_4$)-alkyl and ($C_2$-$C_3$)-alkenyl may be substituted up to three times by fluorine
  and
  cyclopropyl and cyclobutyl may be substituted up to two times by fluorine,
and
$R^{10}$ represents hydrogen, fluorine, chlorine, methyl or methoxy,
and salts, solvates and solvates of the salts thereof.

A particular embodiment of the present invention comprises compounds of the formula (I) in which
$R^1$ and $R^2$ both represent hydrogen,
and salts, solvates and solvates of the salts thereof.

A further particular embodiment of the present invention comprises compounds of the formula (I) in which
$R^3$ represents hydrogen or methyl
and
L represents a bond,
and salts, solvates and solvates of the salts thereof.

A further particular embodiment of the present invention comprises compounds of the formula (I) in which
$R^3$ represents hydrogen
and
L represents —CH$_2$—,
and salts, solvates and solvates of the salts thereof.

A further particular embodiment of the present invention comprises compounds of the formula (I) in which
$R^{4A}$ and $R^{4B}$ both represent methyl
and
$R^5$ represents hydrogen,
and salts, solvates and solvates of the salts thereof.

A further particular embodiment of the present invention comprises compounds of the formula (I) in which
$R^{4A}$ and $R^{4B}$ are attached to one another and together with the carbon to which they are attached form a cyclopropyl or cyclobutyl ring which may be substituted up to two times by fluorine,
and
$R^5$ represents hydrogen, fluorine or methyl,
and salts, solvates and solvates of the salts thereof.

A further particular embodiment of the present invention comprises compounds of the formula (I) in which
$R^6$ represents chlorine
and
$R^7$ represents hydrogen,
and salts, solvates and solvates of the salts thereof.

A further particular embodiment of the present invention comprises compounds of the formula (I) in which
$R^{8A}$ represents methyl
and
$R^{8B}$ represents trifluoromethyl,
and salts, solvates and solvates of the salts thereof.

A further particular embodiment of the present invention comprises compounds of the formula (I) in which
$R^{8A}$ and $R^{8B}$ are attached to one another and together with the carbon atom to which they are attached form a difluoro-substituted cyclopentyl ring of the formula

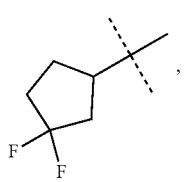

and salts, solvates and solvates of the salts thereof.

A further particular embodiment of the present invention comprises compounds of the formula (I) in which
$R^9$ represents fluorine, chlorine, (C$_1$-C$_4$)-alkyl or cyclopropyl, where (C$_1$-C$_4$)-alkyl may be substituted up to three times by fluorine and cyclopropyl may be substituted up to two times by fluorine,
and salts, solvates and solvates of the salts thereof.

A further particular embodiment of the present invention comprises compounds of the formula (I) in which
$R^{10}$ represents hydrogen, fluorine, chlorine, methyl or methoxy,
and salts, solvates and solvates of the salts thereof.

Particular preference in the context of the present invention is given to compounds of the formula (I) in which
$R^1$ and $R^2$ both represent hydrogen,
$R^3$ represents hydrogen or methyl,
L represents a bond or represents —CH$_2$—, $R^{4A}$ and $R^{4B}$ both represent methyl or are attached to one another and together with the carbon atom to which they are attached form a cyclopropyl or cyclobutyl ring which may be substituted up to two times by fluorine,
$R^5$ represents hydrogen, fluorine or methyl,
$R^6$ represents chlorine,
$R^7$ represents hydrogen,
$R^{8A}$ represents methyl,
$R^{8B}$ represents trifluoromethyl,
$R^9$ represents fluorine, chlorine, methyl, trifluoromethyl, ethyl, 2,2,2-trifluoroethyl, isopropyl, tert-butyl, cyclopropyl or 2,2-difluorocyclopropyl, and
$R^{10}$ represents hydrogen, fluorine, methyl or methoxy,
and salts, solvates and solvates of the salts thereof.

Of particular importance in the context of the present invention are compounds of the formula (I-A)

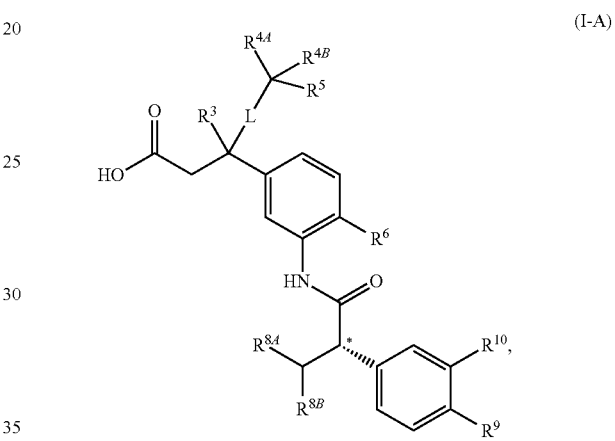

in which the carbon atom marked* of the phenylacetamide grouping has the S-configuration shown
and
the radicals $R^3$, $R^{4A}$, $R^{4B}$, $R^5$, $R^6$, $R^{8A}$, $R^{8B}$, $R^9$ and $R^{10}$ and L each have the meanings given above,
and salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations. Combinations of two or more of the abovementioned preferred ranges are very particularly preferred.

The invention furthermore provides a process for preparing the compounds of the formula (I) according to the invention, characterized in that a carboxylic acid of the formula (II)

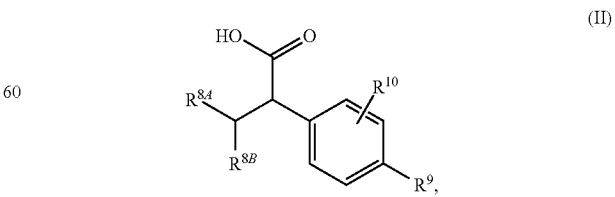

in which $R^{8A}$, $R^{8B}$, $R^9$ and $R^{10}$ have the meanings given above, is coupled in an inert solvent with the aid of a condensing agent or via the intermediate of the corresponding carbonyl chloride in the presence of a base with an amine of the formula (III)

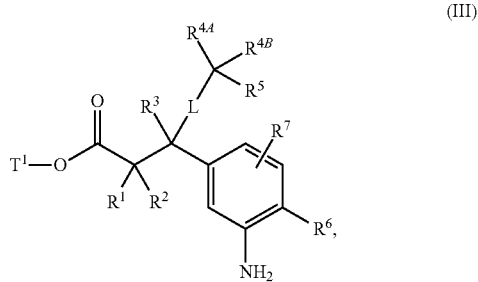

(III)

in which L, $R^1$, $R^2$, $R^3$, $R^{4A}$, $R^{4B}$, $R^5$, $R^6$ and $R^7$ have the meanings given above
and
$T^1$ represents $(C_1-C_4)$-alkyl or benzyl,
to give a carboxamide of the formula (IV)

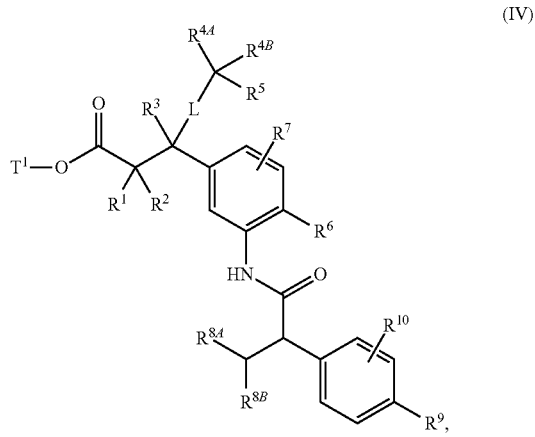

(IV)

in which L, $R^1$, $R^2$, $R^3$, $R^{4A}$, $R^{4B}$, $R^5$, $R^6$, $R^7$, $R^{8A}$, $R^{8B}$, $R^9$, $R^{10}$ and $T^1$ have the meanings given above,
and the ester radical $T^1$ is then removed by basic or acidic solvolysis or, in the case that $T^1$ represents benzyl, also by hydrogenolysis to give the carboxylic acid of the formula (I) and the compounds of the formula (I) are optionally separated by methods known to the person skilled in the art into their enantiomers and/or diastereomers and/or reacted with the appropriate (i) solvents and/or (ii) bases to give their solvates, salts and/or solvates of the salts.

Inert solvents for the process step (II)+(III)→(IV) [amide coupling] are, for example, ethers such as diethyl ether, tert-butyl methyl ether, tetrahydrofuran, 1,4-dioxane, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethyl sulphoxide (DMSO), N,N-dimethylformamide (DMF), N,N'-dimethylpropyleneurea (DMPU) or N-methylpyrrolidinone (NMP). It is also possible to use mixtures of the solvents mentioned. Preference is given to using dichloromethane, tetrahydrofuran, dimethylformamide or mixtures of these solvents.

Suitable condensing agents for these coupling reactions are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl 5-methylisoxazolium perchlorate, acyl-amino compounds such as 2-ethoxy-1-ethoxycarbonyl-1,2-dihydroquinoline, α-chloroenamines such as 1-chloro-2-methyl-1-dimethylamino-1-propene, phosphorus compounds such as propane-phosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate or benzotriazol-1-yl-oxy-tris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyl uronium tetrafluoroborate (TPTU), O-(7-azabenzo triazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxybenzotriazole (HOBt) or N-hydroxysuccinimide (HOSu), and as bases alkali metal carbonates, for example sodium carbonate or potassium carbonate, or tertiary amine bases such as triethylamine, N-methylmorpholine, N-methylpiperidine, N,N-diisopropylethylamine, pyridine or 4-N,N-dimethylaminopyridine. Preference is given to using O-(7-azabenzotriazol-1-yl)-N,N,N',N'-tetramethyluronium hexafluorophosphate (HATU) in combination with pyridine or N,N-diisopropylethylamine, or N-(3-dimethylaminopropyl)-N'-ethylcarbodiimide hydrochloride (EDC) in combination with 1-hydroxybenzotriazole (HOBt) and triethylamine, or 1-chloro-2-methyl-1-dimethylamino-1-propene together with pyridine.

The reaction (II)+(III)→(IV) is generally carried out in a temperature range of from 0° C. to +60° C., preferably at from +10° C. to +40° C.

When a carbonyl chloride corresponding to the compound (II) is used, the coupling with the amine component (III) is carried out in the presence of a customary organic auxiliary base such as triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo-[4.3.0]non-5-ene (DBN). Preference is given to using triethylamine or N,N-diisopropylethylamine.

The reaction of the amine (III) with the carbonyl chloride is generally carried out in a temperature range of from −20° C. to +60° C., preferably in the range from −10° C. to +30° C.

For their part, the preparation of the carbonyl chlorides is carried out in a customary manner by treating the carboxylic acid (II) with thionyl chloride or oxalyl chloride.

The removal of the ester group $T^1$ in process step (IV)→ (I) is carried out by customary methods by treating the ester in inert solvents with acids or bases, where in the latter variant the salt initially formed is converted by treatment with acid into the free carboxylic acid. In the case of the tert-butyl esters, the ester cleavage is preferably carried out using acids. Benzyl esters are preferably cleaved by hydrogenolysis (hydrogenation) in the presence of a suitable catalyst such as, for example, palladium on activated carbon.

Suitable inert solvents for these reactions are water or organic solvents customary for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is also possible to use mixtures of the solvents mentioned above. In the case of a basic ester hydrolysis, preference is given to using mixtures of water with dioxane, tetrahydrofuran, methanol and/or ethanol. In the case of the reaction with trifluoroacetic acid, preference is given to using dichloromethane and in the case of the reaction with hydrogen chloride, preference is given to using tetrahydrofuran, diethyl ether, dioxane or water.

Suitable bases are the customary inorganic bases. These include in particular alkali or alkaline earth metal hydroxides such as, for example, lithium hydroxide, sodium hydroxide, potassium hydroxide or barium hydroxide, or alkali or alkaline earth metal carbonates such as sodium carbonate, potassium carbonate or calcium carbonate. Preference is given to lithium hydroxide, sodium hydroxide or potassium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof, if appropriate with addition of water. Preference is given to hydrogen chloride or trifluoroacetic acid in the case of the tert-butyl esters and hydrochloric acid in the case of the methyl esters.

The ester cleavage is generally carried out in a temperature range of from $-20°$ C. to $+100°$ C., preferably at from $0°$ C. to $+60°$ C.

The intermediates of the formula (II) can be prepared, for example, by
[A] initially deprotonating a carboxylic acid of the formula (V)

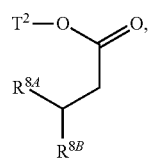

(V)

in which $R^{8A}$ and $R^{8B}$ have the meanings given above
and
$T^2$ represents $(C_1$-$C_4)$-alkyl or benzyl,
in an inert solvent with the aid of a base and then arylating in the presence of a suitable palladium catalyst with a phenyl bromide of the formula (VI)

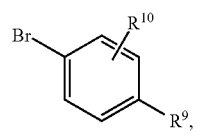

(VI)

in which $R^9$ and $R^{10}$ have the meanings give above, to give a compound of the formula (VII)

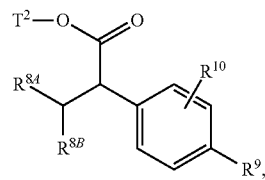

(VII)

in which $R^{8A}$, $R^{8B}$, $R^9$, $R^{1B}$ and $T^2$ have the meanings given above, or
[B] alkylating a phenylacetic ester of the formula (VIII)

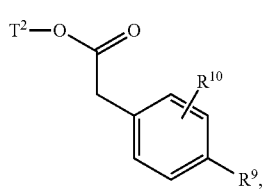

(VIII)

in which $R^9$ and $R^{10}$ have the meanings given above
and
$T^2$ represents $(C_1$-$C_4)$-alkyl or benzyl,
in an inert solvent in the presence of a base with a compound of the formula (IX)

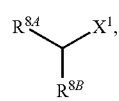

(IX)

in which $R^{8A}$ and $R^{8B}$ have the meanings given above
and
$X^1$ represents a suitable leaving group such as, for example, bromine or iodine,
to give the compound of the formula (VII)

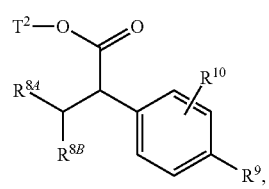

(VII)

in which $R^{8A}$, $R^{8B}$, $R^9$, $R^{10}$ and $T^2$ have the meanings given above, and then in each case removing the ester radical $T^2$ by basic or acidic solvolysis or, in the case that $T^2$ represents benzyl, also by hydrogenolysis, giving the carboxylic acid (II).

The arylation reaction in process step (V)+(VI)→(VII) is preferably carried out in toluene or toluene/tetrahydrofuran mixtures in a temperature range of from $+20°$ C. to $+100°$ C. Here, the base used for deprotonating the ester (V) is preferably lithium bis(trimethylsilyl)amide. Suitable palladium catalysts are, for example, palladium(II) acetate or tris(dibenzylideneacetone)dipalladium, in each case in combination with an electron-rich, sterically demanding phosphine ligand such as 2-dicyclohexylphosphino-2'-(N,N-dimethylamino)biphenyl or 2-di-tert-butyl-phosphino-2'-(N,N-dimethylamino)biphenyl [cf., for example, W. A. Moradi, S. L. Buchwald, *J. Am. Chem. Soc.* 123, 7996-8002 (2001)].

Inert solvents for the alkylation reaction (VIII)+(IX)→(VII) are, for example, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or mineral oil fractions, or dipolar aprotic solvents such as N,N-dimethylformamide (DMF), dimethyl sulphoxide (DMSO), N,N'-dimethylpropyleneurea (DMPU) or N-methylpyrrolidinone (NMP). It is also possible to use mixtures of the solvents mentioned. Preference is given to using tetrahydrofuran, dimethylformamide or mixtures thereof.

Suitable bases for the process step (VIII)+(IX)→(VII) are customary strong inorganic or organic bases. These include in particular alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, or amides such as lithium bis(trimethylsilyl)amide, sodium bis(trimethylsilyl)amide or potassium bis(trimethylsilyl)-amide or lithium diisopropylamide. Preference is given to using potassium tert-butoxide, sodium hydride or lithium diisopropylamide.

The reaction (VIII)+(IX)→(VII) is generally carried out in a temperature range of from −80° C. to +40° C., preferably at from −20° C. to +20° C.

The removal of the ester group $T^2$ in process step (VII)→(II) is carried out in an analogous manner as described above for the ester radical $T^1$.

Alternatively, intermediates of the formula (II-A)

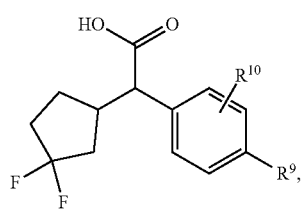

(II-A)

in which $R^9$ and $R^{10}$ have the meanings given above, can also be prepared by initially converting the phenylacetic ester of the formula (VIII)

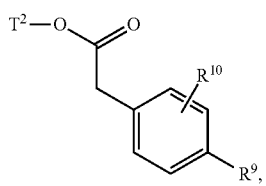

(VIII)

in which $R^9$, $R^{10}$ and $T^2$ have the meanings given above, by base-induced addition to 2-cyclopenten-1-one into a compound of the formula (X)

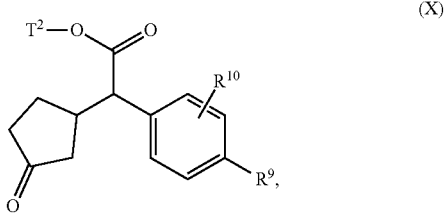

(X)

in which $R^9$, $R^{10}$ and $T^2$ have the meanings given above, then fluorinating this compound with 1,1'-[(trifluoro-$\lambda^4$-sulphonyl)imino]bis(2-methoxyethane) under boron trifluoride catalysis to give a compound of the formula (VII-A)

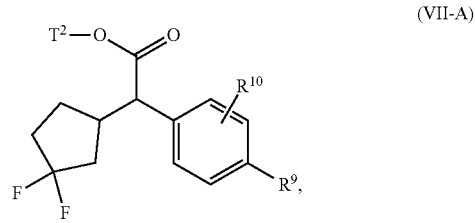

(VII-A)

in which $R^9$, $R^{10}$ and $T^2$ have the meanings given above, and subsequently removing the ester group T again giving the carboxylic acid (II-A).

In process step (VIII)→(X), for deprotonating the ester (VIII), preference is given to using an amide base such as lithium diisopropylamide or lithium bis(trimethylsilyl)amide. For the deoxy-fluorination in the transformation (X)→(VII-A), instead of the 1,1'-[(trifluoro-$\lambda^4$-sulphonyl)-imino]bis(2-methoxyethane) ("Desoxofluor") mentioned above, it is also possible, if appropriate, to employ other known fluorinating agents, such as diethylaminosulphur trifluoride (DAST) or morpholinosulphur trifluoride (morpho-DAST) [for the reaction sequence (VIII)→(X)→(VII-A), cf., for example, T. Mase et al., *J. Org. Chem.* 66 (20), 6775-6786 (2001)].

Depending on their substitution pattern, the intermediates of the formula (III) can be prepared, for example, by either [C-1] reacting a phosphonoacetic ester of the formula (XI)

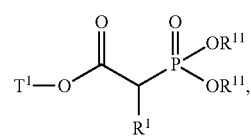

(XI)

in which $R^1$ and $T^1$ have the meanings given above and $R^{11}$ represents ($C_1$-$C_4$)-alkyl, in an inert solvent in a base-induced olefination reaction with a 3-nitrobenzoyl compound of the formula (XII)

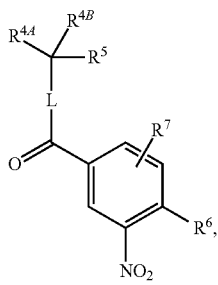
(XII)

in which L, $R^{4A}$, $R^{4B}$, $R^5$, $R^6$ and $R^7$ have the meanings given above, to give a compound of the formula (XIII)

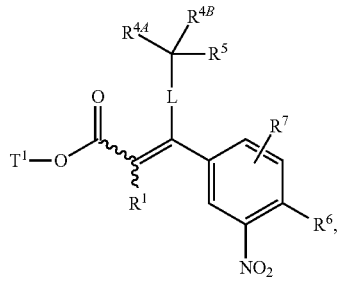
(XIII)

in which L, $R^{4A}$, $R^{4B}$, $R^5$, $R^6$, $R^7$ and $T^1$ have the meanings given above, and then hydrogenating this compound in the presence of a suitable palladium or platinum catalyst to give a 3-(3-aminophenyl)propionic ester of the formula (III-A)

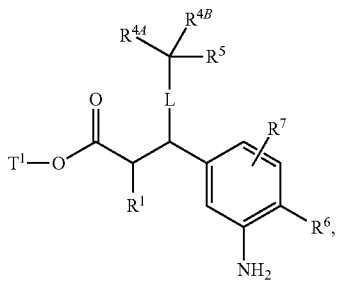
(III-A)

in which L, $R^1$, $R^{4A}$, $R^{4B}$, $R^5$, $R^6$, $R^7$ and $T^1$ have the meanings given above, or

[C-2] reacting a phosphonoacetic ester of the formula (XI)

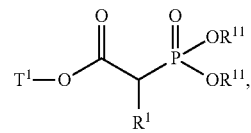
(XI)

in which $R^1$ and $T^1$ have the meanings given above and $R^{11}$ represents $(C_1-C_4)$-alkyl in an inert solvent in a base-induced olefination reaction with a protected 3-aminobenzoyl compound of the formula (XIV)

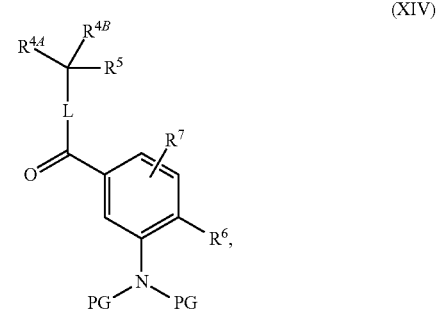
(XIV)

in which L, $R^{4A}$, $R^{4B}$, $R^5$, $R^6$ and $R^7$ have the meanings given above and PG represents benzyl or 4-methoxybenzyl as inert amino protective group to give a compound of the formula (XV)

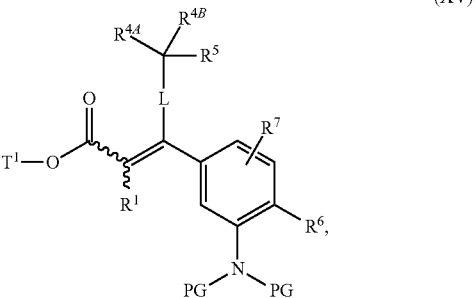
(XV)

in which L, PG, $R^1$, $R^{4A}$, $R^{4B}$, $R^5$, $R^6$, $R^7$ and $T^1$ have the meanings given above, then either (i) reducing this compound with magnesium in methanol to give a compound of the formula (XVI)

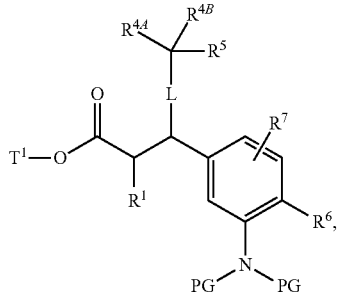
(XVI)

in which L, PG, $R^1$, $R^{4A}$, $R^{4B}$, $R^5$, $R^6$, $R^7$ and $T^1$ have the meanings given above, and subsequently removing the amino protective groups PG according to customary methods by hydrogenolysis or oxidatively giving the 3-(3-aminophenyl)propionic ester of the formula (III-A)

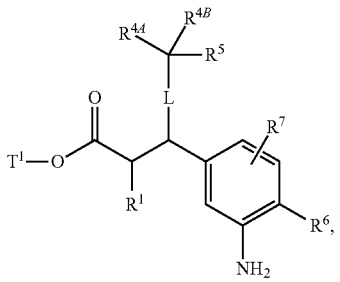
(III-A)

in which L, $R^1$, $R^{4A}$, $R^{4B}$, $R^5$, $R^6$, $R^7$ and $T^1$ have the meanings given above, or (ii) converting the compound of the formula (XV) in a one-step process by hydrogenation in the presence of a suitable palladium or platinum catalyst into the 3-(3-aminophenyl)propionic ester of the formula (III-A), or

[D] coupling an acrylic ester derivative of the formula (XVII)

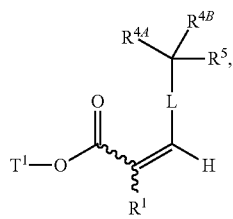
(XVII)

in which L, $R^1$, $R^{4A}$, $R^{1B}$, $R^5$ and $T^1$ have the meanings given above, in an inert solvent under palladium catalysis with a 3-amino- or 3-nitrophenyl bromide of the formula (XVIII)

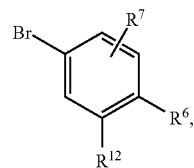
(XVIII)

in which $R^6$ and $R^7$ have the meanings given above and $R^{12}$ represents amino or nitro, to give a compound of the formula (XIX)

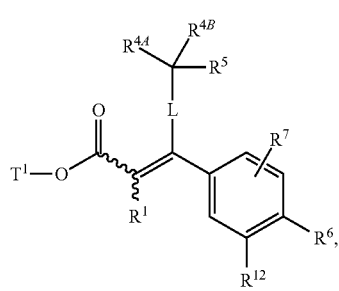
(XIX)

in which L, $R^1$, $R^{4A}$, $R^{4B}$, $R^5$, $R^6$, $R^7$, $R^{12}$ and $T^1$ have the meanings given above, and then reducing this compound with hydrogen in the presence of a suitable palladium or platinum catalyst or, in the case that $R^{12}$ represents amino, alternatively with magnesium in methanol to give the 3-(3-aminophenyl)propionic ester of the formula (III-A)

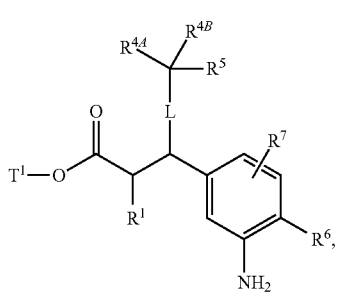
(III-A)

in which L, $R^1$, $R^{4A}$, $R^{4B}$, $R^5$, $R^6$, $R^7$ and $T^1$ have the meanings given above, or

[E-1] converting a phenyl iodide of the formula (XX)

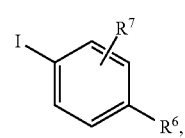
(XX)

in which $R^6$ and $R^7$ have the meanings given above, in an inert solvent with isopropylmagnesium chloride in the presence of lithium chloride into the corresponding phenylmagnesium compound, then coupling this compound in situ under copper(I) catalysis with an alkylidenemalonic ester of the formula (XXI)

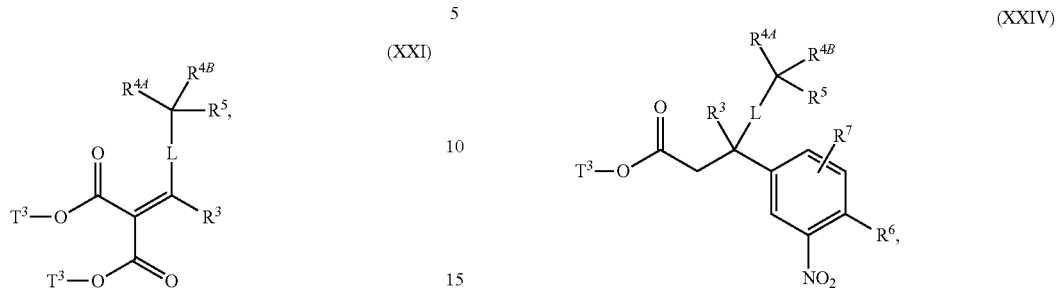
(XXI)

in which L, R³, R⁴ᴬ, R⁴ᴮ and R⁵ have the meanings given above
and
T³ represents methyl or ethyl,
to give a compound of the formula (XXII)

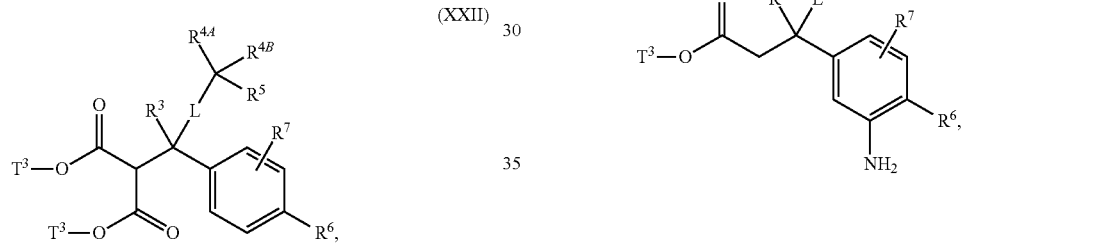
(XXII)

in which L, R³, R⁴ᴬ, R⁴ᴮ, R⁵, R⁶, R⁷ and T³ have the meanings given above, then removing one of the two ester groupings by heating with lithium chloride in a DMSO/water mixture, then converting the resulting 3-phenylpropionic ester of the formula (XXIII)

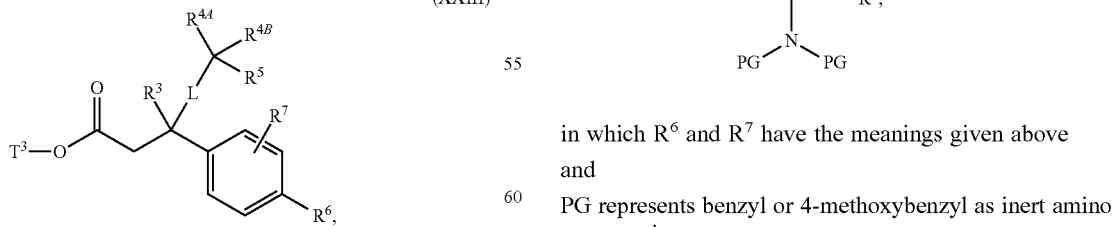
(XXIII)

in which L, R³, R⁴ᴬ, R⁴ᴮ, R⁵, R⁶, R⁷ and T³ have the meanings given above, by reaction with nitronium tetrafluoroborate into the 3-nitrophenyl derivative of the formula (XXIV)

(XXIV)

in which L, R³, R⁴ᴬ, R⁴ᴮ, R⁵, R⁶, R⁷ and T³ have the meanings given above, and finally hydrogenating in the presence of a suitable palladium or platinum catalyst to give a 3-(3-aminophenyl)propionic ester of the formula (III-B)

(III-B)

in which L, R³, R⁴ᴬ, R⁴ᴮ, R⁵, R⁶, R⁷ and T³ have the meanings given above, or

[E-2] converting a protected 3-aminophenyl iodide of the formula (XXV)

(XXV)

in which R⁶ and R⁷ have the meanings given above
and
PG represents benzyl or 4-methoxybenzyl as inert amino protective group, in an inert solvent with isopropylmagnesium chloride in the presence of lithium chloride into the corresponding phenyl magnesium compound, then coupling this compound in situ under copper(I) catalysis with an alkylidenemalonic ester of the formula (XXI)

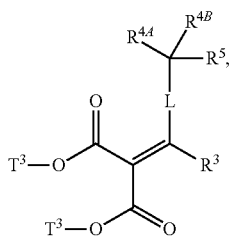

(XXI)

in which L, $R^3$, $R^{4A}$, $R^{4B}$ and $R^5$ have the meanings given above
and
$T^3$ represents methyl or ethyl,
to give a compound of the formula (XXVI)

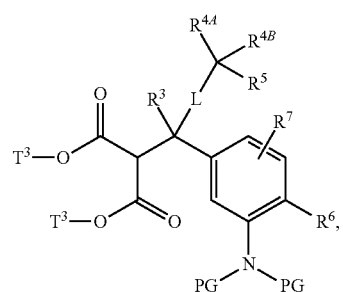

(XXVI)

in which L, PG, $R^3$, $R^{4A}$, $R^{4B}$, $R^5$, $R^6$, $R^7$ and $T^3$ have the meanings given above,
then deprotecting this compound by hydrogenolysis or by treatment with a suitable oxidizing agent such as, for example, 2,3-dichloro-5,6-dicyano-1,4-benzoquinone (DDQ) to give a compound of the formula (XXVII)

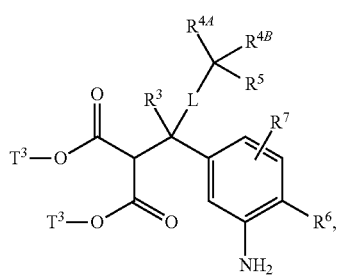

(XXVII)

in which L, $R^3$, $R^{4A}$, $R^{4B}$, $R^5$, $R^6$, $R^7$ and $T^3$ have the meanings given above,
and then removing one of the two ester groupings by heating with lithium chloride in a DMSO/water mixture, to give the 3-(3-aminophenyl)propionic ester of the formula (III-B)

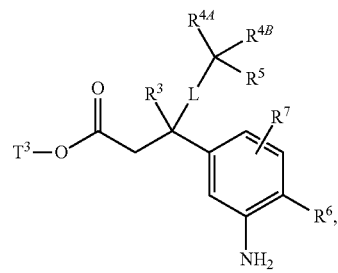

(III-B)

in which L, $R^3$, $R^{4A}$, $R^{4B}$, $R^5$, $R^6$, $R^7$ and $T^3$ have the meanings given above,
or
[F] alkylating a carboxylic ester of the formula (XXVIII)

(XXVIII)

in which $R^1$, $R^2$ and $T^1$ have the meanings given above,
in an inert solvent after α-deprotonation with a 3-bromobenzyl compound of the formula (XXIX)

(XXIX)

in which L, $R^{4A}$, $R^{4B}$, $R^5$, $R^6$ and $R^7$ have the meanings given above
and
$X^2$ represents a suitable leaving group, such as chlorine, bromine, iodine, mesylate, triflate or tosylate,
to give a compound of the formula (XXX)

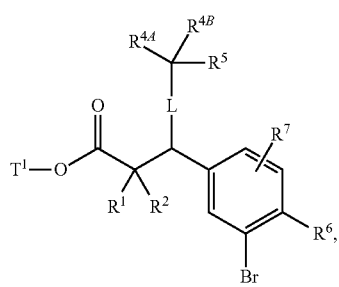

(XXX)

in which L, $R^1$, $R^2$, $R^{4A}$, $R^{4B}$, $R^5$, $R^6$, $R^7$ and $T^1$ have the meanings given above, then reacting with benzylamine in the presence of a base and a palladium catalyst to give a compound of the formula (XXXI)

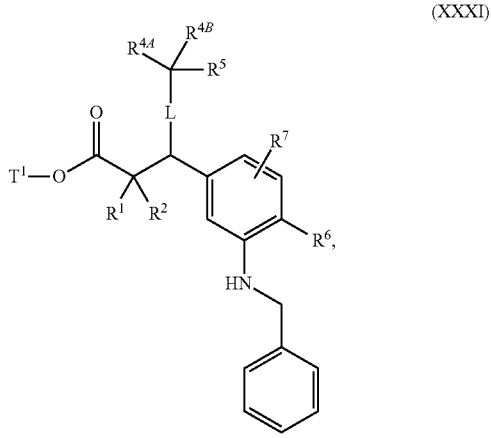

in which L, $R^1$, $R^2$, $R^{4A}$, $R^{4B}$, $R^5$, $R^6$, $R^7$ and $T^1$ have the meanings given above, and then removing the N-benzyl group by hydrogenolysis, to give a 3-(3-aminophenyl)propionic ester of the formula (III-C)

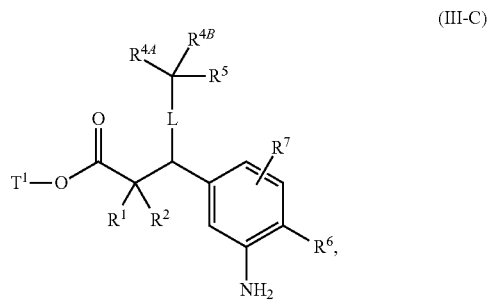

in which L, $R^1$, $R^2$, $R^{4A}$, $R^{4B}$, $R^5$, $R^6$, $R^7$ and $T^1$ have the meanings given above.

Suitable for deprotonating the phosphono ester (XI) in the olefination reactions (XI)+(XII)→(XIII) and (XI)+(XIV)→(XV) are in particular non-nucleophilic strong bases such as, for example, sodium hydride or potassium hydride, lithium bis(trimethylsilyl)amide, sodium bis(trimethylsilyl)amide or potassium bis(trimethylsilyl)amide or lithium diisopropylamide; preference is given to using sodium hydride.

The hydrogenation in the process steps (XIII)→(III-A), (XV)→(III-A), (XIX)→(III-A) and (XXIV)→(III-B) is generally carried out under a stationary hydrogen atmosphere at atmospheric or elevated pressure. The preferred catalyst used is palladium or platinum on activated carbon (as support material). The removal of the amino protective group(s) in the transformations (XVI)→(III-A), (XXVI)→(XXVII) and (XXXI)→(III-C) is usually carried out by hydrogenolysis according to the same procedure; if PG in (XVI) or (XXVI) represents p-methoxybenzyl, this may alternatively also be carried out oxidatively, for example with the aid of 2,3-dichloro-5,6-dicyano-1,4-benzoquinone (DDQ) or ammonium cerium(IV) nitrate.

Preferred for use as palladium catalyst for the reaction (XVII)+(XVIII)→(XIX) [Heck reaction] is palladium(II) acetate or tris(dibenzylideneacetone)dipalladium(0), in each case in combination with a phosphine ligand such as, for example, tri-tert-butylphosphine, triphenylphosphine or tri-2-tolylphosphine.

The conversion of the phenyl iodide (XX) into the corresponding phenylmagnesium compound and its copper(I)-mediated 1,4-addition to the alkylidenemalonate (XXI) to give the product of the formula (XXII) are carried out by a general method known from the literature [see, for example, P. Knochel et al., *Tetrahedron* 56, 2727-2731 (2000), and the literature cited therein]; this also applies to the analogous reaction (XXV)+(XXI)→(XXVI).

Particularly suitable for the α-deprotonation of the carboxylic ester (XXVIII) in the alkylation reaction (XXVIII)+(XXIX)→(XXX) are non-nucleophilic strong bases such as, for example, sodium tert-butoxide or potassium tert-butoxide, sodium hydride or potassium hydride, lithium diisopropylamide or lithium bis(trimethylsilyl)amide; sodium bis(trimethylsilyl)amide or potassium bis(trimethylsilyl)amide; preference is given to using lithium diisopropylamide. Preferred inert solvents for this reaction are ethers such as diethyl ether, diisopropyl ether, methyl tert-butyl ether, tetrahydrofuran, glycol dimethyl ether or diethylene glycol dimethyl ether. The reaction is usually carried out in a temperature range of from −80° C. to +25° C.

For the transformation (XXX)→(XXXI) [Buchwald-Hartwig coupling with benzylamine], the preferred catalyst tris(dibenzylideneacetone)dipalladium(0) in combination with (±)-2,2'-bis-(diphenylphosphino)-1,1'-binaphthyl is phosphine ligand, and the preferred base is sodium tert-butoxide or potassium tert-butoxide [cf., for example, J. P. Wolfe and S. L. Buchwald, *Organic Syntheses*, Coll. Vol. 10, 423 (2004), Vol. 78, 23 (2002)].

The reactions described above can be carried out at atmospheric pressure, at elevated pressure or at reduced pressure (for example in the range of from 0.5 to 5 bar); in general in each case carried out at atmospheric pressure.

Separation of the compounds according to the invention into the corresponding enantiomers and/or diastereomers can take place where appropriate, depending on expediency, even at the stage of the compounds (II), (III), (IV), (VII), (XVI), (XXII), (XXIII), (XXIV), (XXVI), (XXVII), (XXX) or (XXXI), which are then reacted further in separated form in accordance with the above-described process sequences. Such separation can be carried out by conventional methods known to a person skilled in the art. In the context of the present invention, preference is given to using chromatographic methods on achiral or chiral separation phases; in the case of carboxylic acids and as intermediates or end products, separation may alternatively also be via diastereomeric salts.

The compounds of the formulae (V), (VI), (VIII), (IX), (XI), (XII), (XIV), (XVII), (XVIII), (XX), (XXI), (XXV), (XXVIII) and (XXIX) are either commercially available or described as such in the literature, or they can be prepared in a manner obvious to the person skilled in the art analogously to the methods published in the literature. Numerous detailed procedures and literature references for preparing the starting materials can also be found in the Experimental Part in the section on the preparation of the starting materials and intermediates.

The preparation of the compounds according to the invention can be illustrated in an exemplary manner by the reaction schemes below:

Scheme 1
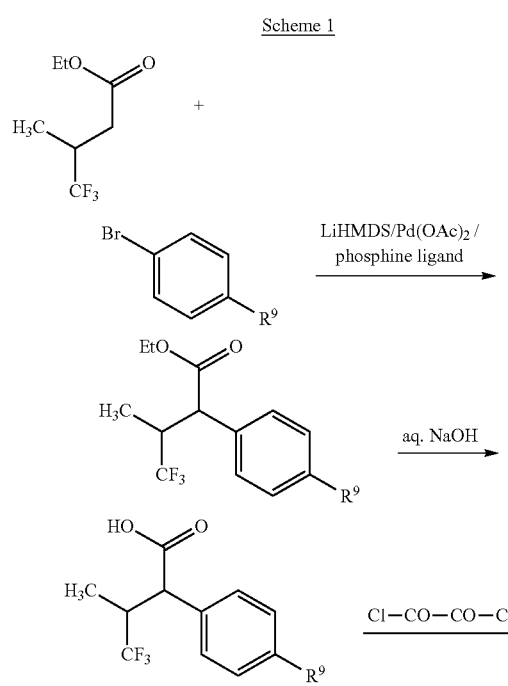
Scheme 2
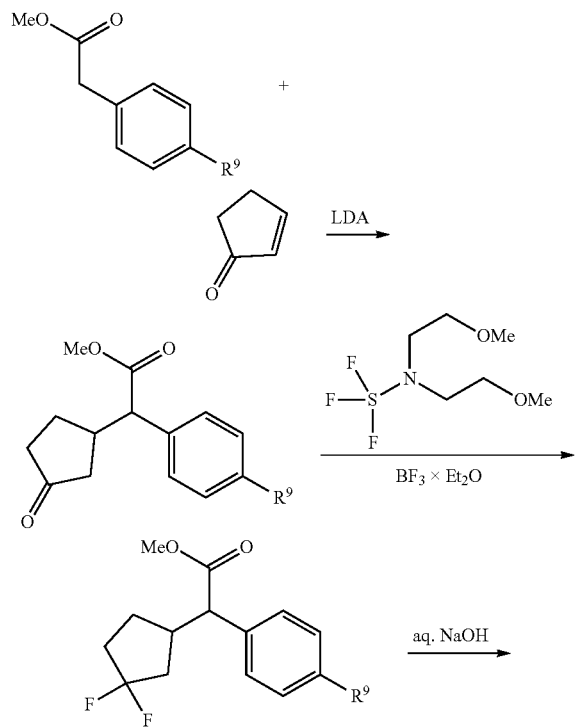
-continued
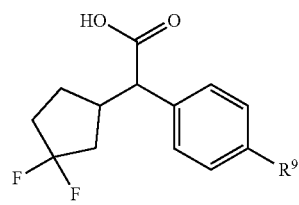
Scheme 3a
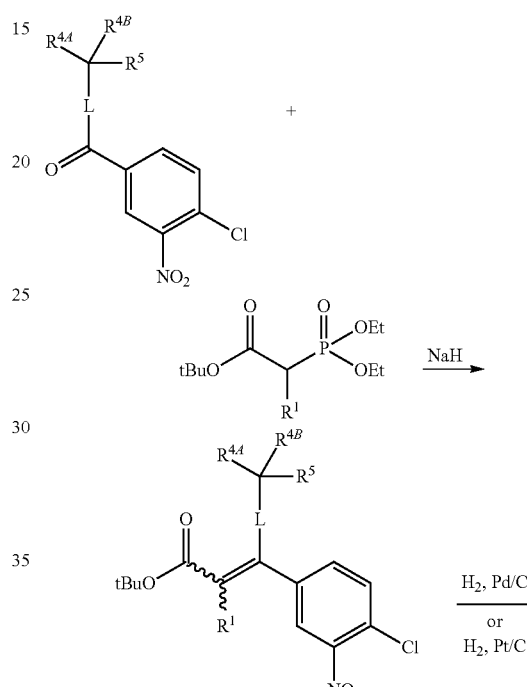
Scheme 3b
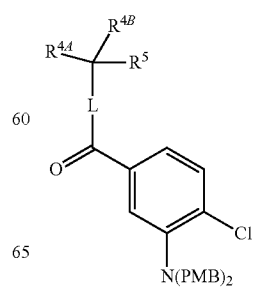

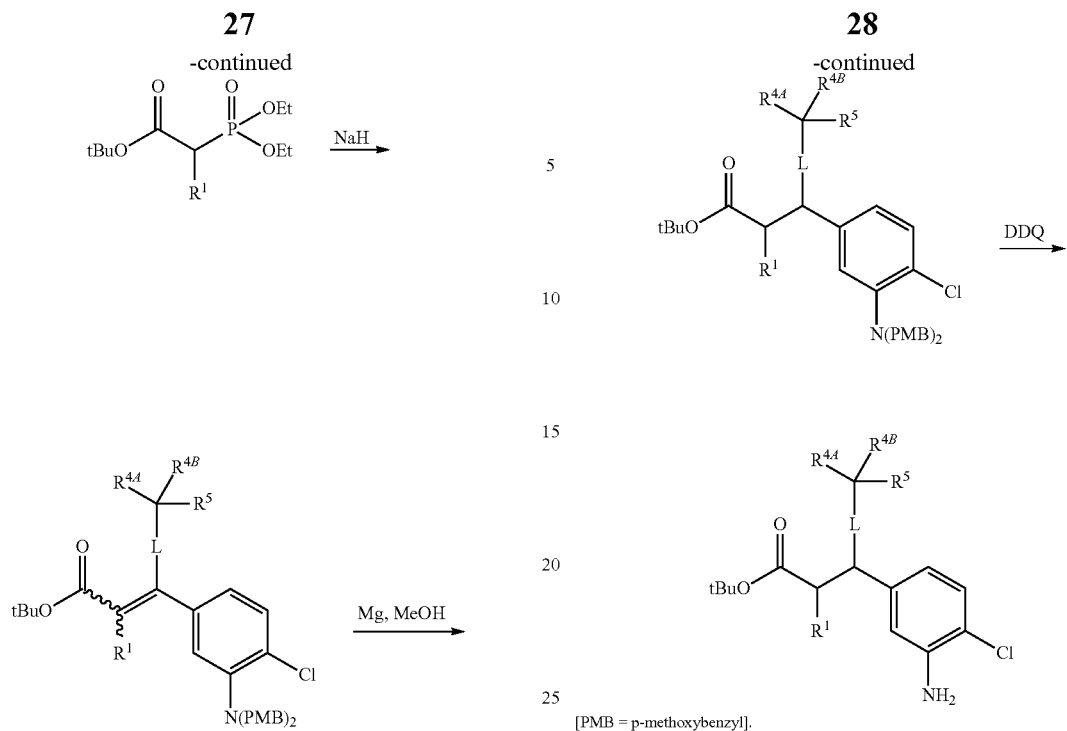
[PMB = p-methoxybenzyl].
Scheme 4
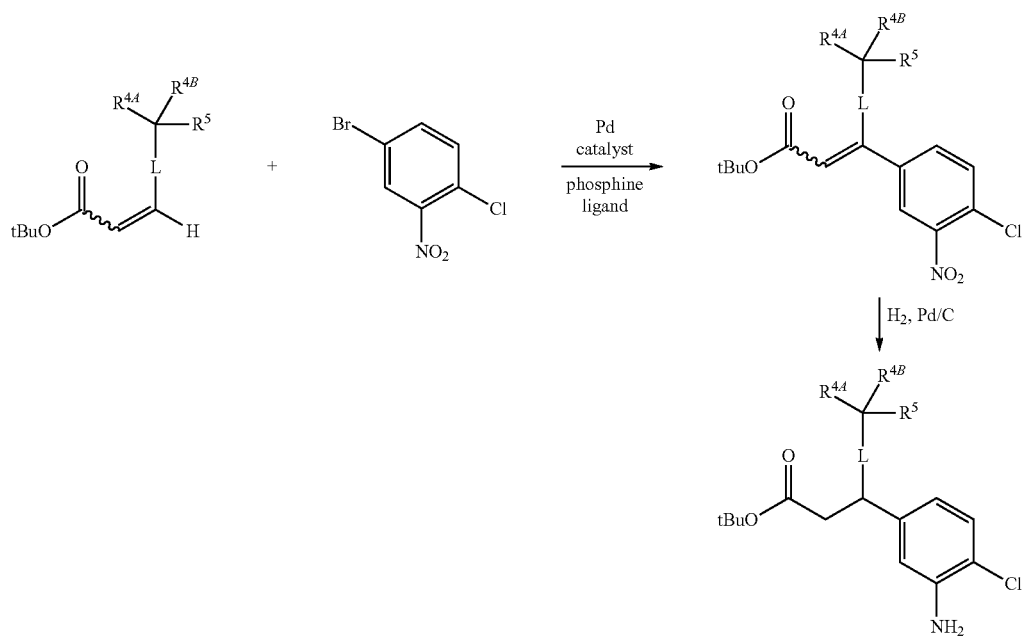

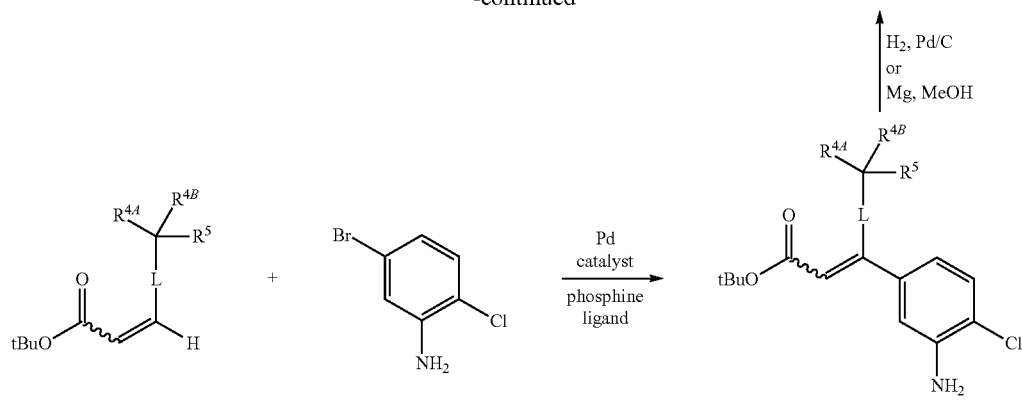
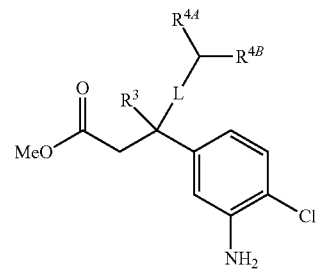
Scheme 5a
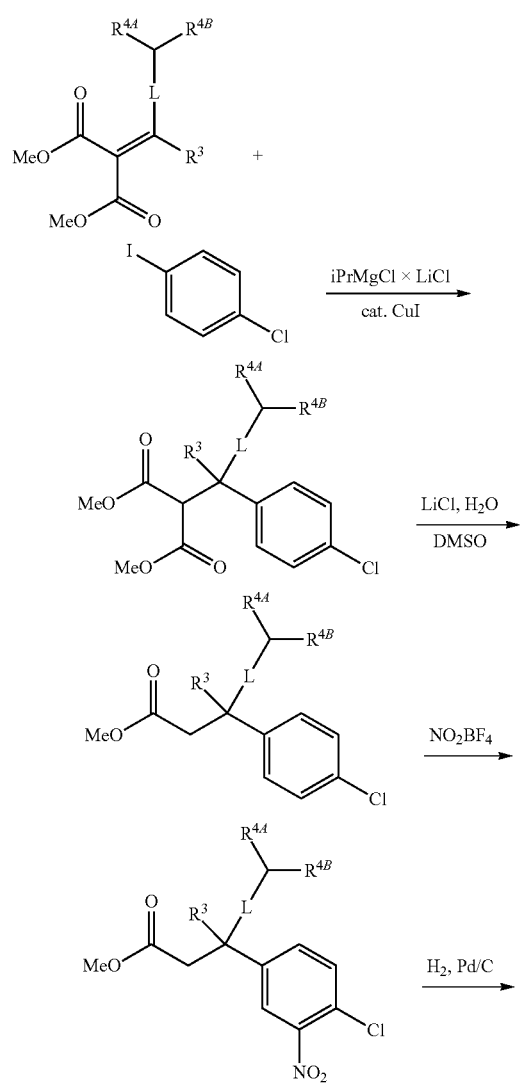
Scheme 5b
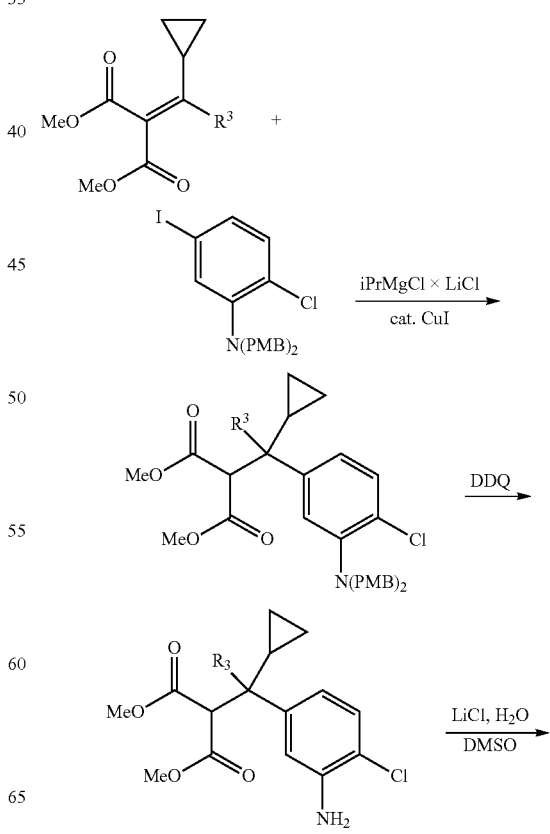

-continued

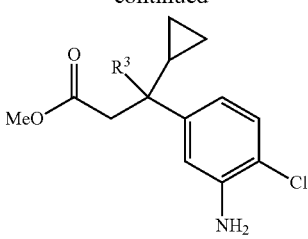

[PMB = p-methoxybenzyl].

Scheme 6

The compounds according to the invention have valuable pharmacological properties and can be used for the prevention and treatment of disorders in humans and animals.

The compounds according to the invention are potent activators of soluble guanylate cyclase. They lead to vasorelaxation, inhibition of platelet aggregation and lowering of blood pressure and increase of coronary blood flow. These effects are mediated via direct haem-independent activation of soluble guanylate cyclase and an increase of intracellular cGMP.

In addition, the compounds according to the invention have advantageous pharmacokinetic properties, in particular with respect to their bioavailability and/or duration of action after intravenous or oral administration.

The compounds according to the invention are particularly suitable for the treatment and/or prevention of cardiovascular, pulmonary, thromboembolic and fibrotic disorders.

Accordingly, the compounds according to the invention can be used in medicaments for the treatment and/or prevention of cardiovascular disorders such as, for example, high blood pressure (hypertension), heart failure, coronary heart disease, stable and unstable angina pectoris, pulmonary arterial hypertension (PAH) and other forms of pulmonary hypertension (PH), renal hypertension, peripheral and cardiovascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prevention of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, microvascular and macrovascular damage (vasculitis), and also to prevent restenosis, for example after thrombolysis therapies, percutaneous transluminal angioplasties (PTA), percutaneous transluminal coronary angioplasties (PTCA), heart transplants and bypass operations.

In the context of the present invention, the term heart failure includes both acute and chronic manifestations of heart failure as well as more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be employed for the treatment and/or prevention of arteriosclerosis, a disturbed lipid metabolism, hypolipoproteinaemias, dilipideamias, hypertriglyceridaemias, hyperlipidaemias, combined hyperlipidaemias, hyper-cholesterolaemias, abetalipoproteinaemias, sitosterolaemia, xanthomatosis, Tangier disease, adiposity, obesity and metabolic syndrome.

Furthermore, the compounds according to the invention can be used for the treatment and/or prevention of primary and secondary Raynaud's phenomenon, of microcirculation impairments, claudication, tinnitus, peripheral and autonomic neuropathies, diabetic microangiopathies, diabetic retinopathy, diabetic ulcers on the extremities, gangrene, CREST syndrome, erythematosis, onychomycosis and rheumatic disorders.

In addition, the compounds according to the invention can be used for preventing ischaemia- and/or reperfusion-related damage to organs or tissues and also as additives for perfusion and preservation solutions of organs, organ parts, tissues or tissue parts of human or animal origin, in particular for surgical interventions or in the field of transplantation medicine.

The compounds according to the invention are furthermore suitable for the treatment and/or prevention of kidney disorders, in particular of renal insufficiency and renal failure. In the context of the present invention, the terms renal insufficiency and renal failure comprise both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminurea, macroalbuminurea, lesions on glomerulae and arterioles, tubular dilatation, hyperphosphataemia and/or need for dialysis. The present invention also comprises the use of the compounds according to the invention for the treatment and/or prevention of sequelae of renal insufficiency, such as, for example hypertension, pulmonary oedema, heart failure, uraemia, anaemia, electrolyte disturbances (for example hypercalaemia, hyponatraemia) and disturbances in bone and carbohydrate metabolism.

In addition, the compounds according to the invention are suitable for the treatment and/or prevention of disorders of the urogenital system such as, for example, benign prostate syndrome (BPS), benign prostate hyperplasia (BPH), benign prostate enlargement (BPE), bladder outlet obstruction (BOO), lower urinary tract syndrome (LUTS), neurogenic overactive bladder (OAB), incontinence such as, for example, mix, urge, stress or overflow incontinence (MUI, UUI, SUI, OUI), pelvic pain, and also erectile dysfunction and female sexual dysfunction.

The compounds according to the invention are also suitable for the treatment and/or prevention of asthmatic disorders, chronic-obstructive pulmonary disease (COPD), acute respiratory distress syndrome (ARDS) and acute lung injury (ALI), alpha-1-antitrypsin deficiency (AATD), pulmonary fibrosis, pulmonary emphysema (for example pulmonary emphysema induced by cigarette smoke) and cystic fibrosis (CF), and also of pulmonary arterial hypertension (PAH) and other forms of pulmonary hypertension (PH) including left-heart disease, HIV, sickle cell anaemia, thromboembolisms, sarcoidosis, COPD or pulmonary fibrosis-associated pulmonary hypertension.

The compounds described in the present invention also represent active compounds for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jakob dementia, HIV dementia, schizophrenia with dementia or Korsakoff's psychosis. They are also suitable for the treatment and/or prevention of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischaemias and craniocerebral trauma. The compounds according to the invention can likewise be employed for controlling states of pain.

In addition, the compounds according to the invention have antiinflammatory action and can therefore be used as antiinflammatory agents for the treatment and/or prevention of sepsis (SIRS), multiple organ failure (MODS, MOF), inflammatory disorders of the kidney, chronic inflammation of the bowel (IBS, Crohn's disease, ulcerative colitis), pancreatitis, peritonitis, rheumatoid disorders, inflammatory skin diseases and inflammatory eye diseases.

The compounds according to the invention are furthermore suitable for the treatment and/or prevention of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following disorders: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring, naevi, diabetic retinopathy, proliferative vitreoretinopathy and disorders of the connective tissue (for example sarcoidosis). The compounds according to the invention can also be used to promote wound healing, for controlling postoperative scarring, for example as a result of glaucoma operations, and cosmetically for ageing and keratinized skin.

By virtue of their activity profile, the compounds according to the invention are particularly suitable for the treatment and/or prevention of cardiovascular disorders such as heart failure, angina pectoris, hypertension and pulmonary hypertension, and also of thromboembolic disorders and ischaemias, vascular disorders, disturbances of microcirculation, renal insufficiency, fibrotic disorders and arteriosclerosis.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prevention of the aforementioned disorders. Preferred examples of suitable active compound combinations include:

- organic nitrates and NO donors, for example sodium nitroprusside, nitroglycerin, isosorbide mononitrate, isosorbide dinitrate, molsidomine or SIN-1, and inhaled NO;
- compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
- NO-independent, but ham-dependent stimulators of guanylate cyclase, such as, in particular, riociguat and the compounds described in WO 00/06568, WO 00/06569, WO 02/42301 and WO 03/095451;
- agents having an antithrombotic effect, for example and with preference from the group of platelet aggregation inhibitors, of anticoagulants or of profibrinolytic substances;
- active compounds which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
- active compounds which alter lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, by way of example and preferably, aspirin, clopidogrel, ticlopidine or dipyridamol.

In a preferred embodiment of the invention, the compounds according to the invention are administered in combination with a thrombin inhibitor such as, by way of example and preferably, ximelagatran, melagatran, dabigatran, bivalirudin or clexane.

In a preferred embodiment of the invention, the compounds according to the invention are administered in combination with a GPIIb/IIIa antagonist such as, by way of example and preferably, tirofiban or abciximab.

In a preferred embodiment of the invention, the compounds according to the invention are administered in combination with a factor Xa inhibitor such as, by way of example and preferably, rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as, by way of example and preferably, coumarin.

Agents which lower blood pressure are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist such as, by way of example and preferably, nifedipine, amlodipine, verapamil or diltiazem.

In a preferred embodiment of the invention, the compounds according to the invention are administered in combination with an alpha-1 receptor blocker such as, by way of example and preferably, prazosin.

In a preferred embodiment of the invention, the compounds according to the invention are administered in combination with a beta receptor blocker such as, by way of example and preferably, propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, by way of example and preferably, losartan, candesartan, valsartan, telmisartan or embusartan.

In a preferred embodiment of the invention, the compounds according to the invention are administered in combination with an ACE inhibitor such as, by way of example and preferably, enalapril, captopril, lisinopril, ramipril, delapril, fosinopril, quinapril, perindopril or trandopril.

In a preferred embodiment of the invention, the compounds according to the invention are administered in combination with an endothelin antagonist such as, by way of example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic, such as, for example and preferably, furosemide, bumetanide, torsemide, bendroflumethiazide, chlorothiazide, hydrochlorothiazide, hydro-flumethiazide, methylclothiazide, polythiazide, trichloromethiazide, chlorthalidone, indapamide, metolazone, quinethazone, acetazolamide, dichlorphenamide, methazolamide, glycerol, isosorbide, mannitol, amiloride or triamterene.

Agents which alter lipid metabolism are preferably understood to mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds according to the invention are administered in combination with a CETP inhibitor such as, by way of example and preferably, torcetrapib (CP-529 414), JJT-705 or CETP vaccine (Avant).

In a preferred embodiment of the invention, the compounds according to the invention are administered in combination with a thyroid receptor agonist such as, by way of example and preferably, D-thyroxin, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins such as, by way of example and preferably, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor such as, by way of example and preferably, BMS-188494 or TAK-475.

In a preferred embodiment of the invention, the compounds according to the invention are administered in combination with an ACAT inhibitor such as, by way of example and preferably, avasimibe, melinamide, pactimibe, eflucimibe or SMP-797.

In a preferred embodiment of the invention, the compounds according to the invention are administered in combination with an MTP inhibitor such as, by way of example and preferably, implitapide, BMS-201038, R-103757 or JTT-130.

In a preferred embodiment of the invention, the compounds according to the invention are administered in combination with a PPAR-gamma agonist such as, by way of example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, by way of example and preferably, ezetimibe, tiqueside or pamaqueside.

In a preferred embodiment of the invention, the compounds according to the invention are administered in combination with a lipase inhibitor such as, by way of example and preferably, orlistat.

In a preferred embodiment of the invention, the compounds according to the invention are administered in combination with a polymeric bile acid adsorbent such as, by way of example and preferably, cholestyramine, colestipol, colesolvam, CholestaGel or colestimide.

In a preferred embodiment of the invention, the compounds according to the invention are administered in combination with a bile acid reabsorption inhibitor such as, by way of example and preferably, ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist such as, by way of example and preferably, gemcabene calcium (CI-1027) or nicotinic acid.

The present invention further provides medicaments which comprise at least one compound according to the invention, typically together with one or more inert, nontoxic, pharmaceutically suitable auxiliaries, and the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral or parenteral administration is preferred, especially oral and intravenous administration.

The compounds according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration data for liquid/liquid solutions are based in each case on volume.

A. EXAMPLES

Abbreviations and acronyms:
abs. absolute
Ac acetyl
AIBN 2,2'-azobis-(2-methylpropionitrile)
aq. aqueous, aqueous solution
ATP adenosine 5'-triphosphate
Bn benzyl
Brij® polyethylene glycol dodecyl ether
BSA bovine serum albumin
Ex. example
Bu butyl
c concentration
cat. catalytic
CI chemical ionization (in MS)
d day(s)
DAST diethylaminosulphur trifluoride
DC thin-layer chromatography
DCI direct chemical ionization (in MS)
DDQ 2,3-dichloro-5,6-dicyano-1,4-benzoquinone
de diastereomeric excess
DMF dimethylformamide
DMSO dimethyl sulphoxide
DTT dithiothreitol
EDC N'-(3-dimethylaminopropyl)-N-ethylcarbodiimide hydrochloride
ee enantiomeric excess
EI electron impact ionization (in MS)
ent enantiomerically pure, enantiomer
eq. equivalent(s)
ESI electrospray ionization (in MS)
Et ethyl
GC gas chromatography
sat. saturated
GTP guanosine 5'-triphosphate
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high pressure, high performance liquid chromatography
iPr isopropyl
conc. concentrated
LC-MS liquid chromatography-coupled mass spectroscopy
LDA lithium diisopropylamide
LiHMDS lithium hexamethyldisilazide [lithium bis(trimethylsilyl)amide]
Me methyl
min minute(s)
MS mass spectroscopy
NBS N-bromosuccinimide
NMP N-methylpyrrolidin-2-one
NMR nuclear magnetic resonance spectroscopy
p para
Pd/C palladium on activated carbon
Ph phenyl
PMB p-methoxybenzyl
Pr propyl
Pt/c platinum on activated carbon
rac racemic, racemate
$R_f$ retention index (in TLC)
RP reverse phase (in HPLC)
RT room temperature
$R_t$ retention time (in HPLC or GC)
tBu tert-butyl
TEA triethanolamine
TFA trifluoroacetic acid
THF tetrahydrofuran
UV ultraviolet spectroscopy
v/v ratio by volume (of a solution)

GC-MS and LC-MS Methods:

Method 1 (GC-MS):
  Instrument: Micromass GCT, GC 6890; column: Restek RTX-35, 15 m×200 µm×0.33 µm; constant helium flow: 0.88 ml/min; oven: 70° C.; inlet: 250° C.; gradient: 70° C., 30° C./min→310° C. (maintained for 3 min).

Method 2 (LC-MS):
  MS instrument type: Waters Micromass Quattro Micro; HPLC instrument type: Agilent 1100 Series; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 3 (LC-MS):
  MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS):
  Instrument: Micromass Quattro Premier with Waters UPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 5 (LC-MS):
  Instrument: Waters Acquity SQD UPLC System; column: Waters Acquity UPLC HSS T3 1.8µ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 6 (GC-MS):

Instrument: Thermo DFS, Trace GC Ultra; column: Restek RTX-35, 15 m×200 μm×0.33 μm; constant helium flow: 1.20 ml/min; oven: 60° C.; inlet: 220° C.; gradient: 60° C., 30° C./min→300° C. (maintained for 3.33 min).

Method 7 (LC-MS):

Instrument: Waters Acquity SQD UPLC System; column: Waters Acquity UPLC HSS T3 1.8μ, 30 mm×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.60 ml/min; oven: 50° C.; UV detection: 208-400 nm.

Method 8 (LC-MS):

Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; flow rate: 0.3 ml/min; oven: 50° C.; UV detection: 210 nm.

Starting Materials and Intermediates:

Example 1A tert-Butyl (2E/Z)-4-methoxy-4-methylpent-2-enoate

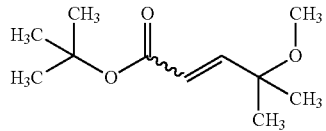

At −70° C. and under argon, 6.8 ml (96 mmol) of DMSO in 10 ml of dichloromethane were added dropwise to a mixture of 24 ml (48 mmol) of a 2 M solution of oxalyl chloride in dichloromethane and a further 100 ml of dichloromethane, and the mixture was stirred for 15 minutes. 5.2 ml (48 mmol) of 2-methoxy-2-methylpropan-1-ol [H. Garcia el al., Chem. Eur. J. 16 (28), 8530-8536 (2010)], dissolved in 15 ml of dichloromethane, were then added dropwise, and the mixture was stirred at −70° C. for another 15 min. 22.1 ml (158 mmol) of triethylamine were added slowly, and the reaction mixture was then stirred for another 15 min and subsequently slowly warmed to room temperature. 22 g (58 mmol) of tert-butyl (triphenyl-$\lambda^5$-phosphanylidene)acetate were then added, and the reaction mixture was stirred at room temperature overnight. The reaction solution was then slowly added to 100 ml of ice-water, and the phases obtained were separated. The organic phase was washed twice with in each case 100 ml of water, dried over magnesium sulphate and concentrated under reduced pressure on a rotary evaporator (water bath temperature 40° C., pressure not below 150 mbar). The residue obtained was taken up in about 100 ml of diethyl ether and allowed to stand in a fridge at +3° C. for 2 days. The precipitated triphenylphosphine oxide was filtered off, and the filtrate was concentrated under reduced pressure. The residue obtained was purified by chromatography on silica gel (mobile phase cyclohexane/ethyl acetate 100:1→50:1). This gave 7.06 g (73% of theory) of the title compound as a colourless liquid.

GC-MS (method 6): $R_t$=3.32 min, m/z=218 (M+NH$_4$)$^+$.

The two compounds below were obtained analogously to synthesis Example 1A:

| Example | Name/Structure/Starting materials | Analytical data |
|---|---|---|
| 2A | tert-butyl (2E)-3-(3,3-difluorocyclobutyl)acrylate<br><br>from tert-butyl (triphenyl-$\lambda^5$-phosphanylidene)-acetate and (3,3-difluorocyclobutyl)methanol [CAS Reg. No. 681128-39-2] | $^1$H-NMR (400 MHz, DMSO-d$_6$):<br>δ [ppm] = 1.42 (s, 9H), 2.48-2.64 (m, 2H, partially obscured by DMSO signal), 2.70-2.84 (m, 2H), 2.90-3.04 (m, 1H), 5.84 (d, 1H, $^3$J = 16.38 Hz), 6.88 (dd, 1H). |
| 3A | tert-butyl (2E)-3-(3,3-difluorocyclobutyl)acrylate<br><br>from tert-butyl (triphenyl-$\lambda^5$-phosphanylidene)-acetate and (3,3-difluorocyclobutyl)methanol [CAS Reg. No. 681128-39-2] | GC-MS (Method 6):<br>$R_t$ = 3.42 nun, m/z = 200 (M + NH$_4$)$^+$.<br>$^1$H-NMR (400 MHz, DMSO-d$_6$):<br>δ [ppm] = -0.04-0.02 (m, 2H), 0.33-0.40 (m, 2H), 0.63-0.75 (m, 1H), 1.34 (s, 9H), 1.94-2.00 (m, 2H), 5.69-5.76 (m, 1H), 6.69-6.79 (m, 1H). |

Example 4A and Example 5A

Methyl (2E/Z)-3-(3-amino-4-chlorophenyl)-4-methylpent-2-enoate and methyl 3-(3-amino-4-chlorophenyl)-4-methylpent-3-enoate Under argon, a mixture of 3.22 g (15.6 mmol) of 5-bromo-2-chloroaniline, 3.0 g (23.4 mmol) of methyl-(2E)-4-methylpent-2-enoate, 143 mg (0.16 mmol) of tris(dibenzylideneacetone)-dipalladium, 63 mg (0.31 mmol) of tri-tert-butylphosphine and 3.64 ml (17.2 mmol) of N,N-dicyclohexylmethylamine in 30 ml of dioxane were heated to 120° C. and stirred at this temperature for three days. Both after the first and after the second day of the reaction, the same amount of palladium catalyst and phosphine ligand was added to the reaction mixture. The reaction mixture was then filtered through Celite, and the filtrate was concentrated under reduced pressure. The residue was separated into its components by chromatography on silica gel (mobile phase cyclohexane/ethyl acetate 50:1). This gave 1.52 g of methyl (2E/Z)-3-(3-amino-4-chlorophenyl)-4-methylpent-2-enoate (38% of theory) and 906 mg of methyl 3-(3-amino-4-chlorophenyl)-4-methyl-pent-3-enoate (22% of theory).

Example 4A

Methyl (2E/Z)-3-(3-amino-4-chlorophenyl)-4-methylpent-2-enoate

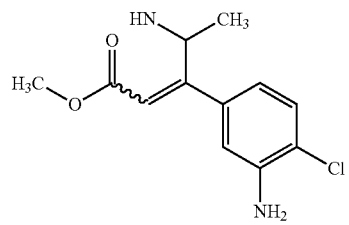 [SMILES: COC(=O)C=C(c1ccc(Cl)c(N)c1)C(C)N]

LC-MS (Method 2): $R_t$=2.46 min, m/z=254 (M+H)$^+$.

$^1$H-NMR (400 MHz, DMSO-d$_6$): δ [ppm]=1.03 (d, 6H), 3.65 (s, 3H), 3.90-4.03 (m, 1H), 5.42 (br. s, 2H), 5.63 (s, 1H), 6.40 (dd, 1H), 6.69 (d, 1H), 7.16 (d, 1H).

Example 5A

Methyl 3-(3-amino-4-chlorophenyl)-4-methylpent-3-enoate

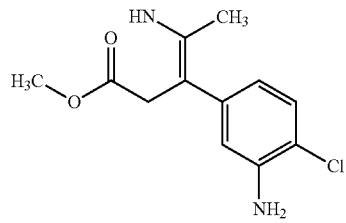 [SMILES: COC(=O)C/C(=C(/C)N)c1ccc(Cl)c(N)c1]

LC-MS (Method 2): $R_t$=2.28 min, m/z=254 (M+H)$^+$.

The following compound was obtained analogously to Synthesis Example 4A/5A:

| Example | Name/Structure/Starting materials | Analytical data |
|---|---|---|
| 6A | tert-butyl (2E/Z)-3-(3-amino-4-chlorophenyl)-4-methoxy-4-methylpent-2-enoate<br>from tert-butyl (2E/Z)-4-methoxy-4-methylpent-2-enoate and 5-bromo-2-chloroaniline | LC-MS (Method 5):<br>$R_t$ = 1.25 min, m/z, = 326/328 (M + H)$^+$. |

Example 7A tert-Butyl (2E)-3-cyclobutylacrylate

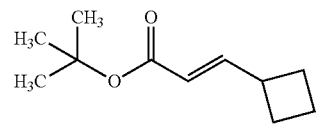

Step 1:

A solution of 11.1 ml (116.1 mmol) of oxalyl chloride in 50 ml of abs. dichloromethane was cooled to −78° C., and a solution of 16.5 ml (232.2 mmol) of DMSO in 50 ml of abs. dichloromethane was added dropwise, keeping the temperature below −50° C. After 5 min, a solution of 10.0 g (116.1 mmol) of cyclobutanemethanol in 20 ml of abs. dichloromethane was added dropwise. After a further 15 min of stirring at −78° C., 80.9 ml (580.5 mmol) of triethylamine were added. After 5 min, cooling was removed and the mixture was slowly warmed to RT, and the reaction mixture was then added to water. The mixture was saturated with sodium chloride and the separated organic phase was washed twice with saturated sodium chloride solution, three times with 1 N hydrochloric acid and three times with pH buffer solution, dried over sodium sulphate and concentrated under reduced pressure (500 mbar). This gave 6.28 g of cyclobutanecarbaldehyde as a crude product which was directly reacted further.

Step 2:

6.4 ml (27.3 mmol) of tert-butyl (diethoxyphosphoryl)acetate were added dropwise to a suspension, cooled to 0° C., of 1.05 g (60% in mineral oil, 26.2 mmol) of sodium hydride in a mixture of 22 ml of THF and 22 ml of DMF. After 30 min, the mixture was cooled to −10° C., and 2.0 g (crude, about 23.8 mmol) of cyclobutanecarbaldehyde were added in several portions. The reaction mixture was stirred at 0° C. for 5 h and then slowly warmed to RT overnight, subsequently added to water and extracted three times with ethyl acetate. The organic phases were combined and concentrated under reduced pressure. The residue was purified by chromatography on silica gel (mobile phase cyclohexane/ethyl acetate 50:1). This gave 1.21 g of the target product (about 28% of theory).

GC-MS (Method 1): $R_t$=3.26 min; m/z=126 $(M-C_4H_8)^+$.

$^1$H-NMR (400 MHz, DMSO-$d_6$): δ [ppm]=1.42 (s, 9H), 1.74-1.96 (m, 4H), 2.05-2.17 (m, 2H), 3.03-3.16 (m, 1H), 5.66 (dd, 1H), 6.86 (dd, 1H).

Example 8A and Example 9A tert-Butyl 3-(3-amino-4-chlorophenyl)-3-cyclobutylacrylate and tert-butyl 3-(3-amino-4-chlorophenyl)-3-cyclobutylidenepropanoate 0.78 ml (5.60 mmol) of triethylamine was added to a mixture of 385.2 mg (1.87 mmol) of 5-bromo-2-chloroaniline and 510 mg (2.80 mmol) of tert-butyl (2E)-3-cyclobutylacrylate in 2.8 ml of DMF. The mixture was evacuated three times and in each case vented with argon. After the addition of 41.9 mg (0.187 mmol) of palladium(II) acetate and 113.6 mg (0.373 mmol) of tri-2-tolylphosphine, the reaction mixture was evacuated two more times and in each case vented with argon and then stirred at 150° C. for 3 h. A further 193 mg of 5-bromo-2-chloroaniline were then added, and the reaction mixture was stirred at 150° C. for another 1 h. After cooling, the reaction mixture was filtered through Celite and the filter residue was washed twice with DMF. The combined filtrate was concentrated under high vacuum, and by chromatography on silica gel (mobile phase cyclohexane/ethyl acetate 60:1) the two isomeric target products were isolated from the residue. This gave 203 mg of tert-butyl 3-(3-amino-4-chlorophenyl)-3-cyclobutylacrylate (35.4% of theory) and 137 mg of tort-butyl 3-(3-amino-4-chlorophenyl)-3-cyclobutylidenepropanoate (23.8% of theory).

Example 8A tert-Butyl 3-(3-amino-4-chlorophenyl)-3-cyclobutylacrylate

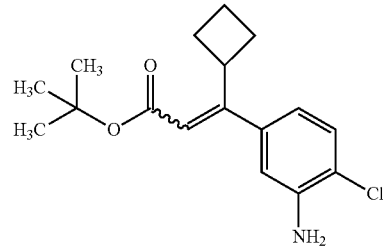 [SMILES: CC(C)(C)OC(=O)C=C(c1ccc(Cl)c(N)c1)C1CCC1]

LC-MS (Method 5): $R_t$=1.36 min, m/z=308 $(M+H)^+$.

$^1$H-NMR (400 MHz, DMSO-$d_6$): δ [ppm]=1.45 (s, 9H), 1.52-1.63 (m, 1H), 1.74-1.85 (m, 3H), 2.09-2.18 (m, 2H), 4.10 (quin, 1H), 5.35-5.41 (m, 2H), 5.55 (d, 1H), 6.38 (dd, 1H), 6.66 (d, 1H), 7.16 (d, 1H).

Example 9A tert-Butyl 3-(3-amino-4-chlorophenyl)-3-cyclobutylidenepropanoate

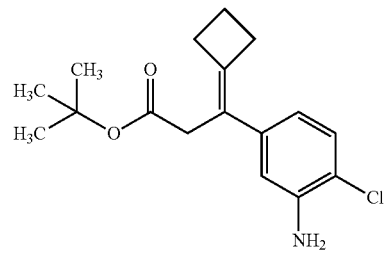 [SMILES: CC(C)(C)OC(=O)CC(=C1CCC1)c1ccc(Cl)c(N)c1]

LC-MS (Method 5): $R_t$=1.27 min, m/z=252 $(M+H-C_4H_8)^+$.

$^1$H-NMR (400 MHz, DMSO-$d_6$): δ [ppm]=1.31 (s, 9H), 1.93 (quin, 2H), 2.72-2.86 (m, 4H), 3.12 (s, 2H), 5.18-5.24 (m, 2H), 6.42 (dd, 1H), 6.69 (d, 1H), 7.06-7.11 (m, 1H).

The following compounds were obtained analogously to Synthesis Example 8A/9A:

| Example | Name/Structure/Starting materials | Analytical data |
| --- | --- | --- |
| 10A | tert-butyl (2E/Z)-3-(3-amino-4-chlorophenyl)-3-(3,3-difluorocyclobutyl)acrylate<br><br>from tert-butyl (2E)-3-(3,3-difluorocyclobutyl)-acrylate and 5-bromo-2-chloroaniline | $^1$H-NMR (400 MHz, DMSO-$d_6$): δ [ppm] = 1.46 (s, 9H), 2.23-2.41 (m, 2H), 2.77-2.90 (m, 2H), 3.88-4.01 (m, 1H), 5.45 (br. s, 2H), 5.73 (d, 1H), 6.41 (dd, 1H), 6.66 (d, 1H), 7 19 (d, 1H). LC-MS (Method 7): $R_t$ = 1.37 min, m/z = 344 $(M + H)^+$. |

| Example | Name/Structure/Starting materials | Analytical data |
|---|---|---|
| 11A | tert-butyl 3-(3-amino-4-chlorophenyl)-3-(3,3-difluorocyclobutylidene)propanoate<br><br>from tert-butyl (2E)-3-(3,3-difluorocyclobutyl)-acrylate and 5-bromo-2-chloroaniline | $^1$H-NMR (400 MHz, DMSO-$d_6$): δ [ppm] =1.31 (s, 9H), 3.24 (s, 2H), 3.32-3.47 (m, 4H, partially obscured by H$_2$O signal), 5.30 (br. s, 2H), 6.46 (dd, 1H), 6.74 (d, 1H), 7.13 (d, 1H).<br>LC-MS (Method 7): $R_t$ = 1.28 min, m/z = 344 (M + H)$^+$. |
| 12A | tert-butyl (2E/Z)-3-(3-amino-4-chlorophenyl)-4-cyclopropylbut-2-eonate<br><br>from tert-butyl (2E)-3-4-cyclopropylbut-2-eonate and 5-bromo-2-chloroaniline | $^1$H-NMR (400 MHz, DMSO-$d_6$): δ [ppm] = 0.05-0.11 (m, 2H), 0.27-0.34 (m, 2H), 0.64-0.75 (m, 1H), 1.45 (s, 9H), 2.91 (d, 2H), 5.42 (br. s, 2H), 5.84 (s, 1H), 6.70 (dd, 1H), 6.96 (d, 1H), 7 19 (d, 1H).<br>LC-MS (Method 5): $R_t$= 1.35 min, m/z = 308 (M + H)$^+$. |

Example 13A

Methyl 3-(3-amino-4-chlorophenyl)-4-methylpentanoate

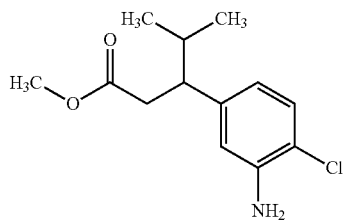 [SMILES: COC(=O)CC(c1ccc(Cl)c(N)c1)C(C)C]

At RT, a solution of 6.77 g (26.7 mmol) of methyl 2E/Z)-3-(3-amino-4-chlorophenyl)-4-methylpent-2-enoate in 130 ml of methanol was added to 2.2 g (90.7 mmol) of magnesium turnings and a few grains of iodine. After about 30 min, the internal temperature increased to about 60° C. After the reaction solution had cooled to room temperature, stirring at room temperature was continued for another 2 h. 50 ml of saturated aqueous ammonium chloride solution were then added slowly to the dark reaction mixture, and the mixture was extracted repeatedly with diethyl ether. The combined organic phases were washed with saturated sodium bicarbonate solution and saturated sodium chloride solution, dried over magnesium sulphate and concentrated under reduced pressure. The residue obtained was purified by chromatography on silica gel (mobile phase cyclohexane/ethyl acetate 10:1). This gave 2.95 g (40% of theory) of the title compound as an oil.

LC-MS (Method 5): $R_t$=1.06 min; m/z=256 (M+H)$^+$.

$^1$H-NMR (400 MHz, DMSO-$d_6$): δ [ppm]=0.69 (d, 3H), 0.87 (d, 3H), 1.67-1.80 (m, 1H), 2.44-2.56 (m, 1H, obscured by DMSO signal), 2.57-2.66 (m, 1H), 2.69-2.77 (m, 1H), 3.46 (s, 3H), 5.15-5.26 (br. s, 2H), 6.35 (dd, 1H), 6.58 (d, 1H), 7.05 (d, 1H).

The following compounds were obtained analogously to Synthesis Example 13A:

| Example | Name/Structure/Starting materials | Analytical data |
|---|---|---|
| 14A | tert-butyl 3-(3-amino-4-chlorophenyl)-4-methoxy-4-methylpentanoate<br>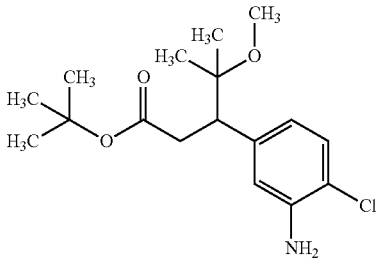<br>from tert-butyl (2E/Z)-3-(3-amino-4-chlorophenyl)-4-methoxy-4-methylpent-2-enoate | LC-MS (Method 7):<br>$R_t$ = 1.26 min, m/z = 328/330 $(M + H)^+$. |
| 15A | tert-butyl 3-(3-amino-4-chlorophenyl)-3-(3,3-difluorocyclobutyl)propanoate<br>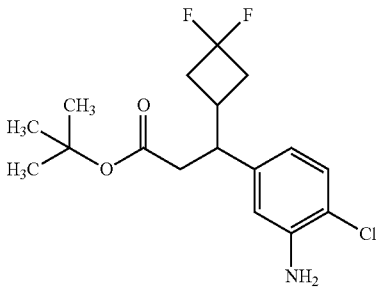<br>from tert-butyl (2E/Z)-3-(3-amino-4-chlorophenyl)-3-(3,3-difluorocyclobutyl)acrylate | $^1$H-NMR (400 MHz, DMSO-$d_6$):<br>δ [ppm] = 1.24 (s, 9H), 1.99-2.17 (m, 1H), 2.19-2.40 (m, 4H), 2.46-2.57 (m, 1H, partially obscured by DMSO signal), 2.59-2.72 (m, 1H), 2.72-2.83 (m, 1H), 5.24 (br s, 2H), 6.42 (dd, 1H), 6.63 (d, 1H), 7.07 (d, 1H).<br>LC-MS (Method 7):<br>$R_t$ = 1.28 min, m/z = 346 $(M + H)^+$. |
| 16A | tert-butyl 3-(3-amino-4-chlorophenyl)-4-cyclopropylbutanoate<br>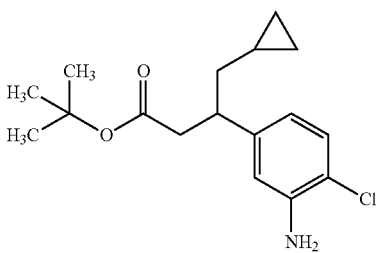<br>from tert-butyl (2E/Z)-3-(3-amino-4-chlorophenyl)-4-cyclopropylbut-2-enoate | LC-MS (Method 5):<br>$R_t$ = 1.32 min, m/z = 310 $(M + H)^+$. |

Example 17A and Example 18A

Methyl 3-(3-amino-4-chlorophenyl)-4-methylpentanoate (Enantiomers 1 and 2)

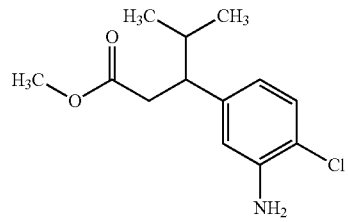 [SMILES: COC(=O)CC(c1ccc(Cl)c(N)c1)C(C)C]

By preparative HPLC on a chiral phase, 960 mg (3.75 mmol) of the racemate of methyl 3-(3-amino-4-chlorophenyl)-4-methylpentanoate (Example 13A) were separated into the enantiomers [column: Daicel Chiralpak AD-H, 5 µm, 250 mm×20 mm; mobile phase: isohexane/isopropanol 90:10 (v/v); flow rate: 20 ml/min; UV detection: 230 nm; temperature: 25° C.]:

Example 17A (Enantiomer 1):

Yield: 315 mg $R_t$=6.90 min; chemical purity >99%; >99% ee

[Column: Daicel AD-H, 5 µm, 250 mm×4 mm; mobile phase: isohexane/(isopropanol+0.2% diethylamine) 90:10 (v/v); flow rate: 1 ml/min; UV detection: 220 nm; temperature: 25° C.].

LC-MS (Method 8): $R_t$=2.34 min; m/z=256 (M+H)$^+$.

$^1$H-NMR (400 MHz, DMSO-d$_6$): δ [ppm]=0.69 (d, 3H), 0.87 (d, 3H), 1.67-1.80 (m, 1H), 2.44-2.56 (m, 1H, obscured by DMSO signal), 2.57-2.66 (m, 1H), 2.69-2.77 (m, 1H), 3.46 (s, 3H), 5.15-5.26 (br. s, 2H), 6.35 (dd, 1H), 6.58 (d, 1H), 7.05 (d, 1H).

Example 18A (Enantiomer 2):

Yield: 247 mg $R_t$=7.76 min; chemical purity >99%; >99% ee

[Column: Daicel AD-H, 5 µm, 250 mm×4 mm; mobile phase: isohexane/(isopropanol+0.2% diethylamine) 90:10 (v/v); flow rate: 1 ml/min; UV detection: 220 nm; temperature: 25° C.].

LC-MS (Method 8): $R_t$=2.34 min; m/z=256 (M+H)$^+$.

$^1$H-NMR (400 MHz, DMSO-d$_6$): δ [ppm]=0.69 (d, 3H), 0.87 (d, 3H), 1.67-1.80 (m, 1H), 2.44-2.56 (m, 1H, obscured by DMSO signal), 2.57-2.66 (m, 1H), 2.69-2.77 (m, 1H), 3.46 (s, 3H), 5.15-5.26 (br. s, 2H), 6.35 (dd, 1H), 6.58 (d, 1H), 7.05 (d, 1H).

Example 19A

2-Chloro-5-iodo-N,N-bis(4-methoxybenzyl)aniline

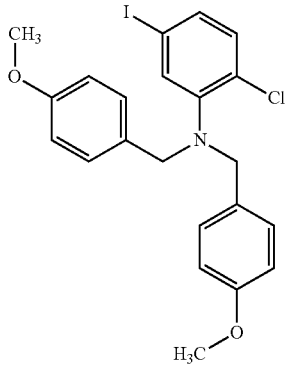 [SMILES: COc1ccc(CN(Cc2ccc(OC)cc2)c2cc(I)ccc2Cl)cc1]

Under argon, 12.62 g (316.16 mmol, 60% in mineral oil) of sodium hydride were suspended in 250 ml of abs. DMF and cooled to 0° C. 32 g (126.3 mmol) of 2-chloro-5-iodoaniline, dissolved in 80 ml of abs. DMF, were then slowly added dropwise, and the mixture was stirred at 0° C. for 30 min. 41 ml (303 mmol) of 1-(chloromethyl)-4-methoxybenzene were then slowly added to the reaction mixture, and the mixture was subsequently warmed to room temperature. The mixture was stirred at RT overnight and then carefully poured into 150 ml of ice-water. The organic phase was separated off, and the aqueous phase was then extracted three more times with diethyl ether. The combined organic phases were dried over magnesium sulphate. After filtration, the solvent was removed under reduced pressure. The crude product obtained was purified by chromatography on silica gel (mobile phase cyclohexane/ethyl acetate 40:1). This gave 59 g of the title compound (94% of theory).

LC-MS (Method 4): $R_t$=1.77 min; m/z=494/496 (M+H)$^+$.

$^1$H-NMR (400 MHz, DMSO-d$_6$): δ [ppm]=3.71 (s, 6H), 4.08 (s, 4H), 6.86 (d, 4H), 7.22 (d, 5H), 7.29-7.35 (m, 2H).

Example 20A

{3-[Bis(4-methoxybenzyl)amino]-4-chlorophenyl}(1-methylcyclopropyl)methanone

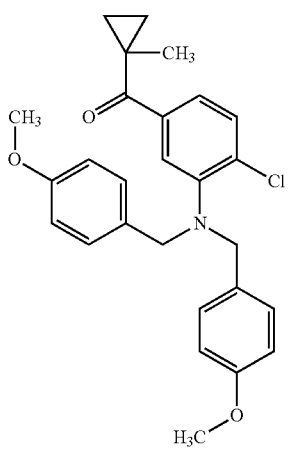 [SMILES: COc1ccc(CN(Cc2ccc(OC)cc2)c2cc(C(=O)C3(C)CC3)ccc2Cl)cc1]

Under argon, 7.587 g (15.37 mmol) of 2-chloro-5-iodo-N,N-bis(4-methoxybenzyl)aniline were dissolved in 100 ml of THF and cooled to −78° C. 7.65 ml (15.27 mmol) of a 2 M solution of isopropylmagnesium chloride in diethyl ether were then slowly added dropwise. The reaction solution was then slowly warmed to −40° C. and stirred at this temperature for 30 min. 2 g (13.97 mmol) of N-methoxy-N,1-dimethylcyclopropanecarboxamide [R. Shintani et al., *Chem. Eur. J.*, 15 (35), 8692-8694 (2009)], dissolved in 20 ml of THF, were then slowly added dropwise to the reaction solution. The reaction mixture obtained was then slowly warmed to room temperature and stirred at this temperature overnight. 50 ml of an ice-cold saturated aqueous ammonium chloride solution were then added to the reaction mixture. After separation of the phases, the aqueous phase was extracted three more times with ethyl acetate, and the combined organic phases were dried over magnesium sulphate, filtered and evaporated to dryness. The crude product obtained was purified chromatographically on silica gel (mobile phase cyclohexane/ethyl acetate 10:1). This gave 3.977 g (63% of theory) of the title compound.

LC-MS (Method 5): $R_t$=1.50 min; m/z=450/452 (M+H)$^+$.

$^1$H-NMR (400 MHz, DMSO-d$_6$): δ [ppm]=0.72-0.76 (m, 2H), 0.93-0.98 (m, 2H), 1.09 (s, 3H), 3.69 (s, 6H), 4.15 (s, 4H), 6.85 (d, 4H), 7.23 (d, 4H), 7.25-7.29 (m, 2H), 7.52-7.57 (m, 1H).

Example 21A tert-Butyl (2E/Z)-3-{3-[bis(4-methoxybenzyl)amino]-4-chlorophenyl}-3-(1-methylcyclopropyl)-acrylate

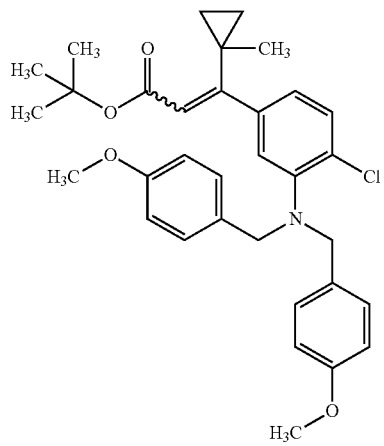 [SMILES: COc1ccc(CN(Cc2ccc(OC)cc2)c2cc(C(=CC(=O)OC(C)(C)C)C3(C)CC3)ccc2Cl)cc1]

0.84 ml (3.57 mmol) of tert-butyl (diethoxyphosphoryl)acetate was added dropwise to a suspension, cooled to 0° C., of 143 mg (60% in mineral oil, 3.57 mmol) of sodium hydride in 15 ml of THF. After 30 min, 1070 mg (2.38 mmol) of {3-[bis(4-methoxybenzyl)amino]-4-chlorophenyl}(1-methylcyclopropyl)methanone, dissolved in 10 nil of THF, were added. The cooling bath was removed, and the reaction mixture was stirred at RT overnight. 50 ml of an ice-cold saturated aqueous ammonium chloride solution were then added to the reaction mixture. After separation of the phases, the aqueous phase was extracted three more times with ethyl acetate, and the combined organic phases were dried over magnesium sulphate, filtered and evaporated to dryness. The residue was purified by chromatography on silica gel (mobile phase cyclohexane/ethyl acetate 50:1). This gave 960 mg of the target product as an E/Z isomer mixture (74% of theory).

LC-MS (Method 7): $R_t$=1.67 min (isomer 1), m/z=548/550 (M+H)$^+$; $R_t$=1.70 min (isomer 2), m/z=548/550 (M+H)+.

Example 22A tert-Butyl 3-{3-[bis(4-methoxybenzyl)amino]-4-chlorophenyl}-3-(1-methylcyclopropyl)-propanoate

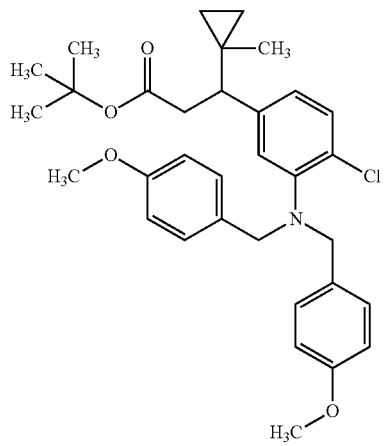 [SMILES: COc1ccc(CN(Cc2ccc(OC)cc2)c2cc(C(CC(=O)OC(C)(C)C)C3(C)CC3)ccc2Cl)cc1]

130 mg (1.58 mmol) of magnesium turnings and a few grains of iodine were initially charged, 865 mg (1.58 mmol) of tort-butyl (2E/Z)-3-{3-[bis(4-methoxybenzyl)amino]-4-chlorophenyl}-3-(1-methylcyclopropyl)acrylate in 10 ml of methanol were added and the mixture was stirred at room temperature. After about 10 min, there was a weak evolution of gas combined with a temperature increase. Using an ice bath, the temperature was kept at 35°–40° C. After the reaction had ended, 10 ml of a saturated aqueous ammonium chloride solution and 20 ml of dichloromethane were added to the reaction mixture. The organic phase was then separated off and the aqueous phase was extracted three more times with in each case about 10 ml of dichloromethane. The combined organic phases were dried over magnesium sulphate and concentrated under reduced pressure. The product was isolated from the residue by preparative RP-HPLC (mobile phase methanol/water 9:1 isocratic). This gave 159 mg of the target product (18% of theory).

LC-MS (Method 4): $R_t$=1.91 min; m/z=550/552 (M+H)$^+$.

Example 23A tert-Butyl 3-(3-amino-4-chlorophenyl)-3-(1-methylcyclopropyl)propanoate

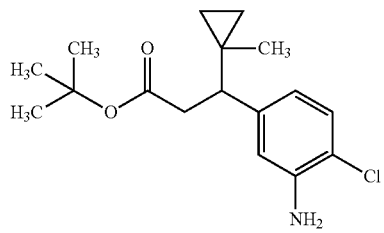 [SMILES: CC(C)(C)OC(=O)CC(c1ccc(Cl)c(N)c1)C1(C)CC1]

159 mg (0.29 mmol) of tert-butyl 3-{3-[bis(4-methoxybenzyl)amino]-4-chlorophenyl}-3-(1-methylcyclopropyl)propanoate were taken up in 7 ml of dichloromethane and 1.2 ml of water. 145 mg (0.64 mmol) of 2,3-dichloro-5,6-dicyano-1,4-benzoquinone (DDQ) were then added, and the reaction solution was stirred at room temperature for 2 h. The reaction mixture was then added to 10 ml of saturated aqueous sodium bicarbonate solution. The phases were separated, and the aqueous phase was then extracted three more times with in each case about 10 ml of dichloromethane. The combined organic phases were dried over magnesium sulphate and concentrated under reduced pressure. The product was isolated from the residue by preparative RP-HPLC (mobile phase methanol/water). This gave 31 mg of the target product (34% of theory).

LC-MS (Method 7): $R_t$=1.35 min; m/z=310 (M+H)$^+$.

Example 24A (4-Chloro-3-nitrophenyl)(cyclopropyl)methanone

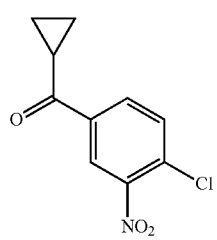 [SMILES: O=C(c1ccc(Cl)c([N+](=O)[O-])c1)C1CC1]

Under argon and at −10° C., 20 g (110.7 mmol) of (4-chlorophenyl)(cyclopropyl)methanone were added slowly to 60 ml of concentrated nitric acid. The reaction mixture was then slowly warmed to 5° C. and stirred at this temperature for 6 h. Carefully, the reaction solution was then added with stirring to about 100 ml of ice-water. This resulted in the precipitation of a white solid which was filtered off with suction and washed repeatedly with water. The solid obtained in this manner was then dried under high vacuum. This gave 24.3 g (97% of theory) of the desired product.

LC-MS (Method 7): $R_t$=1.06 min; m/z=224/226 (M−H)$^-$.

$^1$H-NMR (400 MHz, DMSO-d$_6$): δ [ppm]=1.05-1.18 (m, 4H), 2.92-3.02 (m, 1H), 7.97 (d, 1H), 8.32 (dd, 1H), 8.66 (d, 1H).

The following compound was obtained analogously to Synthesis Example 24A:

| Example | Name/Structure/Starting materials | Analytical data |
|---|---|---|
| 25A | (4-chloro-3-nitrophenyl)(1-fluorocyclopropyl)methanone<br>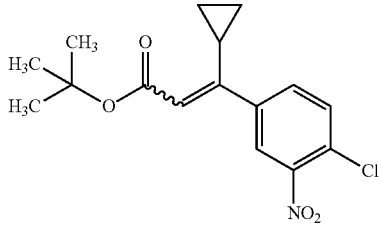<br>from (4-chlorophenyl)(1-fluorocyclopropyl)methanone [preparation according to DE 3704262-A1, Example (II-1)] | LC-MS (Method 7): $R_t$ = 1.11 min, m/z = 242 (M − H)$^-$. |

Example 26A tert-Butyl (2E/Z)-3-(4-chloro-3-nitrophenyl)-3-cyclopropylacrylate 13.5 ml (57.6 mmol) of tert-butyl (diethoxyphosphoryl)acetate were added dropwise to a suspension, cooled to 0° C., of 2.3 g (60% in mineral oil, 57.6 mmol) of sodium hydride in 50 ml of THF and 50 ml of DMF. After 30 min, 10 g (44.3 mmol) of (4-chloro-3-nitrophenyl)-(cyclopropyl)methanone were added a little at a time, the cooling bath was removed and the reaction mixture was stirred at RT overnight. 50 ml of an ice-cooled saturated aqueous ammonium chloride solution were then added to the reaction mixture. After separation of the phases, the aqueous phase was extracted three more times with ethyl acetate and the combined organic phases were dried over magnesium sulphate, filtered and concentrated to dryness. The residue was purified by chromatography on silica gel (mobile phase cyclohexane→cyclohexane/ethyl acetate 40:1). This gave 13.4 g of the target product as an E/Z isomer mixture (93% of theory).

MS (DCI): m/z=324 (M+H)$^+$, 341 (M+NH$_4$)$^+$.

$^1$H-NMR (400 MHz, DMSO-d$_6$): δ [ppm]=0.32-0.39 (m, 0.5H), 0.51-0.58 (m, 1.5H), 0.79-0.87 (m, 1.5H), 0.88-0.96 (m, 0.5H), 1.17 (s, 6.75H), 1.47 (s, 2.25H), 1.73-1.82 (m, 0.75H), 2.81-2.90 (m, 0.25H), 5.84 (s, 0.25H), 5.88 (s, 0.75H), 7.43 (dd, 0.75H), 7.59 (dd, 0.25H), 7.72-7.78 (m, 1H), 7.81 (d, 0.75H), 7.95 (d, 0.25H).

The following compounds were obtained analogously to Synthesis Example 26A:

| Example | Name/Structure/Starting materials | Analytical data |
|---|---|---|
| 27A | tert-butyl (2E/Z)-3-(4-chloro-3-nitrophenyl)-3-(1-fluorocyclopropyl)acrylate<br><br>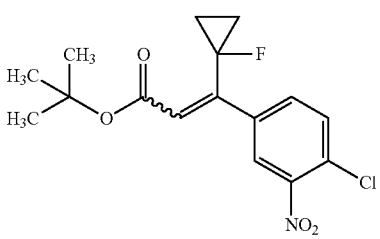<br><br>from (4-chloro-3-nitrophenyl)(1-fluorocyclopropyl)-methanone and tert-butyl (diethoxyphosphoryl)-acetate | MS (DCI): m/z = 359 (M + NH$_4$)$^+$.<br>$^1$H-NMR (400 MHz, DMSO-d$_6$): δ [ppm] = 1.01-1.10 (m, 2H), 1.19 (s, 7.74H), 1.31-1.41 (m, 2H), 1.51 (s, 1.26H), 6.13 (s, 0.86H), 6.77 (s, 0.14H), 7.55 (dd, 1H), 7.81 (d, 0.86H), 7.84 (d, 0.14H), 7.95 (d, 0.86H), 8.29 (d, 0.14H). |
| 28A | ehtyl (2E/Z)-3-(4-chloro-3-nitrophenyl)-3-cyclopropyl-2-methylacrylate<br><br>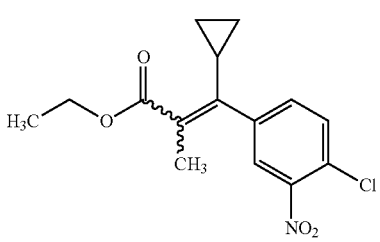<br><br>from (4-chloro-3-nitrophenyl)(cyclopropyl)-methanone and ethyl 2-(diethoxyphosphoryl)-propanoate | MS (DCI): m/z = 327 (M + NH$_4$)$^+$.<br>LC-MS (Method 7): R$_t$ = 1.26 min: m/z = 310 (M + H)$^+$. |

Example 29A tert-Butyl 3-(3-amino-4-chlorophenyl)-3-cyclopropylpropanoate

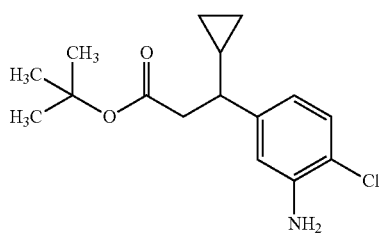 [SMILES: CC(C)(C)OC(=O)CC(c1ccc(Cl)c(N)c1)C1CC1]

200 mg (0.62 mmol) of tert-butyl (2E/Z)-3-(4-chloro-3-nitrophenyl)-3-cyclopropylacrylate were dissolved in 12 ml of ethyl acetate, and 20 mg (0.06 mmol) of platinum (10% on carbon) were added. The reaction mixture was stirred at RT under an atmosphere of hydrogen at atmospheric pressure for 12 hours. The reaction mixture was then filtered off with suction through kieselguhr, and the filtrate was concentrated. The crude product was purified by chromatography on silica gel (mobile phase cyclohexane/ethyl acetate 40:1). This gave 96 mg (52.1% of theory) of the target compound.

LC-MS (Method 5): R$_t$=1.24 min; m/z=296 (M+H)$^+$.

Example 30A and Example 31A tert-Butyl 3-(3-amino-4-chlorophenyl)-3-cyclopropylpropanoate (enantiomers 1 and 2)

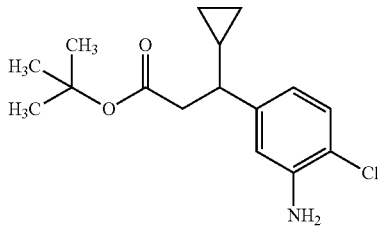 [SMILES: CC(C)(C)OC(=O)CC(c1ccc(Cl)c(N)c1)C1CC1]

By preparative HPLC on a chiral phase, 500 mg (1.69 mmol) of the racemate of tert-butyl 3-(3-amino-4-chlorophenyl)-3-cyclopropylpropanoate (Example 29A) were separated into the enantiomers [column: Daicel Chiralpak AZ-H, 5 µm, 250 mm×20 mm; mobile phase: iso-hexane/ethanol 90:10 (v/v); flow rate: 15 ml/min; UV detection: 220 nm; temperature: 30° C.]:

Example 30A (Enantiomer 1):
Yield: 237 mg
R$_t$=4.91 min; chemical purity >99%; >99% ee
[Column: Daicel AZ-H, 5 µm, 250 mm×4.6 mm; mobile phase: isohexane/ethanol 90:10 (v/v); flow rate: 1 ml/min; UV detection: 220 nm; temperature: 30° C.].

LC-MS (Method 5): $R_t$=1.23 min; m/z=296 (M+H)$^+$.

$^1$H-NMR (400 MHz, DMSO-$d_6$): δ [ppm]=0.02-0.10 (m, 1H), 0.16-0.25 (m, 1H), 0.27-0.36 (m, 1H), 0.45-0.54 (m, 1H), 0.85-0.98 (m, 1H), 1.28 (s, 9H), 2.02-2.11 (m, 1H), 2.43-2.62 (m, 2H, partially obscured by DMSO signal), 5.21 (br. s, 2H), 6.43 (dd, 1H), 6.64 (d, 1H), 7.06 (d, 1H).

$[α]_D^{20}$=−22.3°, c=0.465, Methanol.

Example 31A (Enantiomer 2):

Yield: 207 mg $R_t$=5.25 min; chemical purity >99%; >99% ee

[Column: Daicel AZ-H, 5 μm, 250 mm×4.6 mm; mobile phase: isohexane/ethanol 90:10 (v/v); flow rate: 1 ml/min; UV detection: 220 nm; temperature: 30° C.].

LC-MS (Method 5): $R_t$=1.23 min; m/z=296 (M+H)$^+$.

$^1$H-NMR (400 MHz, DMSO-$d_6$): δ [ppm]=0.02-0.10 (m, 1H), 0.16-0.25 (m, 1H), 0.27-0.36 (m, 1H), 0.45-0.54 (m, 1H), 0.85-0.98 (m, 1H), 1.28 (s, 9H), 2.02-2.11 (m, 1H), 2.43-2.62 (m, 2H, partially obscured by DMSO signal), 5.21 (br. s, 2H), 6.43 (dd, 1H), 6.64 (d, 1H), 7.06 (d, 1H).

$[α]_D^{20}$=+24.1°, c=0.330, methanol.

Example 32A tert-Butyl 3-(3-amino-4-chlorophenyl)-3-(1-fluorocyclopropyl)propanoate

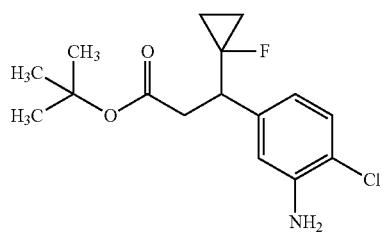 [SMILES: CC(C)(C)OC(=O)CC(c1ccc(Cl)c(N)c1)C1(F)CC1]

384 mg (1.12 mmol) of tert-butyl (2E/Z)-3-(4-chloro-3-nitrophenyl)-3-(1-fluorocyclopropyl)-acrylate were dissolved in 12 ml of ethyl acetate, and 38 mg (0.17 mmol) of platinum(IV) oxide were added. The reaction mixture was stirred at RT under an atmosphere of hydrogen at atmospheric pressure overnight. The reaction mixture was then filtered off with suction through kieselguhr and the filtrate was concentrated. The product was isolated from the residue by preparative RP-HPLC (mobile phase methanol/water). This gave 68 mg (19% of theory) of the target compound.

LC-MS (Method 7): $R_t$=1.24 min; m/z=314 (M+H)$^+$.

Example 33A (+/−)-tert-Butyl 3-(3-amino-4-chlorophenyl)-3-cyclobutylpropanoate

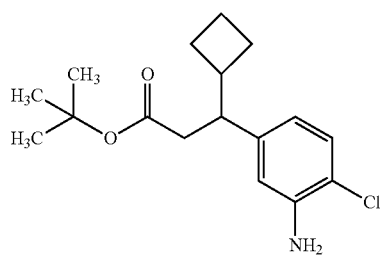 [SMILES: CC(C)(C)OC(=O)CC(c1ccc(Cl)c(N)c1)C1CCC1]

Method A:

133 mg (9.432 mmol) of tert-butyl 3-(3-amino-4-chlorophenyl)-3-cyclobutylidenepropanoate were dissolved in 20 ml of ethyl acetate. The solution was deoxygenated with argon, and 30 mg of 10% palladium on carbon were added. At RT, the reaction mixture was stirred under an atmosphere of hydrogen at atmospheric pressure overnight. The mixture was then filtered off through Celite, and the filtrate was concentrated under reduced pressure. The product was isolated from the residue by preparative RP-HPLC (mobile phase acetonitrile/water). This gave 67 mg of the target compound (50% of theory).

LC-MS (Method 5): $R_t$=1.31 min; m/z=310 (M+H)$^+$.

$^1$H-NMR (400 MHz, DMSO-$d_6$): δ [ppm]=1.24 (s, 9H), 1.47-1.57 (m, 1H), 1.57-1.77 (m, 4H), 1.94-2.05 (m, 1H), 2.19 (dd, 1H), 2.31-2.40 (m, 1H), 2.43 (dd, 1H), 2.71 (td, 1H), 5.13-5.22 (m, 2H), 6.36 (dd, 1H), 6.59 (d, 1H), 7.04 (d, 1H).

Method B:

At RT, a solution of 189 mg (0.614 mmol) of tert-butyl 3-(3-amino-4-chlorophenyl)-3-cyclobutylacrylate in 0.9 ml of methanol was added to 39 mg (1.60 mmol) of magnesium turnings and a few grains of iodine. The dark reaction mixture was stirred at RT overnight and then added to water and extracted with ethyl acetate. The organic phase was washed with saturated sodium bicarbonate solution and saturated sodium chloride solution, dried over magnesium sulphate and concentrated under reduced pressure. The product was isolated from the residue by preparative RP-HPLC. This gave 57.7 mg of the target compound (30.3% of theory).

Example 34A

Ethyl (2E/Z)-3-(3-amino-4-chlorophenyl)-3-cyclopropyl-2-methylacrylate

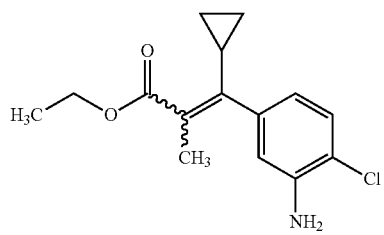

Under argon, 2.53 g (8.17 mmol) of ethyl (2E/Z)-3-(4-chloro-3-nitrophenyl)-3-cyclopropyl-2-methylacrylate were dissolved in 10 ml of dioxane, and 9.22 g (40.84 mmol) of tin(II) chloride dihydrate were added. The reaction mixture was then heated to 70° C. and stirred at this temperature overnight. After cooling to room temperature, about 20 ml of ethyl acetate were added and the reaction mixture was then added to about 20 ml of a 10% strength aqueous potassium fluoride solution. The resulting mixture was stirred vigorously for 10 min. The phases were separated, and the aqueous phase was then extracted two more times with in each case 10 ml of ethyl acetate. The combined organic phases were washed with about 50 ml of a saturated sodium chloride solution, dried over magnesium sulphate and concentrated under reduced pressure. This gave 2.2 g (96% of theory) of the target compound which was used without further purification for the next step.

LC-MS (Method 7): $R_t$=1.19 min; m/z=280/282 (M+H)$^+$.

Example 35A

Ethyl 3-(3-amino-4-chlorophenyl)-3-cyclopropyl-2-methyl-propanoate (Diastereomer Mixture)

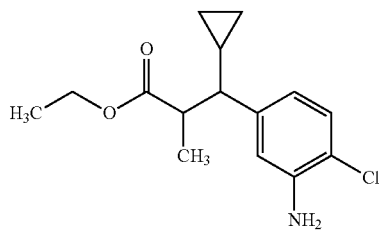 [SMILES: CCOC(=O)C(C)C(c1ccc(Cl)c(N)c1)C1CC1]

Under argon and at RT, a solution of 2.2 g (7.86 mmol) of ethyl (2E/Z)-3-(3-amino-4-chlorophenyl)-3-cyclopropyl-2-methylacrylate in 20 ml of methanol was added to 497 mg (20.45 mmol) of magnesium turnings and a few grains of iodine. The dark reaction mixture was stirred at RT overnight and then allowed to stand under argon for two days. The reaction solution was then diluted with ethyl acetate, and 1 M hydrochloric acid was added. The mixture was stirred for 5 min and then adjusted to pH 8-9 using saturated sodium bicarbonate solution. The organic phase was separated off, and the aqueous phase was extracted two more times with ethyl acetate. The combined organic phases were washed with saturated sodium chloride solution, dried over magnesium sulphate and concentrated under reduced pressure. The crude product was purified by chromatography on silica gel (mobile phase cyclohexane/ethyl acetate 100:1→50:1→20:1). This gave 1.38 g (62% of theory) of the target compound.

LC-MS (Method 5): $R_t$=1.13 min; m/z=282/284 $(M+H)^+$.

Example 36A

Dimethyl (3-methylbutan-2-ylidene)malonate

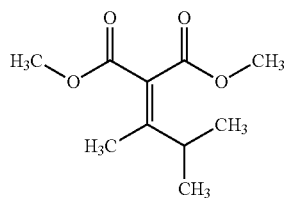

Under argon and at 0° C., 10 g (75.7 mmol) of dimethyl malonate in 20 ml of chloroform were slowly added dropwise to a solution of 16.6 ml (151.4 mmol) of titanium tetrachloride in 60 ml of chloroform. After the addition had ended, the reaction solution was stirred at 0° C. for another 30 min. At 0° C., 6.52 g (75.7 mmol) of 3-methyl-2-butanone in 20 ml of chloroform were then added dropwise. The reaction mixture was slowly warmed to room temperature and stirred at this temperature for 4 h. The reaction solution was then once more cooled to 0° C., and 30.6 ml (378.5 mmol) of pyridine in 20 ml of chloroform were added. After the addition had ended, the solution was warmed to room temperature and stirred at this temperature overnight. The reaction solution was then once more cooled to 0° C., and 50 ml of water were added slowly. The resulting phases were separated, and the aqueous phase was extracted two more times with in each case about 50 ml of dichloromethane. The combined organic phases were washed with saturated sodium bicarbonate solution and with saturated sodium chloride solution, dried over magnesium sulphate and concentrated under reduced pressure. The crude product was purified by chromatography on silica gel (mobile phase cyclohexane/ethyl acetate 20:1). This gave 9.4 g (62% of theory) of the target compound.

GC-MS (Method 1): $R_t$=3.57 min; m/z=185 $(M-CH_3)^+$.

$^1$H-NMR (400 MHz, DMSO-$d_6$): δ [ppm]=1.00 (d, 6H), 1.92 (s, 3H), 2.86-2.98 (m, 1H), 3.67 (s, 3H), 3.69 (s, 3H).

The following compounds were obtained analogously to Synthesis Example 36A:

| Example | Name/Structure/Starting materials | Analytical data |
|---|---|---|
| 37A | dimethyl (1-cyclobutylethylidene) malonate<br><br>from dimethyl malonate and 1-cyclobutylethanone | MS (DCI): m/z = 213 $(M + H)^+$.<br>$^1$H-NMR (400 MHz, DMSO-$d_6$):<br>δ [ppm] = 1.64-1.77 (m, 1H), 1.79-1.93 (m, 1H), 1.94-2.09 (m, 4H), 2.03 (s, 3H), 3.43-3.55 (m, 1H), 3.66 (s, 3H), 3.68 (s, 3H). |
| 38A | dimethyl (1-cyclopropylethylidene) malonate<br><br>from dimethyl malonate and 1-cyclopropyl-ethanone | GC-MS (Method 1):<br>$R_t$ = 4.36 min; m/z = 198 $(M)^+$.<br>$^1$H-NMR (400 MHz, DMSO-$d_6$):<br>δ [ppm] = 0.83-0.89 (m, 4H), 1.62 (s, 3H), 2.10-2.20 (m, 1H), 3.67 (s, 3H), 3.70 (s, 3H). |

Example 39A

Dimethyl [2-(4-chlorophenyl)-3-methylbutan-2-yl]malonate

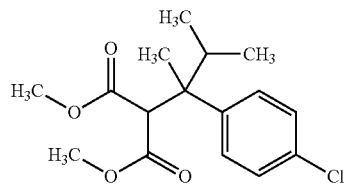 [SMILES: COC(=O)C(C(=O)OC)C(C)(c1ccc(Cl)cc1)C(C)C]

Under argon, 6.2 g (26 mmol) of 1-chloro-4-iodobenzene were dissolved in 50 ml of THF and cooled to −78° C. 24 ml (31.2 mmol) of a 1.3 M solution of isopropylmagnesium chloride x lithium chloride in THF were then slowly added dropwise. The reaction solution was then slowly warmed to −40° C. and stirred at this temperature for 2 h. The reaction solution was then warmed to −10° C., and 495 mg (2.6 mmol) of copper(I) iodide were added. 5 g (24.97 mmol) of dimethyl (3-methylbutan-2-ylidene)malonate, dissolved in 30 ml of THF, were then slowly added dropwise to the reaction solution. The resulting reaction mixture was slowly warmed to room temperature and stirred at this temperature for 1 h. The mixture was then cooled to 0° C., and ice-cold 1 M hydrochloric acid (pH ~2) was added carefully. The phases were separated, the aqueous phase was then extracted three more times with ethyl acetate and the combined organic phases were dried over magnesium sulphate, filtered and concentrated to dryness. The resulting crude product was initially pre-purified chromatographically on silica gel (mobile phase cyclohexane/ethyl acetate 20:1). The product was then re-purified by preparative RP-HPLC (mobile phase methanol/water). This gave 3.38 g (42% of theory) of the target compound.

$^1$H-NMR (400 MHz, DMSO-$d_6$): δ [ppm]=0.63-0.71 (m, 6H), 1.52 (s, 3H), 2.11-2.24 (m, 1H), 3.43 (s, 3H), 3.63 (s, 3H), 4.31 (s, 1H), 7.29-7.38 (m, 4H).

The following compounds were obtained analogously to Synthesis Example 39A:

Example 42A

Dimethyl [1-(3-amino-4-chlorophenyl)-1-cyclopropylethyl]malonate

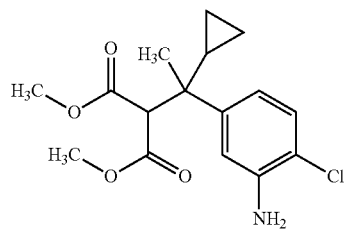 [SMILES: COC(=O)C(C(=O)OC)C(C)(c1ccc(Cl)c(N)c1)C1CC1]

| Example | Name/Structure/Starting materials | Analytical data |
|---|---|---|
| 40A | dimethyl [1-(4-chlorophenyl)-1-cyclobutylethyl]malonate<br>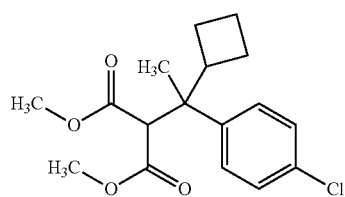<br>from 1-chloro-4-iodobenzene and dimethyl (1-cyclobutylethylidene)malonate | $^1$H-NMR (400 MHz, DMSO-$d_6$):<br>δ [ppm] = 1.34-1.49 (m, 3H), 1.53 (s, 3H), 1.55-1.65 (m, 2H), 1.66-1.76 (m, 1H), 2.79-2.91 (m, 1H), 3.38 (s, 3H), 3.66 (s, 3H), 4.07 (s, 1H), 7.35 (q, 4H). |
| 41A | dimethyl (1-{3-[bis(4-methoxybenzyl)amino]-4-chlorophenyl}-1-cyclopropylethyl)malonate<br>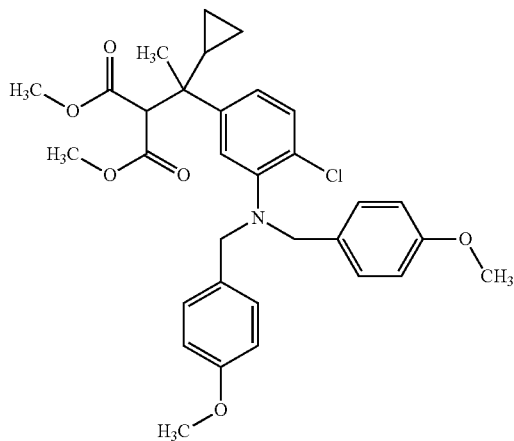<br>from 2-chloro-5-iodo-N,N-bis(4-methoxybenzyl)-aniline and dimethyl (1-cyclopropylethylidene)-malonate | LC-MS (Method 5):<br>$R_t$ = 1.53 min; m/z = 566/568 (M + H)$^+$.<br>$^1$H-NMR (400 MHz, DMSO-$d_6$):<br>δ [ppm] = -0.16-0.07 (m, 1H), 0.01-0.09 (m, 1H), 0.16-0.24 (m, 1H), 0.24-0.32 (m, 1H), 1.04 (s, 3H), 1.35-1 44 (m, 1H), 3.46 (s, 3H), 3.50 (s, 3H), 3.69 (s, 6H), 4.06 (s, 4H), 4.15 (s, 1H), 6.83 (d, 4H), 7.05 (dd, 1H), 7.10 (d, 1H), 7.21 (d, 4H), 7.28 (d, 1H). |

627 mg (1.11 mmol) of dimethyl (1-{3-[bis(4-methoxybenzyl)amino]-4-chlorophenyl}-1-cyclo-propylethyl)malonate were taken up in 60 ml of dichloromethane and 15 ml of water. 553 mg (2.44 mmol) of 2,3-dichloro-5,6-dicyano-1,4-benzoquinone (DDQ) were then added, and the reaction mixture was stirred at room temperature for 2 hours. The reaction mixture was then added to about 50 ml of saturated aqueous sodium bicarbonate solution. The phases were separated, and the aqueous phase was extracted three more times with in each case about 10 ml of dichloromethane. The combined organic phases were dried over magnesium sulphate and concentrated under reduced pressure. The product was isolated from the residue by preparative RP-HPLC (mobile phase methanol/water). This gave 283 mg of the target product (78% of theory).

LC-MS (Method 5): $R_t$=1.03 min; m/z=326/328 (M+H)$^+$.

$^1$H-NMR (400 MHz, DMSO-$d_6$): δ [ppm]=0.11-0.18 (m, 2H), 0.31-0.39 (m, 2H), 1.12 (s, 3H), 1.40-1.49 (m, 1H), 3.53 (s, 3H), 3.57 (s, 3H), 4.10 (s, 1H), 5.20 (s, 2H), 6.61 (dd, 1H), 6.91 (d, 1H), 7.05 (d, 1H).

Example 43A

Methyl 3-(4-chlorophenyl)-3,4-dimethylpentanoate

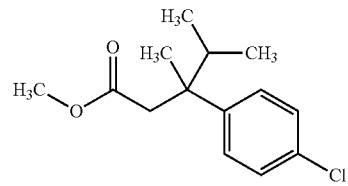 [SMILES: COC(=O)CC(C)(c1ccc(Cl)cc1)C(C)C]

3.38 g (10.81 mmol) of dimethyl [2-(4-chlorophenyl)-3-methylbutan-2-yl]malonate, 0.92 g (21.61 mmol) of lithium chloride and 0.2 ml of water in 10 ml of DMSO were heated under reflux for 4 h. After cooling, about 50 ml of diethyl ether were added to the reaction solution, and the phases were separated. The organic phase was washed twice with water, dried over magnesium sulphate and concentrated under reduced pressure. The crude product was purified by chromatography on silica gel (mobile phase cyclohexane/ethyl acetate 10:1). This gave 2.3 g (84% of theory) of the target compound.

GC-MS (Method 1): $R_t$=5.43 min; m/z=254 (M)$^+$.

$^1$H-NMR (400 MHz, DMSO-$d_6$): δ [ppm]=0.54 (d, 3H), 0.83 (d, 3H), 1.33 (s, 3H), 1.86-1.98 (m, 1H), 2.62 (d, 1H), 2.87 (d, 1H), 3.35 (s, 3H), 7.32 (s, 4H).

The following compounds were obtained analogously to Synthesis Example 43A:

| Example | Name/Structure/Starting material | Analytical data |
|---|---|---|
| 44A | methyl 3-(4-chlorophenyl)-3-cyclobutylbutanoate<br><br>from dimethyl [1-(4-chlorophenyl)-1-cyclobutylethyl]malonate | MS (DCI): m/z = 284 (M + NH$_4$)$^+$.<br>$^1$H-NMR (400 MHz, DMSO-$d_6$): δ [ppm] = 1.36 (s, 3H), 1.46-1.58 (m, 2H), 1.58-1.67 (m, 2H), 1.67-1.78 (m, 2H), 2.45-2.55 (m, 1H, partially obscured by DMSO signal), 2.55-2.64 (m, 1H), 2.81 (d, 1H), 3.41 (s, 3H), 7.28-7.35 (m, 4H). |
| 45A | methyl 3-(3-amino-4-chlorophenyl)-3-cyclopropylbutanoate<br><br>from dimethyl [1-(3-amino-4-chlorophenyl)-1-cyclopropylethyl]malonate | LC-MS (Method 7):<br>$R_t$ = 1.12 min; m/z = 268/270 (M + H)$^+$. |

Example 46A

Methyl 3-(4-chloro-3-nitrophenyl)-3,4-dimethylpentanoate

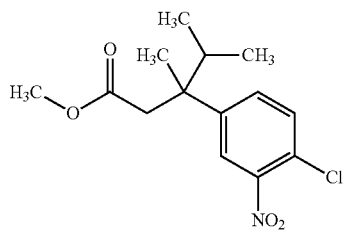 [SMILES: COC(=O)CC(C)(c1ccc(Cl)c([N+](=O)[O-])c1)C(C)C]

2.3 g (9.03 mmol) of methyl 3-(4-chlorophenyl)-3,4-dimethylpentanoate were dissolved in 50 ml of dichloromethane and cooled to 0° C. 1.44 g (10.8 mmol) of nitronium tetrafluoroborate were then added a little at a time. After the addition had ended, the reaction solution was initially stirred at 0°–10° C. for 1 h. The mixture was then slowly warmed to room temperature and stirred at this temperature for another 2 h. The reaction mixture was then added to about 50 ml of water, the phases were separated and the organic phase was dried over magnesium sulphate. The solution was concentrated by evaporation and the residue obtained was then purified by chromatography on silica gel (mobile phase cyclohexane/ethyl acetate 20:1). This gave 2.3 g (85% of theory) of the target compound.

MS (DCI): m/z=317 $(M+NH_4)^+$.

$^1$H-NMR (400 MHz, DMSO-$d_6$): δ [ppm]=0.56 (d, 3H), 0.84 (d, 3H), 1.35 (s, 3H), 1.89-2.02 (m, 1H), 2.66 (d, 1H), 3.02 (d, 1H), 3.39 (s, 3H), 7.63-7.71 (m, 2H), 7.96 (s, 1H).

The following compound was obtained analogously to Synthesis Example 46A:

Example 48A

Methyl 3-(3-amino-4-chlorophenyl)-3-cyclobutylbutanoate

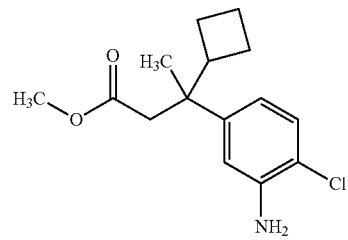 [SMILES: COC(=O)CC(C)(c1ccc(Cl)c(N)c1)C1CCC1]

1.79 g (5.74 mmol) of methyl 3-(4-chloro-3-nitrophenyl)-3-cyclobutylbutanoate were dissolved in 50 ml of ethyl acetate, and about 150 mg of 10% palladium on carbon were added. At RT, the reaction mixture was stirred vigorously under an atmosphere of hydrogen at atmospheric pressure overnight. The mixture was then filtered through Celite, and the filtrate obtained was evaporated to dryness. The crude product was purified by chromatography on silica gel (mobile phase cyclohexane/ethyl acetate 20:1). This gave 1.36 g of the target product (84% of theory).

LC-MS (Method 7): $R_t$=1.22 min; m/z=282 $(M+H)^+$.

$^1$H-NMR (400 MHz, DMSO-$d_6$): δ [ppm]=1.31 (s, 3H), 1.45-1.67 (m, 4H), 1.68-1.77 (m, 2H), 2.43 (d, 1H), 2.48-2.60 (m, 1H, partially obscured by DMSO signal), 2.66 (d, 1H), 3.43 (s, 3H), 5.16 (br. s, 2H), 6.47 (dd, 1H), 6.73 (d, 1H), 7.04 (d, 1H).

| Example | Name/Structure/Starting material | Analytical data |
| --- | --- | --- |
| 47A | methyl 3-(4-chloro-3-nitrophenyl)-3-cyclobutyl-butanoate<br><br>from methyl 3-(4-chlorophenyl)-3-cyclobutyl-butanoate | GC-MS (Method 6):<br>$R_t$ = 7.62 min; m/z = 329 $(M + NH_4)^+$.<br>$^1$H-NMR (400 MHz, DMSO-$d_6$):<br>δ [ppm] = 1.38 (s, 3H), 1.50-1.58 (m, 2H), 1.58-1.70 (m, 2H), 1.70-1.81 (m, 2H), 2.54 (d, 1H, partially obscured by DMSO signal), 2.57-2.66 (m, 1H), 2.95 (d, 1H), 3.44 (s, 3H), 7.62-7.70 (m, 2H), 7.94 (d, 1H). |

The following compound was obtained analogously to Synthesis Example 48A:

| Example | Name/Structure/Starting material | Analytical data |
|---------|----------------------------------|-----------------|
| 49A | methyl 3-(3-amino-4-chlorophenyl)-3,4-dimethyl-pentanoate<br><br>from methyl 3-(4-chloro-3-nitrophenyl)-3,4-dimethyl-pentanoate | LC-MS (Method 5): $R_t$ = 1.11 min; m/z = 270/272 (M + H)$^+$.<br>$^1$H-NMR (400 MHz, DMSO-$d_6$): δ [ppm] = 0.56 (d, 3H), 0.83 (d, 3H), 1.28 (s, 3H), 1.80-1.92 (m, 1H), 2.57 (d, 1H), 2.72 (d, 1H), 3.38 (s, 3H), 5.15 (br. s, 2H), 6.48 (dd, 1H), 6.73 (d, 1H), 7.04 (d, 1H). |

Example 50A and Example 51A

Methyl 3-(3-amino-4-chlorophenyl)-3,4-dimethylpentanoate (Enantiomers 1 and 2)

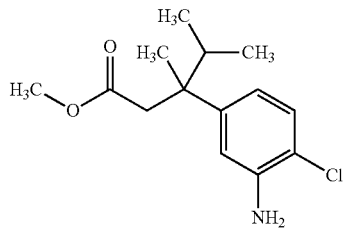

1700 mg (6.30 mmol) of the racemate of methyl 3-(3-amino-4-chlorophenyl)-3,4-dimethylpentanoate (Example 49A) were separated into the enantiomers by preparative HPLC on a chiral phase [column: Daicel Chiralpak AY-H, 5 μm, 250 mm×20 mm; mobile phase: isohexane/isopropanol 95:5 (v/v); flow rate: 20 ml/min; UV detection: 230 nm; temperature: 25° C.]. The material obtained in each case was re-purified by chromatography on silica gel (mobile phase cyclohexane/ethyl acetate 10:1).

Example 50A (Enantiomer 1):
Yield: 588 mg
$R_t$=7.21 min; chemical purity >99%; >99% ee
[Column: Daicel AY-H, 5 μm, 250 mm×4.6 mm; mobile phase: isohexane/(isopropanol+0.2% diethylamine) 95:5 (v/v); flow rate: 1 ml/min; UV detection: 230 nm; temperature: 30° C.].
LC-MS (Method 5): $R_t$=1.15 min; m/z=270 (M+H)$^+$.
$^1$H-NMR (400 MHz, DMSO-$d_6$): δ [ppm]=0.56 (d, 3H), 0.83 (d, 3H), 1.28 (s, 3H), 1.80-1.92 (m, 1H), 2.57 (d, 1H), 2.72 (d, 1H), 3.38 (s, 3H), 5.15 (br. s, 2H), 6.48 (dd, 1H), 6.73 (d, 1H), 7.04 (d, 1H).
$[α]_D^{20}$–30°, c=0.275, methanol.

Example 51A (Enantiomer 2):
Yield: 499 mg
$R_t$=8.59 min; chemical purity >99%; >96.7% ee
[Column: Daicel AY-H, 5 μm, 250 mm×4.6 mm; mobile phase: isohexane/(isopropanol+0.2% diethylamine) 95:5 (v/v); flow rate: 1 ml/min; UV detection: 230 nm; temperature: 30° C.].
LC-MS (Method 5): $R_t$=1.15 min; m/z=270 (M+H)$^+$.
$^1$H-NMR (400 MHz, DMSO-$d_6$): δ [ppm]=0.56 (d, 3H), 0.83 (d, 3H), 1.28 (s, 3H), 1.80-1.92 (m, 1H), 2.57 (d, 1H), 2.72 (d, 1H), 3.38 (s, 3H), 5.15 (br. s, 2H), 6.48 (dd, 1H), 6.73 (d, 1H), 7.04 (d, 1H).
$[α]_D^{20}$=+29°, c=0.270, methanol.

Example 52A and Example 53A

Methyl 3-(3-amino-4-chlorophenyl)-3-cyclobutylbutanoate (Enantiomers 1 and 2)

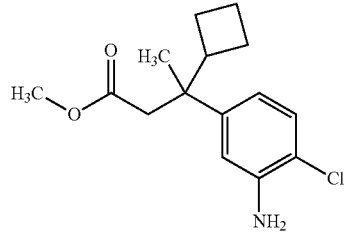 [SMILES: COC(=O)CC(C)(c1ccc(Cl)c(N)c1)C1CCC1]

1075 mg (3.82 mmol) of the racemate of methyl 3-(3-amino-4-chlorophenyl)-3-cyclobutylbutanoate (Example 48A) were separated into the enantiomers by preparative HPLC on a chiral phase [column: Daicel Chiralpak AY-H, 5 μm, 250 mm×20 mm; mobile phase: isohexane/ethanol 95:5 (v/v); flow rate: 15 ml/min; UV detection: 220 nm; temperature: 25° C.]:

Example 52A (Enantiomer 1):
Yield: 472 mg
$R_t$=6.40 min; chemical purity >99%; >99% ee
[Column: Daicel AY-H, 5 μm, 250 mm×4.6 mm; mobile phase: isohexane/(ethanol+0.2% diethylamine) 95:5 (v/v); flow rate: 1 ml/min; UV detection: 220 nm; temperature: 40° C.].
LC-MS (Method 5): $R_t$=1.15 min; m/z=282/284 (M+H)$^+$.
$^1$H-NMR (400 MHz, DMSO-$d_6$): δ [ppm]=1.31 (s, 3H), 1.45-1.67 (m, 4H), 1.68-1.78 (m, 2H), 2.43 (d, 1H), 2.48-2.60 (m, 1H, partially obscured by DMSO signal), 2.66 (d, 1H), 3.43 (s, 3H), 5.16 (br. s, 2H), 6.47 (dd, 1H), 6.73 (d, 1H), 7.04 (d, 1H).
$[α]_D^{20}$=–2.3°, c=0.450, methanol.

Example 53A (Enantiomer 2):
Yield: 489 mg
$R_t$=7.85 min; chemical purity >99%; >99% ee

[Column: Daicel AY-H, 5 μm, 250 mm×4.6 mm; mobile phase: isohexane/(ethanol+0.2% diethylamine) 95:5 (v/v); flow rate: 1 ml/min; UV detection: 220 nm; temperature: 40° C.].

$[\alpha]_D^{20}$=+2.5°, c=0.330, methanol.

Example 54A 1-(4-Chlorophenyl)prop-2-en-1-one

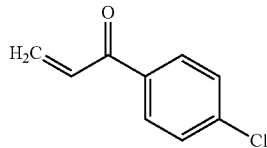

60 g (295.5 mmol) of 3-chloro-1-(4-chlorophenyl)propan-1-one were dissolved in 900 ml of acetonitrile. With ice bath cooling, 41.2 ml (295.5 mmol) of triethylamine were then slowly added dropwise to the solution (exothermal reaction). After the addition had ended, the reaction solution was stirred at room temperature for 4 h. About one litre of water, one litre of ethyl acetate and about 250 ml of saturated sodium chloride solution were then added to the reaction mixture. The phases were separated, the organic phase was then dried over magnesium sulphate and filtered and the filtrate was concentrated to dryness. The crude product obtained was purified by chromatography on silica gel (about 1.3 kg) (mobile phase cyclohexane/ethyl acetate 6:1). This gave 45 g of the target product (91% of theory).

$^1$H-NMR (400 MHz, DMSO-$d_6$): δ [ppm]=6.02 (d, 1H), 6.36 (dd, 1H), 7.34-7.44 (m, 1H), 7.63 (d, 1H), 8.03 (d, 2H).

Example 55A (4-Chlorophenyl)(2,2-difluorocyclopropyl)methanone

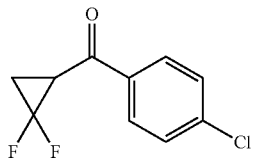 [SMILES: O=C(c1ccc(Cl)cc1)C1CC1(F)F]

Under argon, 91 g (546 mmol) of 1-(4-chlorophenyl)prop-2-en-1-one, 2.293 g (54.6 mmol) of sodium fluoride and 2.41 g (10.92 mmol) of 2,6-di-ten-butyl 4-methylphenol were heated in a 3 litre three-necked flask to 110° C. and stirred at this temperature for 5 min. At an internal temperature of 110°–125° C., 183 ml (928.5 mmol) of trimethylsilyl 2,2-difluoro-2-(fluorosulphonyl)acetate were then slowly added dropwise over a period of 30-35 min to the solution (careful: evolution of gas). After the addition and the evolution of gas had ended, the reaction solution was stirred for another 20 min. After cooling, the reaction mixture was taken up in several litres of ethyl acetate and extracted with saturated aqueous sodium bicarbonate solution. The phases were separated, the organic phase was then dried over magnesium sulphate and filtered and the filtrate was concentrated to dryness. The crude product obtained was purified by chromatography on silica gel (about 2 kg) (mobile phase cyclohexane/ethyl acetate 10:1). This gave 63 g of the target product (53% of theory).

$^1$H-NMR (400 MHz, DMSO-$d_6$): δ [ppm]=2.04-2.14 (m, 1H), 2.21-2.31 (m, 1H), 3.98-4.09 (m, 1H), 7.65-7.70 (m, 2H), 8.06-8.11 (m, 2H).

Example 56A

Methyl (2Z)-3-(4-chlorophenyl)-3-(2,2-difluorocyclopropyl)acrylate and methyl (2E)-3-(4-chlorophenyl)-3-(2,2-difluorocyclopropyl)acrylate

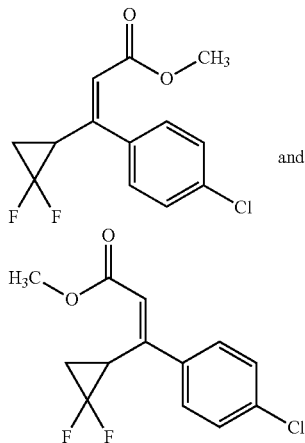

2.2 g (60% in mineral oil, 55 mmol) of sodium hydride were stirred with 20 ml of THF and then filtered off with suction, and the filtercake was washed with 20 ml of THF. Under argon, the sodium hydride purified in this manner was introduced into 200 ml of THF. The mixture was then cooled to 0° C., and 10.1 g (55 mmol) of methyl (diethoxyphosphoryl)acetate, dissolved in 10 ml of THF, were added. After warming to room temperature, the solution was stirred for another 1 h. 5.15 g (19.73 mmol) of (4-chlorophenyl)(2,2-difluorocyclopropyl)methanone in 50 ml of THF were then added dropwise. After the addition had ended, the solution was heated to reflux and stirred for 2 h. The solution was then cooled to 5° C., and the mixture was poured into 400 ml of ice-water. The phases were separated, and the aqueous phase was then extracted three more times with tert-butyl methyl ether. The combined organic phases were washed successively with 1 M hydrochloric acid and saturated sodium chloride solution, dried over sodium sulphate, filtered and concentrated to dryness. The crude product obtained was purified by chromatography on silica gel (mobile phase cyclohexane/ethyl acetate 20:1→8:1). The E/Z isomers were isolated in separated form. This gave 2.23 g (37% of theory) of methyl (2E)-3-(4-chlorophenyl)-3-(2,2-difluoro-cyclopropyl)acrylate and 1.6 g (24.4% of theory) of methyl (2Z)-3-(4-chlorophenyl)-3-(2,2-difluorocyclopropyl)acrylate.

Methyl (2E)-3-(4-chlorophenyl)-3-(2,2-difluorocyclopropyl)acrylate:

$^1$H-NMR (400 MHz, DMSO-$d_6$): δ [ppm]=1.00-1.12 (m, 1H), 1.92-2.06 (m, 1H), 3.21-3.37 (m, 1H, partially obscured by H$_2$O signal), 3.71 (s, 3H), 6.42 (d, 1H), 7.49 (d, 2H), 7.55 (d, 2H).

Methyl (2Z)-3-(4-chlorophenyl)-3-(2,2-difluorocyclopropyl)acrylate:

$^1$H-NMR (400 MHz, DMSO-$d_6$): δ [ppm]=1.83-1.96 (m, 1H), 1.97-2.09 (m, 1H), 2.76-2.88 (m, 1H), 3.51 (s, 3H), 6.10 (s, 1H), 7.23 (d, 2H), 7.46 (d, 2H).

Example 57A

Methyl 3-(4-chlorophenyl)-3-(2,2-difluorocyclopropyl)propanoate and methyl 3-(4-chlorophenyl)-5,5-difluorohexanoate

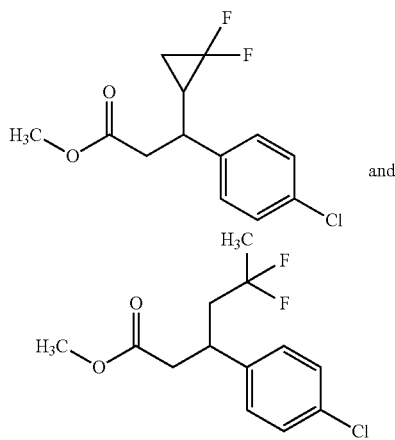

1000 mg (3.67 mmol) of methyl (2Z)-3-(4-chlorophenyl)-3-(2,2-difluorocyclopropyl)acrylate were dissolved in 75 ml of ethyl acetate and hydrogenated in a continuous-flow hydrogenation apparatus (H-Cube, from Thales Nano, Budapest) fitted with a catalyst cartridge (10% palladium on carbon) at a flow rate of 1 ml/min and at room temperature and atmospheric pressure using hydrogen. After the reaction had gone to completion, the reaction mixture was concentrated under reduced pressure. This gave 980 mg of a product mixture consisting of methyl 3-(4-chlorophenyl)-3-(2,2-difluoro-cyclopropyl)propanoate and methyl 3-(4-chlorophenyl)-5,5-difluorohexanoate as a colourless oil.

GC-MS (Method 6): $R_t$=5.38 min; m/z=292/294/296 $(M+NH_4)^+$.

Example 58A

Methyl 3-(4-chloro-3-nitrophenyl)-3-(2,2-difluorocyclopropyl)propanoate and methyl 3-(4-chloro-3-nitrophenyl)-5,5-difluorohexanoate

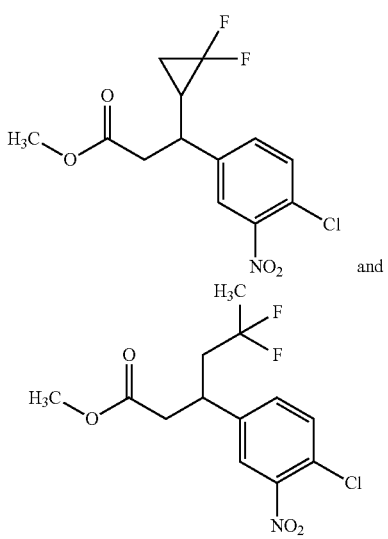

610 mg of the mixture consisting of methyl 3-(4-chlorophenyl)-3-(2,2-difluorocyclopropyl)-propanoate and methyl 3-(4-chlorophenyl)-5,5-difluorohexanoate (Example 57A) were dissolved in 12 ml of dichloromethane and cooled to 0° C. 351 mg (2.65 mmol) of nitroniumtetrafluoroborate were then added a little at a time. After the addition had ended, the reaction solution was stirred at 0°–10° C. for 1 h. The mixture was then slowly warmed to room temperature and stirred at this temperature for a further 2 h. The reaction mixture was then added to about 20 ml of water, the phases were separated and the organic phase was dried over magnesium sulphate. The solution was concentrated by evaporation and the residue obtained was then purified by chromatography on silica gel (mobile phase cyclohexane/ethyl acetate 20:1). This gave 637 mg of the mixture of the two target compounds.

GC-MS (Method 6): $R_t$=6.74 min; m/z=337/339/341 $(M+NH_4)^+$.

Example 59A

Methyl 3-(3-amino-4-chlorophenyl)-3-(2,2-difluorocyclopropyl)propanoate and methyl 3-(3-amino-4-chlorophenyl)-5,5-difluorohexanoate

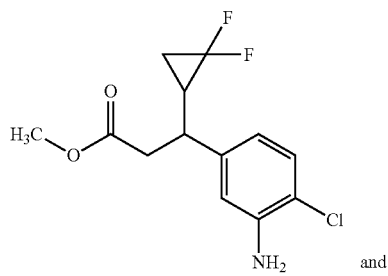

640 mg of the mixture consisting of methyl 3-(4-chloro-3-nitrophenyl)-3-(2,2-difluorocyclo-propyl)propanoate and methyl 3-(4-chloro-3-nitrophenyl)-5,5-difluorohexanoate (Example 58A) were dissolved in 40 ml of ethyl acetate, and 106 mg of palladium on carbon (10%) were added. The reaction mixture was stirred vigorously under an atmosphere of hydrogen at atmospheric pressure overnight. The mixture was then filtered through Celite, and the filtrate obtained was evaporated to dryness. The crude product was purified by chromatography on silica gel (mobile phase cyclohexane/ethyl acetate 4:1). This gave 361 mg of the mixture of the two target compounds.

LC-MS (Method 5): $R_t$=0.98 min; m/z=290/292 $(M+H)^+$.

Example 60A (+)-Ethyl (3R)-4,4,4-trifluoro-3-methylbutanoate

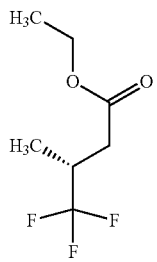

At room temperature, 133 ml (1.82 mol) of thionyl chloride were added slowly to 287 g (1.65 mol) of (3R)-4,4,4-trifluoro-3-methylbutanoic acid [A. Gerlach and U. Schulz, *Speciality Chemicals Magazine* 24 (4), 37-38 (2004); CAS Acc.-No. 142:179196] in 580 ml of ethanol. The reaction solution was then heated to 80° C. and stirred at this temperature for 2 h. The mixture was then cooled to room temperature, 250 ml of water were added slowly and the mixture was extracted three times with in each case 150 ml of tert-butyl methyl ether. The combined organic phases were dried over sodium sulphate. After filtration the solvent was removed under reduced pressure at 30° C. and a pressure of 300 mbar. The crude product was then distilled at 100 mbar and a head temperature of 65° C. This gave 225.8 g (113 mol, 74% of theory) of the title compound as a colourless liquid.

$^1$H-NMR (400 MHz, DMSO-$d_6$, δ/ppm): 4.10 (2H, q), 2.88-2.72 (1H, m), 2.66-2.57 (1H, m), 2.46-2.36 (1H, m), 1.19 (3H, t), 1.11 (3H, d).

GC-MS (Method 1): $R_t$=1.19 min; m/z=184 (M)$^+$.

$[α]_D^{20}$=+16.1°, c=0.41, methanol.

Example 61A

Ethyl 4,4,4-trifluoro-3-methyl-2-(4-methylphenyl)butanoate (Diastereomer Mixture)

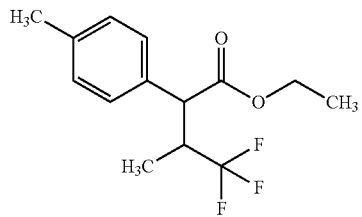 [SMILES: CCOC(=O)C(c1ccc(C)cc1)C(C)C(F)(F)F]

Under argon 196.9 mg (0.88 mmol) of palladium(II) acetate and 724.8 mg (1.84 mmol) of 2-dicyclohexylphosphino-2'-(N,N-dimethylamino)biphenyl were initially charged in 50 ml of anhydrous toluene. 43.8 ml (43.8 mmol) of a 1 M solution of lithium hexamethyldisilazide in THF were added slowly, and the reaction solution was then stirred at RT for 10 min. The reaction solution was then cooled to −10° C., 7 g (38.0 mmol) of (+/−)-ethyl 4,4,4-trifluoro-3-methylbutanoate were added slowly and the mixture was stirred at −10° C. for 10 min. 5 g (29.2 mmol) of 4-bromotoluene, dissolved in 50 ml of toluene, were then added dropwise, and the reaction solution was warmed first to RT and then heated to 80° C. The mixture was stirred at this temperature for 2 h and then cooled to RT and stirred overnight. After the reaction had ended (monitored by TLC; mobile phase cyclohexane/dichloromethane 2:1), the reaction mixture was filtered through kieselguhr, the residue was washed repeatedly with ethyl acetate and dichloromethane and the combined filtrates were concentrated under reduced pressure. The crude product obtained was purified chromatographically on silica gel (mobile phase petroleum ether/dichloromethane 4:1→3:1). This gave 3.91 g (14.3 mmol, 48.8% of theory) of the title compound as a colourless liquid.

$^1$H-NMR (400 MHz, DMSO-$d_6$, δ/ppm): 7.26 (2H, d), 7.20-7.12 (2H, m), 4.17-3.95 (2H, m), 3.74 (0.25H, d), 3.66 (0.75H, d), 3.35-3.07 (1H, m), 2.29 (2.25H, s), 2.28 (0.75H, s), 1.17 (0.75H, d), 1.11 (3H, t), 0.76 (2.25H, d).

GC-MS (Method 1): $R_t$=4.20 min, m/z=275 (M+H)$^+$ (diastereomer 1); $R_t$=4.23 min, m/z=275 (M+H)$^+$ (diastereomer 2).

Example 62A

Ethyl (3R)-4,4,4-trifluoro-3-methyl-2-(4-methylphenyl)butanoate (Diastereomer Mixture)

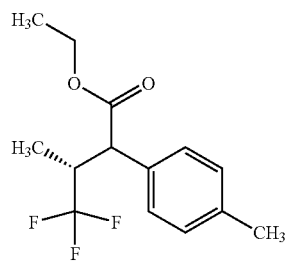 [SMILES: CCOC(=O)C(c1ccc(C)cc1)[C@@H](C)C(F)(F)F]

Preparation of solution A: Under argon, 16.3 ml of a 1 M solution of lithium hexamethyldisilazide in toluene were cooled to −10° C. to −20° C. (cooling with acetone/dry ice), and 2 g (10.86 mmol) of (+)-ethyl (3R)-4,4,4-trifluoro-3-methylbutanoate, dissolved in 10 ml of toluene, were added slowly; during the addition, it was made sure that a temperature of −10° C. was not exceeded. The solution was then stirred for another 10 min at at most −10° C.

Preparation of solution B: Under argon, 2.415 g (14.12 mmol) of 4-bromotoluene were dissolved at RT in 14 ml of toluene, and 73 mg (0.33 mmol) of palladium(II) acetate and 269 mg (0.68 mmol) of 2-dicyclohexylphosphino-2'-(N,N-dimethylamino)biphenyl were added. The solution was stirred at RT for 10 min.

First, the cooling bath was removed from solution A. Solution B was then slowly added dropwise to solution A, which was still cold. The combined solutions were then slowly warmed to RT and stirred at this temperature for 1 h. The reaction solution was then heated to 80° C. (internal temperature) and stirred at this temperature for 3 h. The reaction solution was then slowly cooled to RT and stirred for another 12 h. Finally, the reaction mixture was filtered through kieselguhr, the residue was washed repeatedly with toluene and the combined filtrates were concentrated under reduced pressure. The crude product obtained was purified chromatographically on silica gel (mobile phase cyclohexane/dichloromethane 10:1→4:1). This gave 2.35 g (79% of theory) of the title compound.

$^1$H-NMR (400 MHz, DMSO-$d_6$, δ/ppm): 0.76 (d, 2.13H), 1.11 (t, 3H), 1.17 (d, 0.87H), 3.07-3.30 (m, 1H), 3.66 (d, 0.7H), 3.75 (d, 0.3H), 3.94-4.15 (m, 2H), 7.12-7.20 (m, 2H), 7.23-7.29 (m, 2H).

GC-MS (Method 1): $R_t$=3.88 min, m/z=275 (M+H)$^+$ (diastereomer 1); $R_t$=3.90 min, m/z=275 (M+1-1)$^+$ (diastereomer 2).

Example 63A

Ethyl (3R)-2-(4-chlorophenyl)-4,4,4-trifluoro-3-methylbutanoate (Diastereomer Mixture)

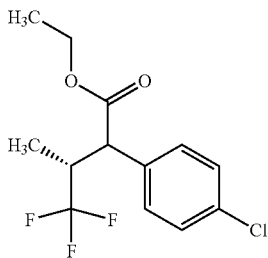 [SMILES: CCOC(=O)C(c1ccc(Cl)cc1)[C@@H](C)C(F)(F)F]

Preparation of solution A: Under argon, 163.9 ml of a 1 M solution of lithium hexamethyldisilazide in toluene were cooled to −10° C. to −20° C. (cooling using acetone/dry ice), and 20 g (108.6 mmol) of (+)-ethyl (3R)-4,4,4-trifluoro-3-methylbutanoate, dissolved in 150 ml of toluene, were added slowly; during the addition care was taken that a temperature of −10° C. was not exceeded. The solution was then stirred for another 10 min at at most −10° C.

Preparation of solution B: Under argon, 27.03 g (141.2 mmol) of 1-bromo-4-chlorobenzene were dissolved at RT in 100 ml of toluene, and 731 mg (3.26 mmol) of palladium(II) acetate and 2.693 g (6.84 mmol) of 2-dicyclohexylphosphino-2'-(N,N-dimethylamino)biphenyl were added. The solution was stirred at RT for 10 min.

First, the cooling bath was removed from solution A. Solution B was then slowly added dropwise to solution A, which was still cold. The combined solutions were then slowly warmed to RT and stirred at this temperature for 1 h. The reaction solution was then heated to 80° C. (internal temperature) and stirred at this temperature for 3 h. The reaction solution was then slowly cooled to RT and stirred for another 12 h. The reaction mixture was finally filtered through kieselguhr, the residue was washed repeatedly with toluene and the combined filtrates were concentrated under reduced pressure. The crude product obtained was purified chromatographically on silica gel (mobile phase cyclohexane/dichloromethane 4:1). This gave 27.4 g (92.98 mmol, 86% of theory) of the title compound as a yellow oil in a diastereomer ratio of 3:1.

GC-MS (Method 1): $R_t$=4.45 min, m/z=294 (M)$^+$ (diastereomer 1); $R_t$=4.48 min, m/z=294 (M)$^+$ (diastereomer 2).

The following compounds were obtained analogously to Synthesis Examples 61A and 63A:

| Example | Name/Structure/Starting materials | Analytical data |
|---|---|---|
| 64A | ethyl (3R)-4,4,4-trifluoro-2-(4-isopropylphenyl)-3-methylbutanoate<br><br>from 1-bromo-4-isopropylbenzene and ethyl (3R)-4,4,4-trifluoro-3-methylbutanoate | GC-MS (Method 1):<br>$R_t$ = 4.61 min, m/z = 302 (M)$^+$ (diastereomer 1);<br>$R_t$ = 4.64 min, m/z = 302 (M)$^+$ (diastereomer 2). |
| 65A | ethyl (3R)-2-(4-tert-butylphenyl)-4,4,4-trifluoro-3-methylbutanoate<br><br>from 1-bromo-4-tert-butylbenzene and ethyl (3R)-4,4,4-trifluoro-3-methylbutanoate | GC-MS (Method 1):<br>$R_t$ = 4.83 min, m/z = 317 (M + H)$^+$ (diastereomer 1);<br>$R_t$ = 4.85 min, m/z = 317 (M + H)$^+$ (diastereomer 2).<br>MS (DCI): m/z = 334 (M + NH$_4$)$^+$. |

| Example | Name/Structure/Starting materials | Analytical data |
|---|---|---|
| 66A | ethyl (3R)-2-(4-chloro-3-methoxyphenyl)-4,4,4-trifluoro-3-methylbutanoate<br>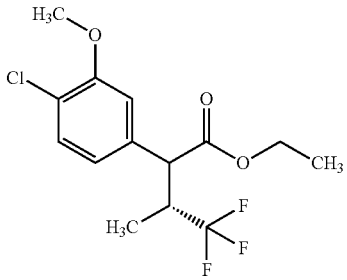<br>from 4-bromo-1-chloro-2-methoxybenzene and ethyl (3R)-4,4,4-trifluoro-3-methyl-butanoate | GC-MS (Method 1):<br>$R_t$ = 5.34 min; m/z = 324/326 $(M)^+$. |
| 67A | ethyl 2-(4-chloro-3-methylphenyl)-4,4,4-trifluoro-3-methylbutanoate<br>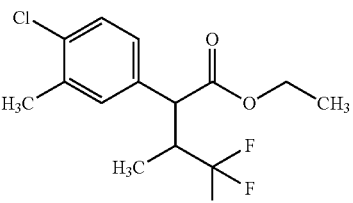<br>from 4-bromo-1-chloro-2-methylbenzene and ethyl 4,4,4-trifluoro-3-methylbutanoate | GC-MS (Method 1):<br>$R_t$ = 4.81 min/m/z = 308/310 $(M)^+$ (diastereomer 1);<br>$R_t$ = 4.84 min, m/z = 308/310 $(M)^+$ (diastereomer 2). |

Example 68A

Ethyl (3R)-2-(4-ethylphenyl)-4,4,4-trifluoro-3-methylbutanoate (Diastereomer Mixture)

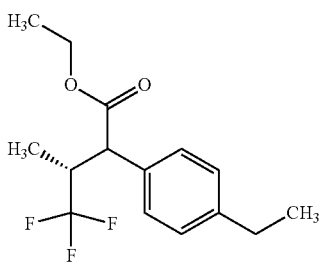 [SMILES: CCOC(=O)C(c1ccc(CC)cc1)[C@@H](C)C(F)(F)F]

24.4 ml (24.4 mmol) of a 1 M solution of lithium hexamethyldisilazide in toluene were cooled to −10° C., and a solution of 3.0 g (16.29 mmol) of (+)-ethyl (3R)-4,4,4-trifluoro-3-methylbutanoate in 15 ml of abs. toluene was added dropwise. The mixture was stirred for 10 min. At −10° C., a solution, prepared beforehand, of 3.92 g (21.18 mmol) of 1-bromo-4-ethylbenzene, 110 mg (0.49 mmol) of palladium(II) acetate and 404 mg (1.03 mmol) of 2'-dicyclohexylphosphino-2-(N,N-dimethylamino)biphenyl in 20 ml of abs. toluene was then added dropwise. The resulting reaction mixture was then stirred first at RT for 1 h and then at 80° C. for 3 h. The mixture was then concentrated under reduced pressure and the residue was taken up in ethyl acetate and added to water. The aqueous phase was re-extracted with ethyl acetate, and the combined organic phases were washed with saturated ammonium chloride solution and saturated sodium chloride solution, dried over magnesium sulphate and concentrated under reduced pressure. The residue gave, after chromatography on silica gel (mobile phase first cyclohexane, then gradient cyclohexane/ethyl acetate 200:1→50:1), 3.051 g of the title compound (64.9% of theory, diastereomer ratio about 3:1).

LC-MS (Method 4): $R_t$=1.52 min, m/z=289 $(M+H)^+$ (minor diastereomer); $R_t$=1.54 min, m/z=289 $(M+H)^+$ (major diastereomer).

$^1$H-NMR (400 MHz, DMSO-$d_6$): major diastereomer: δ [ppm]=0.76 (d, 3H), 1.13 (t, 3H), 1.17 (t, 3H), 2.55-2.63 (m, 2H), 3.21-3.31 (m, 1H), 3.67 (d, 1H), 3.95-4.16 (m, 2H), 7.15-7.23 (m, 2H), 7.25-7.31 (m, 2H).

The following compounds were prepared in a similar manner from (+)-ethyl (3R)-4,4,4-trifluoro-3-methylbutanoate and the appropriate phenyl bromides:

Example 69A

Ethyl (3R)-4,4,4-trifluoro-3-methyl-2-(4-vinylphenyl)butanoate (Diastereomer Mixture)

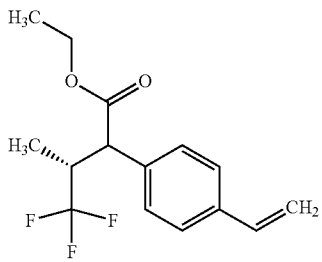 [SMILES: C=Cc1ccc(C(C(=O)OCC)[C@@H](C)C(F)(F)F)cc1]

GC-MS (Method 1): $R_t$=4.64 min and 4.66 min; in each case m/z=286 (M)$^+$.

$^1$H-NMR (400 MHz, DMSO-$d_6$): major diastereomer: δ [ppm]=0.79 (d, 3H), 1.12 (t, 3H), 3.22-3.32 (m, 1H), 3.73 (d, 1H), 3.99-4.17 (m, 2H), 5.28 (d, 1H), 5.84 (d, 1H), 6.72 (dd, 1H), 7.34-7.40 (m, 2H), 7.45-7.51 (m, 2H).

Example 70A

Ethyl (3R)-4,4,4-trifluoro-2-(4-fluorophenyl)-3-methylbutanoate (Diastereomer Mixture)

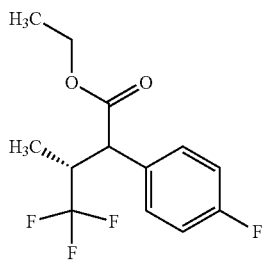 [SMILES: CCOC(=O)C(c1ccc(F)cc1)[C@@H](C)C(F)(F)F]

GC-MS (Method 1): $R_t$=3.63 min, m/z=278 (M)$^+$ (minor diastereomer); $R_t$=3.66 min, m/z=278 (M)$^+$ (major diastereomer).

$^1$H-NMR (400 MHz, DMSO-$d_6$): major diastereomer: δ [ppm]=0.77 (d, 3H), 1.12 (t, 3H), 3.23-3.30 (m, 1H), 3.79 (d, 1H), 4.01-4.14 (m, 2H), 7.19-7.24 (m, 2H), 7.43-7.47 (m, 2H).

Example 71A

Ethyl (3R)-2-(4-chloro-3-fluorophenyl)-4,4,4-trifluoro-3-methylbutanoate (Diastereomer Mixture)

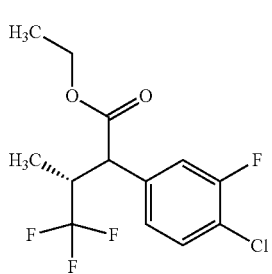 [SMILES: CCOC(=O)C(c1ccc(Cl)c(F)c1)[C@@H](C)C(F)(F)F]

GC-MS (Method 1): $R_t$=4.33 min and 4.36 min; in each case m/z=312 (M)$^+$.

$^1$H-NMR (400 MHz, DMSO-$d_6$): major diastereomer: δ [ppm]=0.80 (d, 3H), 1.08-1.19 (m, 3H), 3.34-3.41 (m, 1H), 3.88 (d, 1H), 4.01-4.18 (m, 2H), 7.28-7.34 (m, 1H), 7.51-7.64 (m, 2H).

Example 72A

Ethyl (3R)-2-[4-(2,2-difluorocyclopropyl)phenyl]-4,4,4-trifluoro-3-methylbutanoate

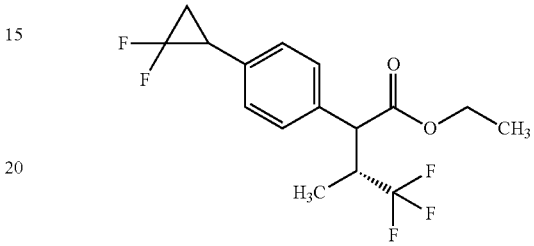

1.58 g (5.52 mmol) of ethyl (3R)-4,4,4-trifluoro-3-methyl-2-(4-vinylphenyl)butanoate, 23 mg (0.55 mmol) of sodium fluoride and 24 mg (0.11 mmol) of 2,6-di-tert-butyl 4-methylphenol were heated to 110° C. and stirred for 5 minutes. 1.9 ml (9.38 mmol) of trimethylsilyl 2,2-difluoro-2-(fluorosulphonyl)acetate were then slowly added dropwise, and the mixture was stirred at 110° C. for 60 min (careful: evolution of gas after about 30 min). After cooling to room temperature and addition of ethyl acetate and saturated aqueous sodium bicarbonate solution, the organic phase was separated off, dried over magnesium sulphate, filtered and concentrated to dryness. The crude product was purified chromatographically on silica gel (mobile phase cyclohexane/-dichloromethane 4:1). This gave 1.5 g of the title compound (81% of theory).

GC-MS (Method 1): $R_t$=4.99 min, m/z=336 (M)$^+$ (diastereomer 1); $R_t$=5.01 min, m/z=336 (M)$^+$ (diastereomer 2).

MS (DCI): m/z=354 (M+NH$_4$)$^+$.

Example 73A

Ethyl 2-[4-(bromomethyl)phenyl]-4,4,4-trifluoro-3-methylbutanoate

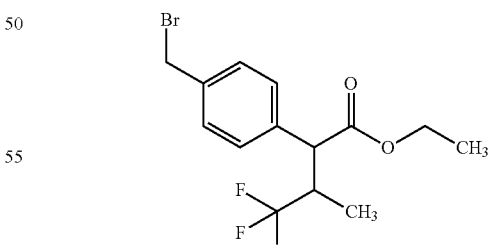

2.25 g (8.2 mmol) of ethyl 4,4,4-trifluoro-3-methyl-2-(4-methylphenyl)butanoate, 1.53 g (8.6 mmol) of N-bromosuccinimide and 67 mg (0.41 mmol) of 2,2'-azobis-(2-methylpropanenitrile) in 36 ml of trichloromethane were stirred under reflux overnight. After the reaction had gone to completion, the succinimide was filtered off, the filter residue was washed with dichloromethane and the filtrate was concentrated under reduced pressure. The crude product was purified chromatographically on silica gel (mobile phase cyclohexane/ethyl acetate 40:1). This gave 2.667 g (7.5 mmol, 92% of theory) of a yellowish oil.

GC-MS (Method 1): $R_t$=5.72 min, m/z=373 (M-Br)$^+$ (diastereomer 1); $R_t$=5.74 min, m/z=373 (M-Br)$^+$ (diastereomer 2).

Example 74A

Ethyl 4,4,4-trifluoro-3-methyl-2-[4-(2,2,2-trifluoroethyl)phenyl]butanoate

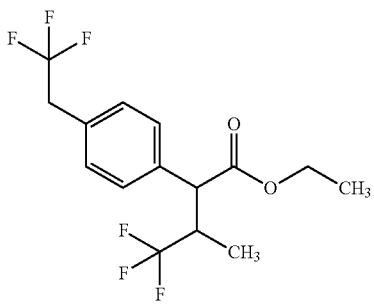 [SMILES: CCOC(=O)C(c1ccc(CC(F)(F)F)cc1)C(C)C(F)(F)F]

529 mg (2.78 mmol) of copper(I) iodide and 4 g (20.82 mmol) of methyl 2,2-difluoro-2-(fluorosulphonyl)acetate were added to 3.77 g (10.67 mmol) of ethyl 2-[4-(bromomethyl)phenyl]-4,4,4-trifluoro-3-methylbutanoate in 40 ml of 1-methylpyrrolidin-2-one, and the mixture was stirred at 80° C. overnight. After the reaction had ended, the reaction solution was slowly poured into 100 ml of ice-water. The mixture obtained was then extracted three times with diethyl ether. The combined organic phases were dried over magnesium sulphate. After filtration, the solvent was removed under reduced pressure. The crude product obtained was purified chromatographically on silica gel (mobile phase cyclohexane/dichloromethane 4:1). This gave 1.48 g (4.32 mmol, 41% of theory) of the title compound as a yellowish oil.

GC-MS (Method 1): $R_t$=4.06 min, m/z=342 (M)$^+$ (diastereomer 1); $R_t$=4.09 min, m/z=342 (M)$^+$ (diastereomer 2).

MS (DCI): m/z=360 (M+NH$_4$)$^+$.

Example 75A

Methyl (4-chlorophenyl)(3-oxocyclopentyl)acetate

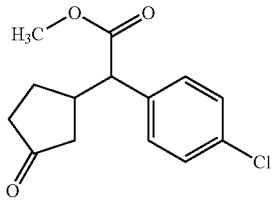 [SMILES: COC(=O)C(c1ccc(Cl)cc1)C1CCC(=O)C1]

Under argon, 14.8 ml (105.6 mmol) of diisopropylamine were initially charged in 150 ml of THF, the mixture was cooled to −30° C. and 42.3 ml (105.75 mmol) of a 2.5 M solution of n-butyllithium in hexane were added slowly. The reaction solution was then warmed to −20° C., 15 g (81.25 mmol) of methyl (4-chlorophenyl)acetate, dissolved in 90 ml of THF, were added slowly and the mixture was stirred at this temperature for 2 h. The reaction solution then cooled to −78° C., and 7.2 ml (86.1 mmol) of 2-cyclopenten-1-one, dissolved in 60 ml of THF, were added slowly. After the addition had ended, the solution was stirred at −78° C. for another hour. After TLC (mobile phase cyclohexane/ethyl acetate 9:1), saturated aqueous ammonium chloride solution was added and the product was taken up in ethyl acetate. The aqueous phase was extracted twice with ethyl acetate.

The combined organic phases were dried over magnesium sulphate. After filtration, the solvent was removed under reduced pressure. The crude product was purified chromatographically on silica gel (mobile phase cyclohexane/ethyl acetate 4:1). This gave 15.65 g (58.67 mmol, 72% of theory) of the title compound as a yellowish oil.

GC-MS (Method 1): $R_t$=7.02 min, m/z=266 (M)$^+$ (diastereomer 1); $R_t$=7.04 min, m/z=266 (M)$^+$ (diastereomer 2).

MS (DCI): m/z=284 (M+NH$_4$)$^+$.

Example 76A

Methyl (4-chlorophenyl)(3,3-difluorocyclopentyl)acetate

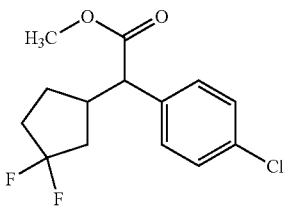 [SMILES: COC(=O)C(c1ccc(Cl)cc1)C1CCC(F)(F)C1]

Under argon, 82.5 ml (82.14 mmol) of a 50% strength solution of 1,1'-[(trifluoro-$\lambda^4$-sulphonyl)-imino]bis(2-methoxyethane) (Desoxofluor) in THF, diluted with 200 ml of toluene, were initially charged and cooled to 5° C., and 744 μl (5.87 mmol) of a 1 M solution of boron trifluoride/diethyl ether complex were added slowly. The mixture was stirred at 5° C. for 2 h. 15.65 g (58.67 mmol) of methyl (4-chlorophenyl)(3-oxocyclopentyl)acetate, dissolved in 200 ml of toluene, were then added slowly, and the reaction solution was subsequently warmed to 55° C. and stirred at this temperature for 60 h. The reaction mixture was then added to a mixture, cooled to 0° C., consisting of 100 ml of toluene and 100 ml of 2 M aqueous sodium hydroxide solution. The organic phase was separated off, and the aqueous phase was extracted three more times with ethyl acetate. The combined organic phases were dried over sodium sulphate. After filtration, the solvent was removed under reduced pressure. The crude product was purified chromatographically on silica gel (mobile phase cyclohexane/ethyl acetate 7:1). This gave 13.24 g (45.86 mmol, 78% of theory) of the title compound as a colourless oil.

MS (DCI): m/z=306 (M+NH$_4$)$^+$.

GC-MS (Method 1): $R_t$=5.83 min, m/z=288 (M)$^+$ (diastereomer 1); $R_t$=5.86 min, m/z=288 (M)$^+$ (diastereomer 2).

Example 77A (+)-(2S,3R)-2-(4-Chlorophenyl)-4,4,4-trifluoro-3-methylbutanoic acid

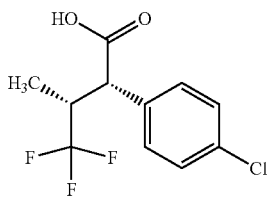 [SMILES: C[C@H]([C@H](C(=O)O)c1ccc(Cl)cc1)C(F)(F)F]

Method A:

5.086 g (17.26 mmol) of ethyl (3R)-2-(4-chlorophenyl)-4,4,4-trifluoro-3-methylbutanoate were dissolved in 68 ml of dioxane, and 34 ml of 1 N aqueous sodium hydroxide solution were added. The reaction was stirred at 50° C. for 2 h. The reaction mixture was then acidified with 1 N hydrochloric acid to pH 1 and repeatedly extracted with dichloromethane. The combined organic phases were washed with saturated sodium chloride solution, dried over sodium sulphate and concentrated under reduced pressure. This gave 3.9 g (14.63 mmol, 85% of theory, 83% de) of the target compound.

$^1$H-NMR (400 MHz, DMSO-$d_6$, δ/ppm): 12.95-12.73 (1H, br. s), 7.49-7.34 (4H, m), 3.68 (1H, d), 3.31-3.18 (1H, m), 1.20 (0.25H, d), 0.78 (2.75H, d).

GC-MS (Method 1): $R_t$=4.85 min; m/z=266 (M)$^+$.

$[α]_D^{20}$=+57.2°, c=0.41, methanol.

Method B:

16.28 g (55.24 mmol) of ethyl (3R)-2-(4-chlorophenyl)-4,4,4-trifluoro-3-methylbutanoate were dissolved in 220 ml of dioxane, and 110.5 ml of 1 N aqueous sodium hydroxide solution were added. The reaction was stirred at 50° C. for 3 h. The dioxane was then removed on a rotary evaporator, and the aqueous solution that remained was, with ice-cooling, neutralized with 1 N hydrochloric acid (~pH 7). The precipitated solid was filtered off with suction and dried under high vacuum at 40° C. overnight. This gave 9.2 g of the target compound as a slightly beige solid (fraction 1; 62.5% of theory, 94% de). The filtrate was acidified by further addition of 1 N hydrochloric acid (~pH 1) and stirred overnight. Once more, the precipitated solid was filtered off with suction and dried under high vacuum at 40° C. overnight. This gave a further 3.46 g of the target compound as a white solid (fraction 2; contaminated with 10% of the second diastereomer). The aqueous filtrate that remained was repeatedly extracted with dichloromethane, and the combined organic phases were dried over magnesium sulphate and concentrated under reduced pressure. This gave another 2.44 g of the target compound as a colourless oil (fraction 3; contaminated with 15% of the second diastereomer). Fractions 2 and 3 were finally combined and re-purified chromatographically on silica gel (mobile phase cyclohexane/ethyl acetate 10:1). This gave 3.7 g of the target compound as a white solid (fraction 4; 25% of theory, >95% de).

Fraction 1 (=Sodium Salt of the Title Compound):

$^1$H-NMR (400 MHz, DMSO-$d_6$, δ/ppm): 7.44-7.33 (4H, m), 3.61 (1H, d), 3.30-3.15 (1H, m), 1.17 (0.09H, d, minor diastereomer), 0.76 (2.91H, d, major diastereomer).

Fraction 4:

$^1$H-NMR (400 MHz, DMSO-$d_6$, δ/ppm): 13.03-12.69 (br. s, 1H), 7.47-7.39 (4H, m), 3.68 (1H, d), 3.39-3.17 (1H, m, partially obscured by H$_2$O signal), 0.77 (3H, d).

Compounds listed in the table below were prepared in an analogous manner:

| Example | Name/Structure/Starting material | Analytical data |
|---|---|---|
| 78A | (2S,3R)-4,4,4-trifluoro-3-methyl-2-(4-methylphenyl)butanoic acid<br><br>from ethyl (3R)-4,4,4-trifluoro-3-methyl-2-(4-methylphenyl)butanoate | GC-MS (Method 1): $R_t$ = 4.17 min; m/z = 246 (M)$^+$.<br>$^1$H-NMR (400 MHz, DMSO-$d_6$, δ/ppm): 0.75 (d, 2.75H, major diastereomer), 1.19 (d, 0.25H, minor diastereomer), 2.29 (s, 3H), 3.15-3.28 (m, 1H), 3.55 (d, 0.915H, major diastereomer), 3.60 (d, 0.085H, minor diastereomer), 7.17 (d, 2H), 7.24 (d, 2H), 12.68 (br. s. 1H) (83% de). |
| 79A | (2S,3R)-2-(4-ethylphenyl)-4,4,4-trifluoro-3-methylbutanoic acid<br><br>from ethyl (3R)-2-(4-ethylphenyl)-4,4,4-trifluoro-3-methylbutanoate | LC-MS (Method 5): $R_t$ = 1.06 min; m/z = 259 (M − H)$^−$.<br>$^1$H-NMR (400 MHz, DMSO-$d_6$, δ/ppm): 0.75 (d, 3H), 1.17 (t, 3H), 2.59 (q, 2H), 3.14-3.29 (m, 1H), 3.56 (d, 1H), 7.20 (d, 2H), 7.27 (d, 2H), 12.53-12.86 (br. s, 1H). |

| Example | Name/Structure/Starting material | Analytical data |
|---|---|---|
| 80A | (2S,3R)-2-(4-chloro-3-fluorophenyl)-4,4,4-trifluoro-3-methylbutanoic acid<br><br>from ethyl (3R)-2-(4-chloro-3-fluorophenyl)-4,4,4-trifluoro-3-methylbutanoate | LC-MS (Method 5):<br>$R_t$ = 1.06 min; m/z = 259 (M − H)$^-$.<br>$^1$H-NMR (400 MHz, DMSO-d$_6$, δ/ppm): 0.80 (d, 2.75H, major diastereomer), 1.19 (d, 0.25H, minor diastereomer), 3.21-3.37 (m, 1H, partially obscured by H$_2$O signal), 3.75 (d, 1H), 7.29 (dd, 1H), 7.51 (dd, 1H), 7.60 (t, 1H), 12.97 (br. s, 1H) (83% de). |
| 81A | (2S,3R)-4,4,4-trifluoro-2-(4-fluorophenyl)-3-methyl-butanoic acid<br><br>from ethyl (3R)-4,4,4-trifluoro-2-(4-fluorophenyl)-3-methylbutanoate | LC-MS (Method 5):<br>$R_t$ = 0.97 min; m/z = 249 (M − H)$^-$.<br>$^1$H-NMR (from sodium salt; 400 MHz, DMSO-d$_6$, δ/ppm): 0.76 (d, 2.73H, major diastereomer), 1.19 (d, 0.27H, minor diastereomer), 3.16-3.31 (m, 1H), 3.66 (d, 1H), 7.15-7.23 (m, 2H), 7.37-7.46 (m, 2H) (82% de). |
| 82A | (2S,3R)-4,4,4-trifluoro-2-(4-isopropylphenyl)-3-methyl-butanoic acid<br><br>from ethyl (3R)-4,4,4-trifluoro-2-(4-isopropylphenyl)-3-methyl-butanoate | $^1$H NMR (400 MHz, DMSO-d$_6$, δ/ppm): 12.56 (1H, br. s), 7.25 (4H, q), 3.56 (1H, d), 3.28-3.16 (1H, m), 2.94-2.81 (1H, m), 1.19 (6H, d), 0.75 (3H, d).<br>GC-MS (Method 1):<br>$R_t$ = 4.93 min; m/z = 274 (M)$^+$. |
| 83A | (2S,3R)-2-(4-tert-butylphenyl)-4,4,4-trifluoro-3-methylbutanoic acid<br><br>from ethyl (2S,3R)-2-(4-tert-butylphenyl)-4,4,4-trifluoro-3-methylbutanoate | GC-MS (Method 1):<br>$R_t$ = 5.15 min; m/z = 288 (M)$^+$. |

| Example | Name/Structure/Starting material | Analytical data |
|---|---|---|
| 84A | 4,4,4-trifluoro-3-methyl-2-[4-(2,2,2-trifluoroethyl)phenyl]butanoic acid<br>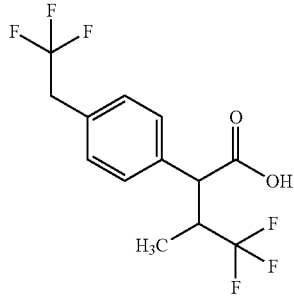<br>from ethyl 4,4,4-trifluoro-3-methyl-2-[4-(2,2,2-trifluoroethyl)phenyl]butanoate | $^1$H-NMR (400 MHz, DMSO-d$_6$, δ/ppm): 12.95-12.59 (1H, br. s), 7.37 (4H, q), 3.70-3.57 (3H, m), 3.30-3.18 (1H, m), 0.76 (3H, d).<br>GC-MS (Method 1):<br>R$_t$ = 4.45 min; m/z = 315 (M + H)$^+$. |
| 85A | (4-chlorophenyl)(3,3-difluorocyclopentyl) acetic acid<br>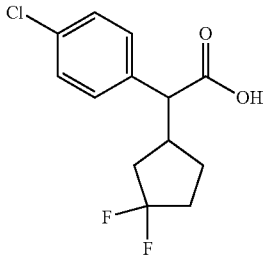<br>from methyl (4-chlorophenyl)(3,3-difluorocyclopentyl)acetate | $^1$H-NMR (400 MHz, DMSO-d$_6$, δ/ppm): 12.59 (1H, br. s), 7.38 (4H, q), 3.51 (0.5H, d), 3.48 (0.5H, d), 2.77-2.60 (1H, m), 2.42-2.27 (0.5H, m), 2.26-1.20 (5.5H, m).<br>GC-MS (Method 1):<br>R$_t$ = 6.33 min, m/z = 274 (M)$^+$ (diastereomer 1);<br>R$_t$ = 6.38 min, m/z = 274 (M)$^+$ (diastereomer 2). |
| 86A | (2S,3R)-2-(4-chloro-3-methoxyphenyl)-4,4,4-trifluoro-3-methylbutanoic acid<br>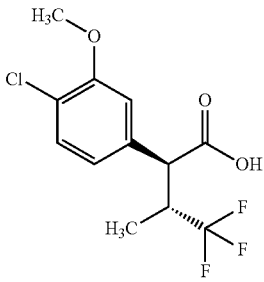<br>from ethyl (3R)-2-(4-chloro-3-methoxyphenyl)-4,4,4-trifluoro-3-methylbutanoate | $^1$H-NMR (400 MHz, DMSO-d$_6$, δ/ppm): 12.91-12.71 (1H, br. s), 7.41 (1H, d), 7.18 (1H, d), 6.98 (1H, dd), 3.86 (3H, s), 3.66 (1H, d), 3.40-3.19 (1H, m), 0.79 (3H, d).<br>LC-MS (Method 2): R$_t$ = 2.20 min; m/z = 295/297 (M − H)$^-$. |

| Example | Name/Structure/Starting material | Analytical data |
|---|---|---|
| 87A | 2-(4-chloro-3-methylphenyl)-4,4,4-trifluoro-3-methylbutanoic acid<br>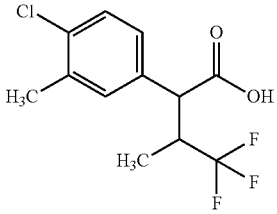<br>from ethyl 2-(4-chloro-3-methylphenyl)-4,4,4-trifluoro-3-methylbutanoate | GC-MS (Method 1):<br>$R_t$ = 5.20 min; m/z = 280/282 (M)$^+$ (diastereomer 1);<br>$R_t$ = 5.23 min; m/z = 280/282 (M)$^+$ (diastereomer 2). |
| 88A | (2S,3R)-2-[4-(2,2-difluorocyclopropyl)phenyl]-4,4,4-trifluoro-3-methylbutanoic acid<br>(diastereomer mixture)<br>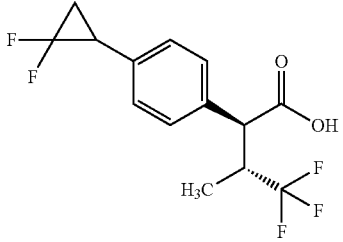<br>(from ethyl (2S,3R)-2-[4-(2,2-difluorocyclopropyl)phenyl]-4,4,4-trifluoro-3-methylbutanoate) | LC-MS (Method 5):<br>$R_t$ = 1.09 min; m/z = 307 (M − H)$^−$.<br>$^1$H-NMR (400 MHz, DMSO-d$_6$):<br>δ [ppm] = 0.76 (d, 3H), 1.86-2.04 (m, 2H), 2.92-3.06 (m, 1H), 3.18-3.29 (m, 1H), 3.61 (d, 1H), 7.27 (d, 2H), 7.34 (d, 2H), 12.72 (br. s, 1H). |

Example 89A (3R)-2-(4-Ethylphenyl)-4,4,4-trifluoro-3-methylbutanoic acid (Diastereomer Mixture)

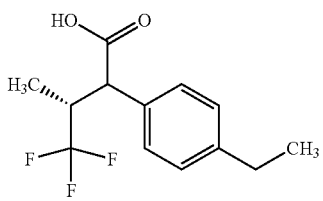 [SMILES: CCc1ccc(C(C(=O)O)[C@@H](C)C(F)(F)F)cc1]

3.0 g of ethyl (3R)-2-(4-ethylphenyl)-4,4,4-trifluoro-3-methylbutanoate (purity about 88%, about 9.16 mmol; diastereomer mixture) were dissolved in the mixture of in each case 12.4 ml of methanol, THF and water, and 5.49 g (137.35 mmol) of sodium hydroxide were added a little at a time. The reaction mixture was stirred at 40° C. for 9 h. After cooling, the volatile solvents were substantially removed under reduced pressure and the residue was diluted with water. The mixture was acidified by addition of hydrochloric acid, and the aqueous phase was extracted three times with ethyl acetate. The combined organic phases were dried over sodium sulphate, and concentrated under reduced pressure, and the residue was dried under high vacuum. This gave 2.61 g of the title compound as a crude product which was not purified any further (diastereomer ratio about 9:1).

LC-MS (Method 5): $R_t$=1.08 min, m/z=259 (M−H)$^−$ (minor diastereomer); $R_t$=1.11 min, m/z=259 (M−H)$^−$ (major diastereomer).

$^1$H-NMR (400 MHz, DMSO-d$_6$): major diastereomer: δ [ppm]=0.76 (d, 3H), 1.17 (t, 3H), 2.54-2.66 (m, 4H), 3.10-3.29 (m, 1H), 3.56 (d, 1H), 7.14-7.22 (m, 2H), 7.22-7.32 (m, 2H), 12.58 (br. s, 1H).

In a comparable manner (reaction temperature: RT to +40° C.; reaction time: 9-12 h), the following carboxylic acids were prepared from the corresponding esters:

Example 90A (3R)-4,4,4-Trifluoro-2-(4-fluorophenyl)-3-methylbutanoic acid (Diastereomer Mixture)

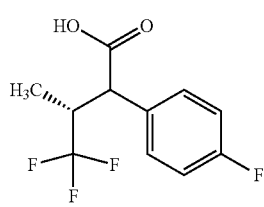 [SMILES: C[C@H](C(C(=O)O)c1ccc(F)cc1)C(F)(F)F]

Diastereomer ratio about 9:1.

$^1$H-NMR (400 MHz, DMSO-d$_6$): major diastereomer: δ [ppm]=0.77 (d, 3H), 3.18-3.30 (m, 1H), 3.67 (d, 1H), 7.17-7.24 (m, 2H), 7.39-7.47 (m, 2H), 12.78 (br. s, 1H).

Example 91A (3R)-2-(4-Chloro-3-fluorophenyl)-4,4,4-trifluoro-3-methylbutanoic acid (Diastereomer Mixture)

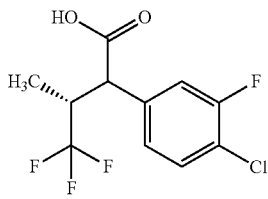 [SMILES: C[C@H](C(C(=O)O)c1ccc(Cl)c(F)c1)C(F)(F)F]

Diastereomer ratio about 1:1.
GC-MS (Method 1): $R_t$=4.79 min; m/z=284 (M)⁺.
¹H-NMR (400 MHz, DMSO-$d_6$): both diastereomers: δ [ppm]=0.80/1.19 (each d, 3H), 3.18-3.29 (m, 1H), 3.74/3.77 (each dd, 1H), 7.28 (d, 1H), 7.43-7.65 (m, 2H), 12.91/13.24 (each br. s, 1H).

Examples 92A-95A (4-Chlorophenyl)(3,3-difluorocyclopentyl)acetic acid (Isomers 1-4)

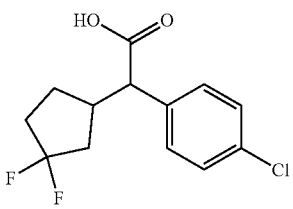 [SMILES: O=C(O)C(c1ccc(Cl)cc1)C1CCC(F)(F)C1]

By preparative HPLC on a chiral phase, 4 g (14.56 mmol) of the diastereomer mixture of (4-chlorophenyl)(3,3-difluorocyclopentyl)acetic acid (Example 85A) were separated into the four enantiomerically pure diastereomers [column: Daicel Chiralpak AD-H, 5 μm, 250 mm×20 mm; mobile phase: isohexane/(ethanol+0.2% trifluoroacetic acid+1% water) 95:5 (v/v); flow rate: 20 ml/min; UV detection: 230 nm; temperature: 25° C.]:

Example 92A (Isomer 1):
Yield: 682 mg
$R_t$=8.12 min; chemical purity >94%
[Column: Daicel AD-H, 5 μm, 250 mm×4.6 mm; mobile phase: isohexane/(ethanol+0.2% trifluoroacetic acid+1% water) 95:5 (v/v); flow rate: 1.25 ml/min; UV detection: 230 nm; temperature: 30° C.].
LC-MS (Method 5): $R_t$=1.03 min; m/z=273 (M–H)⁻.
¹H-NMR (400 MHz, DMSO-$d_6$): δ [ppm]=1.46-1.82 (m, 3H), 1.96-2.27 (m, 3H), 2.62-2.77 (m, 1H), 3.50 (d, 1H), 7.35 (d, 2H), 7.41 (d, 2H), 12.60 (br. s, 1H).
$[α]_D^{20}$=–54.2°, c=0.490, methanol.

Example 93A (Isomer 2):
Yield: 543 mg
$R_t$=9.53 min; chemical purity >97%
[Column: Daicel AD-H, 5 μm, 250 mm×4.6 mm; mobile phase: isohexane/(ethanol+0.2% trifluoroacetic acid+1% water) 95:5 (v/v); flow rate: 1.25 ml/min; UV detection: 230 nm; temperature: 30° C.].
LC-MS (Method 5): $R_t$=1.03 min; m/z=273 (M–H)⁻.
¹H-NMR (400 MHz, DMSO-$d_6$): δ [ppm]=1.46-1.82 (m, 3H), 1.96-2.27 (m, 3H), 2.63-2.77 (m, 1H), 3.50 (d, 1H), 7.35 (d, 2H), 7.41 (d, 2H), 12.61 (br. s, 1H).
$[α]_D^{20}$=+53.0°, c=0.375, methanol.

Example 94A (Isomer 3):
Yield: 530 mg
$R_t$=10.36 min; chemical purity >92%
[Column: Daicel AD-H, 5 μm, 250 mm×4.6 mm; mobile phase: isohexane/(ethanol+0.2% trifluoroacetic acid+1% water) 95:5 (v/v); flow rate: 1.25 ml/min; UV detection: 230 nm; temperature: 30° C.].
LC-MS (Method 5): $R_t$=1.04 min; m/z=273 (M–H)⁻.
¹H-NMR (400 MHz, DMSO-$d_6$): δ [ppm]=1.21-1.34 (m, 1H), 1.34-1.45 (m, 1H), 1.76-2.17 (m, 3H), 2.27-2.42 (m, 1H), 2.60-2.75 (m, 1H), 3.49 (d, 1H), 7.35 (d, 2H), 7.41 (d, 2H), 12.60 (br. s, 1H).
$[α]_D^{20}$=–61.0°, c=0.340, methanol.

Example 95A (Isomer 4):
Yield: 560 mg
$R_t$=11.35 min; chemical purity >91%
[Column: Daicel AD-H, 5 μm, 250 mm×4.6 mm; mobile phase: isohexane/(ethanol+0.2% trifluoroacetic acid+1% water) 95:5 (v/v); flow rate: 1.25 ml/min; UV detection: 230 nm; temperature: 30° C.].
LC-MS (Method 5): $R_t$=1.04 min; m/z=273 (M–H)⁻.
¹H-NMR (400 MHz, DMSO-$d_6$): δ [ppm]=1.21-1.34 (m, 1H), 1.34-1.45 (m, 1H), 1.77-2.17 (m, 3H), 2.27-2.42 (m, 1H), 2.60-2.75 (m, 1H), 3.49 (d, 1H), 7.35 (d, 2H), 7.41 (d, 2H), 12.59 (br. s, 1H).
$[α]_D^{20}$=+56.4°, c=0.485, methanol.

Example 96A

Methyl 3-(4-chloro-3-{[(2S,3R)-2-(4-chlorophenyl)-4,4,4-trifluoro-3-methylbutanoyl]amino}-phenyl)-4-methylpentanoate (Diastereomer 1)

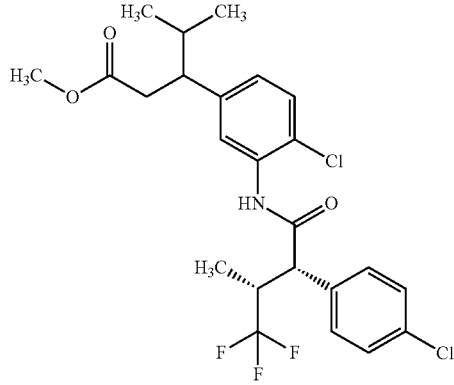 [SMILES: COC(=O)CC(c1ccc(Cl)c(NC(=O)[C@H](c2ccc(Cl)cc2)[C@@H](C)C(F)(F)F)c1)C(C)C]

328 mg (1.23 mmol) of (2S,3R)-2-(4-chlorophenyl)-4,4,4-trifluoro-3-methylbutanoic acid were dissolved in 17.5 ml of dichloromethane, 263 mg (1.97 mmol) of 1-chloro-N,N,2-trimethylprop-1-ene-1-amine were added and the mixture was stirred at room temperature for 30 min. 299 μl (3.7 mmol) of pyridine and 315 mg (1.23 mmol) of methyl 3-(3-amino-4-chlorophenyl)-4-methylpentanoate (enantiomer 1; Example 17A) were then added, and the reaction mixture was stirred overnight. The reaction mixture was then concentrated under reduced pressure and the crude product obtained was purified directly by preparative RP-HPLC (mobile phase methanol/water 80:20). This gave 237 mg of the target compound (38% of theory).
LC-MS (Method 5): $R_t$=1.43 min; m/z=504/506 (M+H)⁺.
¹H-NMR (400 MHz, DMSO-$d_6$): δ [ppm]=0.68 (d, 3H), 0.80 (d, 3H), 0.85 (d, 3H), 1.70-1.85 (m, 1H), 2.48-2.58 (m, 1H, partially obscured by DMSO signal), 2.70-2.80 (m, 2H), 3.30-3.41 (m, 1H, partially obscured by H$_2$O signal), 3.42 (s, 3H), 4.12 (d, 1H), 7.01 (dd, 1H), 7.31-7.37 (m, 2H), 7.43-7.50 (m, 4H), 9.83 (s, 1H).

$[\alpha]_D^{20}$=+111°, c=0.25, methanol.

Example 97A

Methyl 3-(4-chloro-3-{[(2S,3R)-2-(4-chlorophenyl)-4,4,4-trifluoro-3-methylbutanoyl]amino}-phenyl)-4-methylpentanoate (Diastereomer 2)

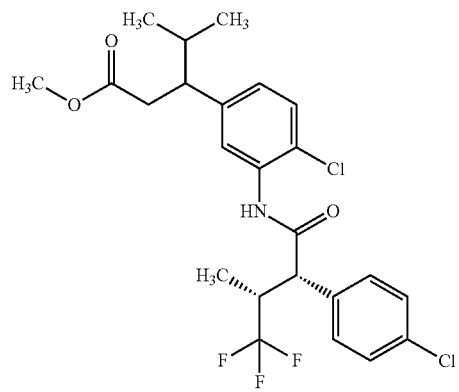 [SMILES: COC(=O)CC(c1ccc(Cl)c(NC(=O)[C@H](c2ccc(Cl)cc2)[C@@H](C)C(F)(F)F)c1)C(C)C]

255 mg (0.96 mmol) of (2S,3R)-2-(4-chlorophenyl)-4,4,4-trifluoro-3-methylbutanoic acid were dissolved in 14 ml of dichloromethane, 205 mg (1.53 mmol) of 1-chloro-N,N,2-trimethylprop-1-ene-1-amine were added and the mixture was stirred at room temperature for 30 min. 232 μl (2.87 mmol) of pyridine and 245 mg (0.96 mmol) of methyl 3-(3-amino-4-chlorophenyl)-4-methylpentanoate (enantiomer 2; Example 18A) were then added, and the reaction mixture was stirred overnight. The reaction mixture was then concentrated under reduced pressure and the crude product obtained was purified directly by preparative RP-HPLC (mobile phase methanol/water 80:20). This gave 228 mg of the target compound (47% of theory).

LC-MS (Method 5): R$_t$=1.43 min; m/z=504/506 (M+H)$^+$.

$^1$H-NMR (400 MHz, DMSO-d$_6$): δ [ppm]=0.67 (d, 3H), 0.80 (d, 3H), 0.85 (d, 3H), 1.71-1.82 (m, 1H), 2.47-2.58 (m, 1H, partially obscured by DMSO signal), 2.70-2.80 (m, 2H), 3.29-3.41 (m, 1H, partially obscured by H$_2$O signal), 3.43 (s, 3H), 4.12 (d, 1H), 7.01 (dd, 1H), 7.33 (d, 1H), 7.35 (d, 1H), 7.43-7.50 (m, 4H), 9.82 (s, 1H).

$[\alpha]_D^{20}$=+84.7°, c=0.325, methanol.

Example 98A tert-Butyl 3-(4-chloro-3-{[(2S,3R)-2-(4-chlorophenyl)-4,4,4-trifluoro-3-methylbutanoyl]amino}-phenyl)-3-cyclopropylpropanoate (Diastereomer 1)

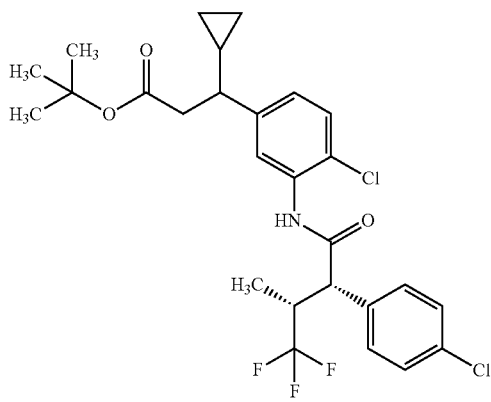 [SMILES: C[C@H]([C@H](C(=O)Nc1cc(C(CC(=O)OC(C)(C)C)C2CC2)ccc1Cl)c1ccc(Cl)cc1)C(F)(F)F]

45 mg (0.17 mmol) of (2S,3R)-2-(4-chlorophenyl)-4,4,4-trifluoro-3-methylbutanoic acid were dissolved in 1 ml of dichloromethane, 36 mg (0.27 mmol) of 1-chloro-N,N,2-trimethylprop-1-ene-1-amine were added and the mixture was stirred at room temperature for 30 min. 41 μl (0.51 mmol) of pyridine and 50 mg (0.17 mmol) of tert-butyl 3-(3-amino-4-chlorophenyl)-3-cyclopropylpropanoate (enantiomer 1; Example 30A), dissolved in 1 ml of dichloromethane, were then added, and the reaction mixture was stirred for another 1 h. The reaction mixture was then concentrated under reduced pressure and the crude product obtained was directly purified chromatographically on silica gel (mobile phase cyclohexane/ethyl acetate 20:1). This gave 78 mg of the target compound (85% of theory).

LC-MS (Method 7): R$_t$=1.52 min; m/z=542/544 (M–H)$^-$.

Example 99A tert-Butyl 3-(4-chloro-3-{[(2S,3R)-2-(4-chlorophenyl)-4,4,4-trifluoro-3-methylbutanoyl]amino}-phenyl)-3-cyclopropylpropanoate (diastereomer 2)

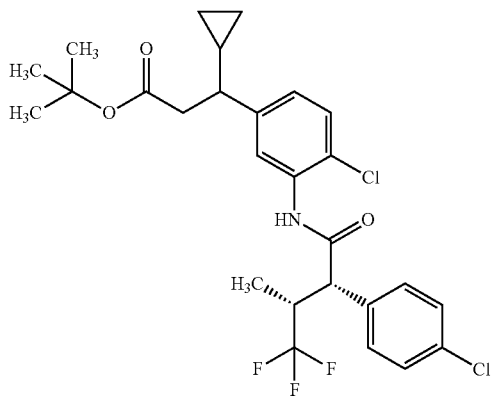 [SMILES: C[C@H]([C@H](C(=O)Nc1cc(C(CC(=O)OC(C)(C)C)C2CC2)ccc1Cl)c1ccc(Cl)cc1)C(F)(F)F]

119 mg (0.45 mmol) of (2S,3R)-2-(4-chlorophenyl)-4,4,4-trifluoro-3-methylbutanoic acid were dissolved in 2 nil of dichloromethane, 95 mg (0.71 mmol) of 1-chloro-N,N,2-trimethylprop-1-ene-1-amine were added and the mixture was stirred at room temperature for 30 min. 108 (1.34 mmol) of pyridine and 132 mg (0.45 mmol) of tert-butyl 3-(3-amino-4-chlorophenyl)-3-cyclopropylpropanoate (enantiomer 2; Example 31A), dissolved in 2 ml of dichloromethane, were then added, and the reaction mixture was stirred for another 1 h. The reaction mixture was then concentrated under reduced pressure and the crude product obtained was directly purified chromatographically on silica gel (mobile phase cyclohexane/ethyl acetate 20:1). This gave 206 mg of the target compound as a colourless oil (85% of theory).

LC-MS (Method 7): $R_t$=1.53 min; m/z=542/544 (M−H)⁻.

¹H-NMR (400 MHz, DMSO-$d_6$): δ [ppm]=0.03-0.11 (m, 1H), 0.17-0.34 (m, 2H), 0.45-0.55 (m, 1H), 0.80 (d, 3H), 0.88-1.00 (m, 1H), 1.21 (s, 9H), 2.14-2.24 (m, 1H), 2.47-2.57 (m, 1H, obscured by DMSO signal), 2.58-2.66 (m, 1H), 3.29-3.44 (m, 1H, partially obscured by H₂O signal), 4.14 (d, 1H), 7.11 (dd, 1H), 7.37 (d, 1H), 7.40-7.51 (m, 5H), 9.82 (s, 1H).

The compounds listed in the table below were prepared in an analogous manner:

| Example | Name/Structure/Starting materials | Analytical data |
|---|---|---|
| 100A | tert-butyl 3-(4-chloro-3-{[(2S,3R)-2-(4-chlorophenyl)-4,4,4-trifluoro-3-methylbutanoyl]-amino}phenyl)-3-(1-methylcyclopropyl)propanoate<br><br>from tert-butyl 3-(3-amino-4-chlorophenyl)-3-(1-methylcyclopropyl)propanoate and (2S,3R)-2-(4-chlorophenyl)-4,4,4-trifluoro-3-methylbutanoic acid | LC-MS (Method 7):<br>$R_t$ = 1.56 min; m/z = 556/558 (M − H)⁻. |
| 101A | tert-butyl 3-(4-chloro-3-{[(2S,3R)-2-(4-chlorophenyl)-4,4,4-trifluoro-3-methylbutanoyl]-amino}phenyl)-4-methoxy-4-methylpentanoate<br><br>from tert-butyl 3-(3-amino-4-chlorophenyl)-4-methoxy-4-methylpentanoate and (2S,3R)-2-(4-chlorophenyl)-4,4,4-trifluoro-3-methylbutanoic acid | LC-MS (Method 5):<br>$R_t$ = 1.48 min; m/z = 574/576 (M − H)⁻. |

| Example | Name/Structure/Starting materials | Analytical data |
|---------|-----------------------------------|-----------------|
| 102A | tert-butyl 3-(4-chloro-3-{[(2S,3R)-2-(4-chlorophenyl)-4,4,4-trifluoro-3-methylbutanoyl]amino}phenyl)-3-(1-fluorocyclopropyl)propanoate<br>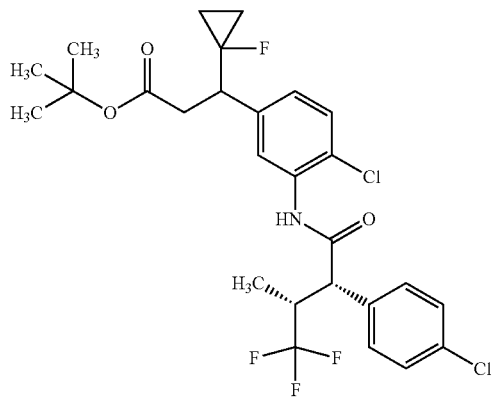<br>from tert-butyl 3-(3-amino-4-chlorophenyl)-3-(1-fluorocyclopropyl)propanoate and (2S,3R)-2-(4-chlorophenyl)-4,4,4-trifluoro-3-methylbutanoic acid | LC-MS (Method 5):<br>$R_t$ = 1.46 min; m/z = 560/562 (M − H)⁻. |
| 103A | methyl 3-(4-chloro-3-{[(2S,3R)-2-(4-chlorophenyl)-4,4,4-trifluoro-3-methylbutanoyl]amino}phenyl)-3,4-dimethylpentanoate (diastereomer 1)<br>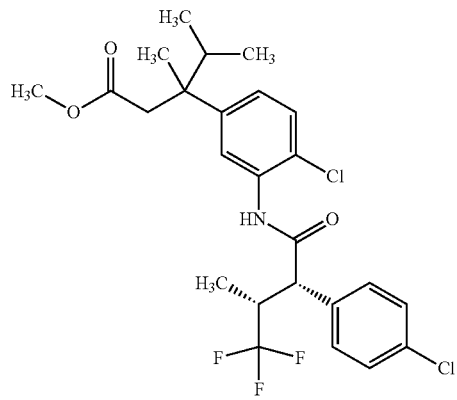<br>from methyl 3-(3-amino-4-chlorophenyl)-3,4-dimethylpentanoate (enantiomer 1, Example 50A) and (+)-(2S,3R)-2-(4-chlorophenyl)-4,4,4-trifluoro-3-methylbutanoic acid | LC-MS (Method 7):<br>$R_t$ = 1.48 min; m/z = 518/520 (M + H)⁺.<br>¹H-NMR (400 MHz, DMSO-$d_6$): δ [ppm] = 0.56 (d, 3H), 0.81 (dd, 6H), 1.29 (s, 3H), 1.82-1.93 (m, 1H), 2.58 (d, 1H), 2.77 (d, 1H), 3.30-3.44 (m, 1H), 3.33 (s, 3H), 4.12 (d, 1H), 7.12 (dd, 1H), 7.33 (d, 1H), 7.43-7.50 (m, 5H), 9.81 (s, 1H). |

| Example | Name/Structure/Starting materials | Analytical data |
|---|---|---|
| 104A | methyl 3-(4-chloro-3-{[(2S,3R)-2-(4-chlorophenyl)-4,4,4-trifluoro-3-methylbutanoyl]amino}phenyl)-3,4-dimethylpentanoate (diastereomer 2)<br><br>from methyl 3-(3-amino-4-chlorophenyl)-3,4-dimethylpentanoate (enantiomer 2, Example 51A) and (+)-(2S,3R)-2-(4-chlorophenyl)-4,4,4-trifluoro-3-methylbutanoic acid | LC-MS (Method 5):<br>$R_t$ = 1.48 min; m/z = 518/520 (M + H)$^+$.<br>$^1$H-NMR (400 MHz, DMSO-d$_6$): δ [ppm] = 0.57 (d, 3H), 0.81 (dd, 6H), 1.29 (s, 3H), 1.80-1.92 (m, 1H), 2.58 (d, 1H), 2.77 (d, 1H), 3.29-3.46 (m, 1H), 3.35 (s, 3H), 4.12 (d, 1H), 7.12 (dd, 1H), 7.33 (d, 1H), 7.42-7.50 (m, 5H), 9.81 (s, 1H). |
| 105A | methyl 3-(4-chloro-3-{[(2S,3R)-2-(4-chlorophenyl)-4,4,4-trifluoro-3-methylbutanoyl]amino}phenyl)-3-cyclobutylbutanoate (diastereomer 1)<br><br>from methyl 3-(3-amino-4-chlorophenyl)-3-cyclobutylbutanoate (enantiomer 1, Example 52A) and (+)-(2S,3R)-2-(4-chlorophenyl)-4,4,4-trifluoro-3-methylbutanoic acid | LC-MS (Method 5):<br>$R_t$ = 1.51 min; m/z = 530/532 (M + H)$^+$.<br>$^1$H-NMR (400 MHz, DMSO-d$_6$): δ [ppm] = 0.80 (d, 3H), 1.31 (s, 3H), 1.44-1.53 (m, 1H), 1.53-1.67 (m, 3H), 1.67-1.78 (m, 2H), 2.46 (d, 1H), 2.47-2.60 (m, 1H, partially obscured by DMSO signal), 2.70 (d, 1H), 3.36-3.46 (m, 1H), 3.38 (s, 3H), 4.12 (d, 1H), 7.10 (dd, 1H), 7.34 (d, 1H), 7.42-7.51 (m, 5H), 9.81 (s, 1H). |

-continued

| Example | Name/Structure/Starting materials | Analytical data |
|---|---|---|
| 106A | methyl 3-(4-chloro-3-{[(2S,3R)-2-(4-chlorophenyl)-4,4,4-trifluoro-3-methylbutanoyl]amino}phenyl)-3-cyclobutylbutanoate (diastereomer 2)<br>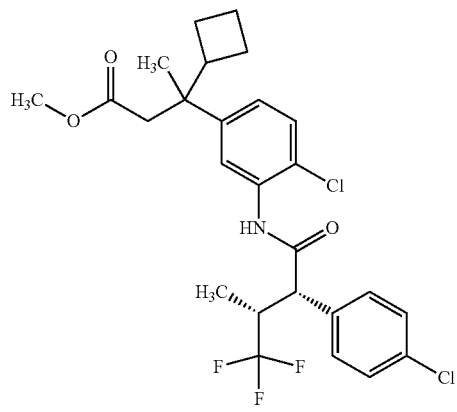<br>from methyl 3-(3-amino-4-chlorophenyl)-3-cyclobutylbutanoate (enantiomer 2, Example 53A) and (+)-(2S,3R)-2-(4-chlorophenyl)-4,4,4-trifluoro-3-methylbutanoic acid | LC-MS (Method 5): $R_t$ = 1.51 min; m/z = 530/532 $(M + H)^+$.<br>$^1$H-NMR (400 MHz, DMSO-$d_6$): δ [ppm] = 0.81 (d, 3H), 1.31 (s, 3H), 1.43-1.53 (m, 1H), 1.53-1.67 (m, 3H), 1.67-1.78 (m, 2H), 2.46 (d, 1H), 2.46-2.59 (m, 1H, partially obscured by DMSO signal), 2.70 (d, 1H), 3.36-3.46 (m, 1H), 3.40 (s, 3H), 4.12 (d, 1H), 7.10 (dd, 1H), 7.34 (d, 1H), 7.43-7.50 (m, 5H), 9.81 (s, 1H). |
| 107A | methyl 3-(4-chloro-3-{[(2S,3R)-2-(4-ethylphenyl)-4,4,4-trifluoro-3-methylbutanoyl]amino}phenyl)-4-methylpentanoate (diastereomer 1)<br>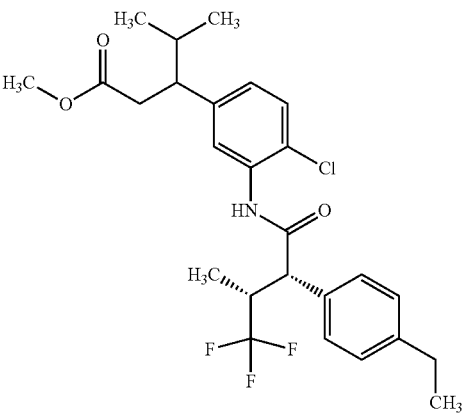<br>from methyl 3-(3-amino-4-chlorophenyl)-4-methyl-pentanoate (enantiomer 1, Example 17A) and (2S,3R)-2-(4-ethylphenyl)-4,4,4-trifluoro-3-methylbutanoic acid | LC-MS (Method 5): $R_t$ = 1.48 min; m/z = 498 $(M + H)^+$.<br>$^1$H-NMR (400 MHz, DMSO-$d_6$): δ [ppm] = 0.68 (d, 3H), 0.79 (d, 3H), 0.85 (d, 3H), 1.17 (t, 3H), 1.70-1.84 (m, 1H), 2.45-2.64 (m, 3H, partially obscured by DMSO signal), 2.70-2.82 (m, 2H), 3.28-3.39 (m, 1H, partially obscured by $H_2O$ signal), 3.42 (s, 3H), 4.06 (d, 1H), 6.98 (dd, 1H), 7.21 (d, 2H), 7.30-7.39 (m, 4H), 9.73 (s, 1H). |

| Example | Name/Structure/Starting materials | Analytical data |
|---|---|---|
| 108A | methyl 3-(4-chloro-3-{[(2S,3R)-2-(4-chloro-3-fluorophenyl)-4,4,4-trifluoro-3-methylbutanoyl]-amino}phenyl)-4-methylpentanoate (diastereomer 1)<br>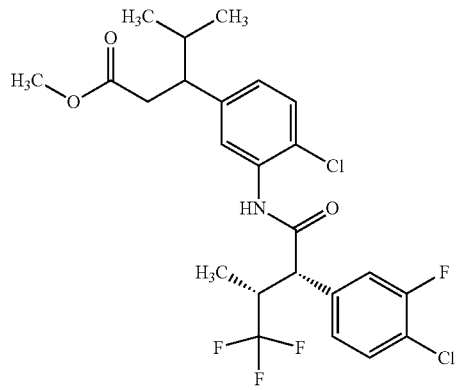<br>from methyl 3-(3-amino-4-chlorophenyl)-4-methyl-pentanoate (enantiomer 1, Example 17A) and (2S,3R)-2-(4-chloro-3-fluorophenyl)-4,4,4-trifluoro-3-methylbutanoic acid | LC-MS (Method 5): $R_t$ = 1.43 min; m/z = 522/524 $(M + H)^+$.<br>$^1$H-NMR (400 MHz, DMSO-$d_6$): δ [ppm] = 0.68 (d, 2.77H, major diastereomer), 0.84 (t, 6H), 1.25 (d, 0.23H, minor diastereomer), 1.71-1.84 (m, 1H), 2.46-2.60 (m, 1H, partially obscured by DMSO signal), 2.70-2.81 (m, 2H), 3.36-3.49 (m, 1H), 3.43 (s, 3H), 4.15 (d, 1H), 7.02 (dd, 1H), 7.29-7.38 (m, 3H), 7.50 (dd, 1H), 7.63 (t, 1H), 9.87 (s, 0.925H, major diastereomer), 10.01 (s, 0.075H, minor diastereomer) (85% de). |
| 109A | methyl 3-(4-chloro-3-{[(2S,3R)-4,4,4-trifluoro-2-(4-isopropylphenyl)-3-methylbutanoyl]amino}-phenyl)-4-methylpentanoate (diastereomer 1)<br>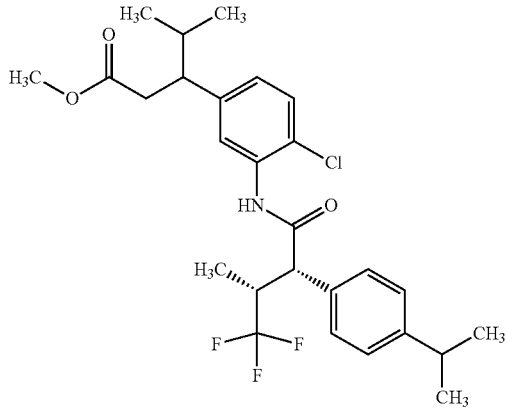<br>from methyl 3-(3-amino-4-chlorophenyl)-4-methyl-pentanoate (enantiomer 1, Example 17A) and (2S,3R)-4,4,4-trifluoro-2-(4-isopropylphenyl)-3-methylbutanoic acid | LC-MS (Method 5): $R_t$ = 1.54 min; m/z = 512/514 $(M + H)^+$.<br>$^1$H-NMR (400 MHz, DMSO-$d_6$): δ [ppm] = 0.68 (d, 3H), 0.79 (d, 3H), 0.85 (d, 3H), 1.19 (d, 6H), 1.71-1.83 (m, 1H), 2.45-2.58 (m, 1H, obscured by DMSO signal), 2.70-2.80 (m, 2H), 2.81-2.93 (m, 1H), 3.28-3.39 (m, 1H, partially obscured by H$_2$O signal), 3.42 (s, 3H), 4.07 (d, 1H), 6.98 (dd, 1H), 7.24 (d, 2H), 7.31-7.41 (m, 4H), 9.73 (s, 1H). |

| Example | Name/Structure/Starting materials | Analytical data |
|---|---|---|
| 110A | methyl 3-(4-chloro-3-{[(2S,3R)-4,4,4-trifluoro-2-(4-fluorophenyl)-3-methylbutanoyl]amino}-phenyl)-4-methylpentanoate (diastereomer 1)<br>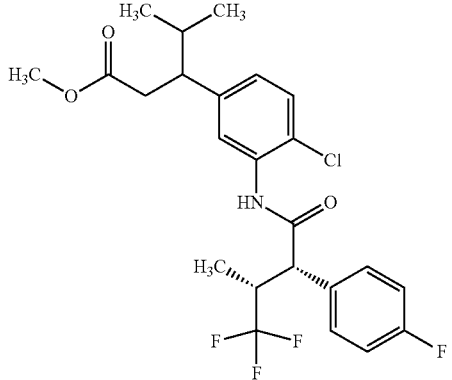<br>from methyl 3-(3-amino-4-chlorophenyl)-4-methyl-pentanoate (enantiomer 1, Example 17A) and (2S,3R)-4,4,4-trifluoro-2-(4-fluorophenyl)-3-methylbutanoic acid | LC-MS (Method 5):<br>$R_t$ = 1.36 min; m/z = 488/490 $(M + H)^+$.<br>$^1$H-NMR (400 MHz, DMSO-$d_6$): δ [ppm] = 0.68 (d, 2.77H, major diastereomer), 0.80 (d, 3H), 0.85 (d, 3H), 1.25 (d, 0.23H, minor diastereomer), 1.71-1.83 (m, 1H), 2.45 (m, 1H, obscured by DMSO signal), 2.70-2.81 (m, 2H), 3.28-3.40 (m, 1H, partially obscured by H$_2$O signal), 3.42 (s, 3H), 4.11 (d, 1H), 7.00 (dd, 1H), 7.22 (t, 2H), 7.31-7.37 (m, 2H), 7.44-7.54 (m, 2H), 9.80 (s, 0.925H, major diastereomer), 9.93 (s, 0.075H, minor diastereomer) (85% de). |
| 111A | methyl 3-[4-chloro-3-({4,4,4-trifluoro-3-methyl-2-[4-(2,2,2-trifluoroethyl)phenyl]butanoyl}amino)-phenyl]-4-methylpentanoate (diastereomer mixture)<br>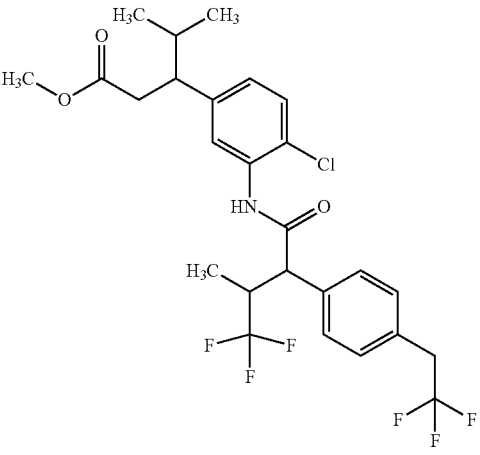<br>from methyl 3-(3-amino-4-chlorophenyl)-4-methyl-pentanoate (enantiomer 1, Example 17A) and 4,4,4-trifluoro-3-methyl-2-[4-(2,2,2-trifluoroethyl)-phenyl]butanoic acid (diastereomer mixture) | LC-MS (Method 5):<br>$R_t$ = 1.40 min; m/z = 522/554 $(M + H)^+$. |

| Example | Name/Structure/Starting materials | Analytical data |
|---|---|---|
| 112A | methyl 3-[4-chloro-3-({(2S,3R)-2-[4-(2,2-difluoro-cyclopropyl)phenyl]-4,4,4-trifluoro-3-methyl-butanoyl}amino)phenyl]-4-methylpentanoate (diastereomer mixture)<br>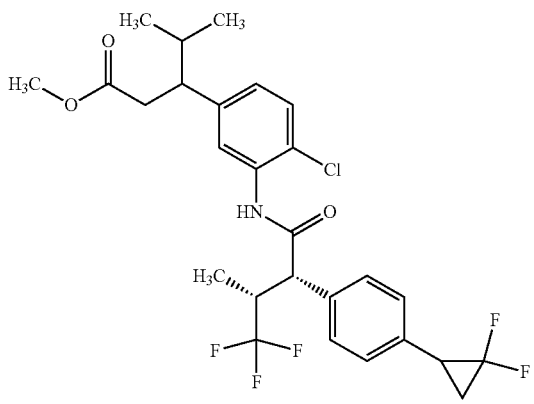<br>from methyl 3-(3-amino-4-chlorophenyl)-4-methylpentanoate (enantiomer 1, Example 17A) and (2S,3R)-2-[4-(2,2-difluorocyclopropyl)phenyl]-4,4,4-trifluoro-3-methylbutanoic acid (diastereomer mixture) | LC-MS (Method 5):<br>$R_t$ = 1.39 min; m/z = 546/548 (M + H)$^+$. |
| 113A | methyl 3-(3-{[(2S,3R)-2-(4-tert-butylphenyl)-4,4,4-trifluoro-3-methylbutanoyl]amino}-4-chloro-phenyl)-4-methylpentanoate (diastereomer 1)<br>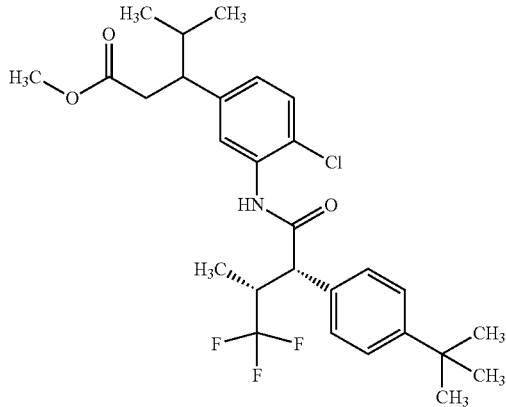<br>from methyl 3-(3-amino-4-chlorophenyl)-4-methyl-pentanoate (enantiomer 1, Example 17A) and (2S,3R)-2-(4-tert-butylphenyl)-4,4,4-trifluoro-3-methylbutanoic acid | LC-MS (Method 5):<br>$R_t$ = 1.52 min; m/z = 526/528 (M + H)$^+$.<br>$^1$H-NMR (400 MHz, DMSO-d$_6$): δ [ppm] = 0.68 (d, 3H), 0.79 (d, 3H), 0.85 (d, 3H), 1.27 (s, 9H), 1.70-1.84 (m, 1H), 2.46-2.58 (m, 1H, partially obscured by DMSO signal), 2.70-2.80 (m, 2H), 3.28-3.39 (m, 1H, partially obscured by H2O signal), 3.42 (s, 3H), 4.08 (d, 1H), 6.98 (dd, 1H), 7.31-7.43 (m, 6H), 9.72 (s, 0.96H, major diastereomer), 9.86 (s, 0.04H, minor diastereomer) (92% de). |

| Example | Name/Structure/Starting materials | Analytical data |
|---|---|---|
| 114A | methyl 3-(4-chloro-3-{[(2S,3R)-2-(4-chloro-3-methoxyphenyl)-4,4,4-trifluoro-3-methyl-butanoyl]amino}phenyl)-4-methylpentanoate (diastereomer 1)<br>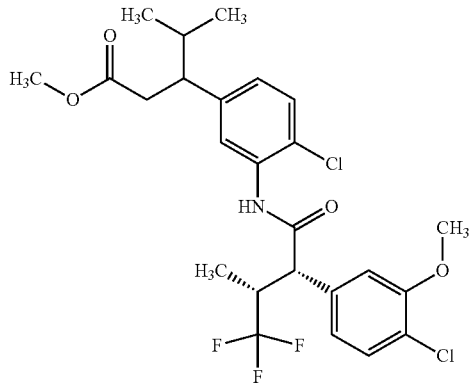<br>from methyl 3-(3-amino-4-chlorophenyl)-4-methyl-pentanoate (enantiomer 1, Example 17A) and (2S,3R)-2-(4-chloro-3-methoxyphenyl)-4,4,4-trifluoro-3-methylbutanoic acid | LC-MS (Method 4):<br>$R_t$ = 2.91 min; m/z = 534-536 $(M + H)^+$. |
| 115A | methyl 3-(4-chloro-3-{[(2S,3R)-4,4,4-trifluoro-3-methyl-2-(4-methylphenyl)butanoyl]amino}-phenyl)-4-methylpentanoate (diastereomer 1)<br>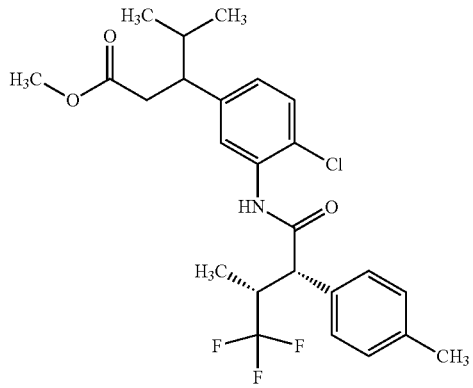<br>from methyl 3-(3-amino-4-chlorophenyl)-4-methyl-pentanoate (enantiomer 1, Example 17A) and (2S,3R)-4,4,4-trifluoro-3-methyl-2-(4-methyl-phenyl)butanoic acid | LC-MS (Method 5):<br>$R_t$ = 1.40 min; m/z = 484/486 $(M + H)^+$.<br>$^1$H-NMR (400 MHz, DMSO-$d_6$): δ [ppm] = 0.68 (d, 3H), 0.79 (d, 3H), 0.85 (d, 3H), 1.70-1.84 (m, 1H), 2.29 (s, 3H), 2.48-2.57 (m, 1H, obscured by DMSO signal), 2.70-2.80 (m, 2H), 3.29-3.40 (m, 1H, partially obscured by H$_2$O signal), 3.42 (s, 3H), 4.05 (d, 1H), 6.99 (dd, 1H), 7.18 (d, 2H), 7.29-7.38 (m, 4H), 9.73 (s, 0.94H, major diastereomer), 9.87 (s, 0.06H, minor diastereomer) (88% de). |

-continued

| Example | Name/Structure/Starting materials | Analytical data |
|---|---|---|
| 116A | methyl 3-(4-chloro-3-{[(2S,3R)-2-(4-chloro-3-methylphenyl)-4,4,4-trifluoro-3-methylbutanoyl]-amino}phenyl)-4-methylpentanoate (diastereomer 1)<br><br>from methyl 3-(3-amino-4-chlorophenyl)-4-methylpentanoate (enantiomer 1, Example 17A) and (2S,3R)-2-(4-chloro-3-methylphenyl)-4,4,4-trifluoro-3-methylbutanoic acid | LC-MS (Method 5):<br>$R_t$ = 1.51 min; m/z = 518/520 $(M + H)^+$.<br>$^1$H-NMR (400 MHz, DMSO-$d_6$): δ [ppm] = 0.68 (d, 3H), 0.81 (d, 3H), 0.85 (d, 3H), 1.70-1.83 (m, 1H), 2.23 (s, 3H), 2.45-2.59 (m, 1H, partially obscured by DMSO signal), 2.70-2.81 (m, 2H), 3.28-3.41 (m, 1H, partially obscured by H$_2$O signal), 3.42 (s, 3H), 4.07 (d, 1H), 7.00 (dd, 1H), 7.27-7.45 (m, 5H), 9.81 (s, 0.94H, major diastereomer), 9.89 (s, 0.06H, minor diastereomer) (88% de). |
| 117A | methyl 3-(4-chloro-3-{[(4-chlorophenyl)-(3,3-difluorocyclopentyl)acetyl]amino}phenyl)-4-methylpentanoate (isomer 1)<br><br>from methyl 3-(3-amino-4-chlorophenyl)-4-methylpentanoate (enantiomer 1, Example 17A) and (4-chlorophenyl)(3,3-difluorocyclopentyl)acetic acid (isomer 1) | LC-MS (Method 5):<br>$R_t$ = 1.41 min; m/z = 512/514 $(M + H)^+$.<br>$^1$H-NMR (400 MHz, DMSO-$d_6$): δ [ppm] = 0.67 (d, 3H), 0.85 (d, 3H), 1.52-1.70 (m, 2H), 1.72-1.82 (m, 1H), 1.82-1.95 (m, 1H), 1.98-2.30 (m, 3H), 2.46-2.60 (m, 1H, partially obscured by DMSO signal), 2.70-2.80 (m, 2H), 2.80-2.93 (m, 1H), 3.43 (s, 3H), 3.78 (d, 1H), 7.02 (dd, 1H), 7.33 (d, 1H), 7.37 (d, 1H), 7.44 (q, 4H), 9.78 (s, 1H). |

-continued

| Example | Name/Structure/Starting materials | Analytical data |
|---|---|---|
| 118A | methyl 3-(4-chloro-3-{[(4-chlorophenyl)-(3,3-difluorocyclopentyl)acetyl]amino}phenyl)-4-methylpentanoate (isomer 2)<br>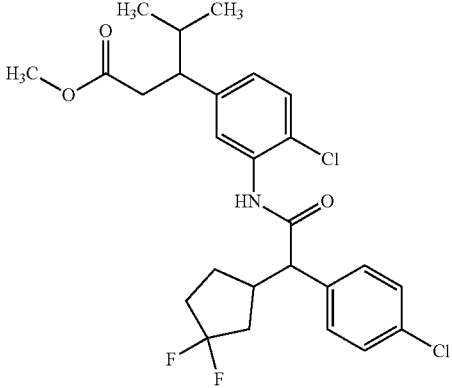<br>from methyl 3-(3-amino-4-chlorophenyl)-4-methylpentanoate (enantiomer 1, Example 17A) and (4-chlorophenyl)(3,3-difluorocyclopentyl)acetic acid (isomer 2) | LC-MS (Method 5):<br>$R_t$ = 1.41 min; m/z = 512/514 $(M + H)^+$.<br>$^1$H-NMR (400 MHz, DMSO-$d_6$): δ [ppm] = 0.67 (d, 3H), 0.85 (d, 3H), 1.52-1.69 (m, 2H), 1.72-1.81 (m, 1H), 1.81-1.96 (m, 1H), 1.98-2.30 (m, 3H), 2.46-2.60 (m, 1H, partially obscured by DMSO signal), 2.70-2.80 (m, 2H), 2.80-2.93 (m, 1H), 3.43 (s, 3H), 3.78 (d, 1H), 7.02 (dd, 1H), 7.34 (d, 1H), 7.36 (d, 1H), 7.44 (q, 4H), 9.78 (s, 1H). |
| 119A | methyl 3-(4-chloro-3-{[(4-chlorophenyl)-(3,3-difluorocyclopentyl)acetyl]amino}phenyl)-4-methylpentanoate (isomer 3)<br>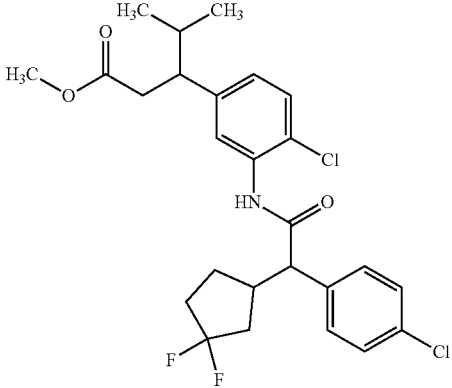<br>from methyl 3-(3-amino-4-chlorophenyl)-4-methylpentanoate (enantiomer 1, Example 17A) and (4-chlorophenyl)(3,3-difluorocyclopentyl)acetic acid (isomer 3) | LC-MS (Method 5):<br>$R_t$ = 1.42 min; m/z = 512/514 $(M + H)^+$.<br>$^1$H-NMR (400 MHz, DMSO-$d_6$): δ [ppm] = 0.67 (d, 3H), 0.85 (d, 3H), 1.21-1.35 (m, 1H), 1.45-1.58 (m, 1H), 1.72-1.83 (m, 1H), 1.85-2.20 (m, 3H), 2.28-2.43 (m, 1H), 2.47-2.60 (m, 1H, partially obscured by DMSO signal), 2.70-2.90 (m, 3H), 3.44 (s, 3H), 3.75 (d, 1H), 7.02 (dd, 1H), 7.33 (d, 1H), 7.37 (d, 1H), 7.44 (q, 4H), 9.74 (s, 1H). |

| Example | Name/Structure/Starting materials | Analytical data |
|---|---|---|
| 120A | methyl 3-(4-chloro-3-{[(4-chlorophenyl)-(3,3-difluorocyclopentyl)acetyl]amino}phenyl)-4-methylpentanoate (isomer 4)<br>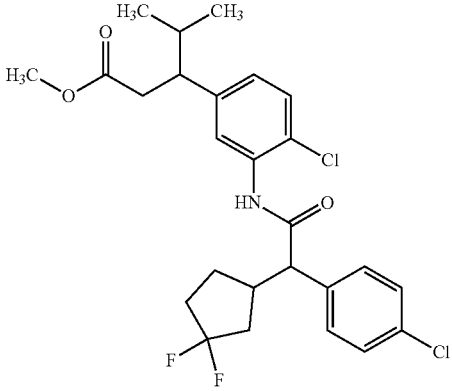<br>from methyl 3-(3-amino-4-chlorophenyl)-4-methylpentanoate (enantiomer 1, Example 17A) and (4-chlorophenyl)(3,3-difluorocyclopentyl)acetic acid (isomer 4) | LC-MS (Method 5): $R_t$ = 1.42 min; m/z = 512/514 $(M + H)^+$.<br>$^1$H-NMR (400 MHz, DMSO-$d_6$): δ [ppm] = 0.68 (d, 3H), 0.86 (d, 3H), 1.21-1.35 (m, 1H), 1.45-1.58 (m, 1H), 1.71-1.83 (m, 1H), 1.85-2.20 (m, 3H), 2.29-2.44 (m, 1H), 2.46-2.61 (m, 1H, partially obscured by DMSO signal), 2.70-2.90 (m, 3H), 3.43 (s, 3H), 3.75 (d, 1H), 7.02 (dd, 1H), 7.34 (d, 1H), 7.36 (d, 1H), 7.44 (q, 4H), 9.74 (s, 1H). |

Example 121A

Methyl 3-(4-chloro-3-{[(2S,3R)-2-(4-chlorophenyl)-4,4,4-trifluoro-3-methylbutanoyl]amino}-phenyl)-3-(2,2-difluorocyclopropyl)propanoate and methyl 3-(4-chloro-3-{[(2S,3R)-2-(4-chlorophenyl)-4,4,4-trifluoro-3-methylbutanoyl]amino}-phenyl)-5,5-difluorohexanoate

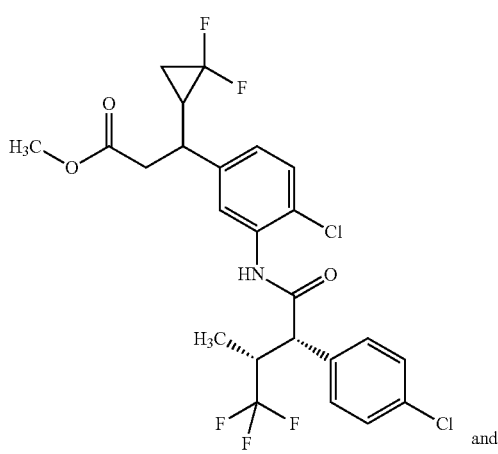

and

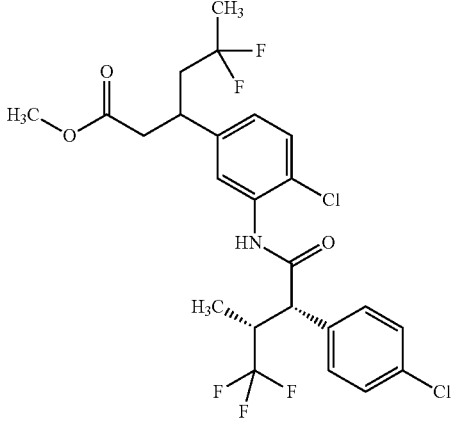 [SMILES: COC(=O)CC(CC(C)(F)F)c1ccc(Cl)c(NC(=O)[C@H](c2ccc(Cl)cc2)[C@@H](C)C(F)(F)F)c1]

330 mg (1.24 mmol) of (2S,3R)-2-(4-chlorophenyl)-4,4,4-trifluoro-3-methylbutanoic acid were dissolved in 10 ml of dichloromethane, 264 mg (1.98 mmol) of 1-chloro-N,N,2-trimethylprop-1-ene-1-amine were added and the mixture was stirred at room temperature for 30 min. 300 (3.71 mmol) of pyridine and 360 mg of the mixture consisting of methyl 3-(3-amino-4-chlorophenyl)-3-(2,2-difluorocyclopropyl)propanoate and methyl 3-(3-amino-4-chlorophenyl)-5,5-difluorohexanoate (Example 59A), dissolved in 1 ml of dichloromethane, were then added, and the reaction mixture was stirred for a further 1 h. The reaction mixture was then concentrated under reduced pressure and the crude product obtained was directly purified chromatographically on silica gel (mobile phase cyclohexane/ethyl acetate 20:1). This gave 479 mg of the mixture of the two target compounds.

LC-MS (Method 5): $R_t$=1.33 min; m/z=538/540/542 (MA-1)$^+$.

Examples 122A-125A 476 mg of the mixture of methyl 3-(4-chloro-3-{[(2S,3R)-2-(4-chlorophenyl)-4,4,4-trifluoro-3-methylbutanoyl]amino}phenyl)-3-(2,2-difluorocyclopropyl)propanoate and methyl 3-(4-chloro-3-{[(2S,3R)-2-(4-chlorophenyl)-4,4,4-trifluoro-3-methylbutanoyl]amino}phenyl)-5,5-difluorohexanoate (Example 121A) were separated further by preparative HPLC on a chiral phase [column: Daicel Chiralpak AZ-H, 5 μm, 250 mm×20 mm; mobile phase: isohexane/isopropanol 95:5 (v/v); flow rate: 15 ml/min; UV detection: 220 nm; temperature: 30° C.]. The material initially obtained for peak 2 and peak 3 was combined and then separated by another preparative HPLC on a chiral phase [column: Daicel Chiralpak AD-H, 5 μm, 250 mm×20 mm; mobile phase: isohexane/isopropanol 95:5 (v/v); flow rate: 15 ml/min; UV detection: 220 nm; temperature: 30° C.].

Example 122A

Methyl 3-(4-chloro-3-{[(2S,3R)-2-(4-chlorophenyl)-4,4,4-trifluoro-3-methylbutanoyl]amino}-phenyl)-5,5-difluorohexanoate (diastereomer 1)

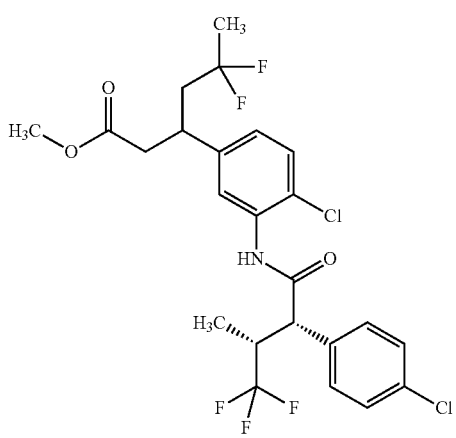

Yield: 100 mg $R_t$=8.42 min; chemical purity >99%, >99% de

[Column: Daicel AZ-H, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 30° C.].

LC-MS (Method 5): $R_t$=1.33 min; m/z=540/542 (M+H)$^+$.

$^1$H-NMR (400 MHz, DMSO-d$_6$): δ [ppm]=0.80 (d, 3H), 1.46 (t, 3H), 2.19-2.32 (m, 2H), 2.46-2.60 (m, 1H, partially obscured by DMSO signal), 2.69-2.78 (m, 1H), 3.20-3.30 (m, 1H), 3.30-3.43 (m, 1H, obscured by H$_2$O signal), 3.48 (s, 3H), 4.12 (d, 1H), 7.14 (dd, 1H), 7.37 (d, 1H), 7.42 (d, 1H), 7.43-7.50 (m, 4H), 9.84 (s, 1H).

Example 123A

Methyl 3-(4-chloro-3-{[(2S,3R)-2-(4-chlorophenyl)-4,4,4-trifluoro-3-methylbutanoyl]amino}-phenyl)-5,5-difluorohexanoate (Diastereomer 2)

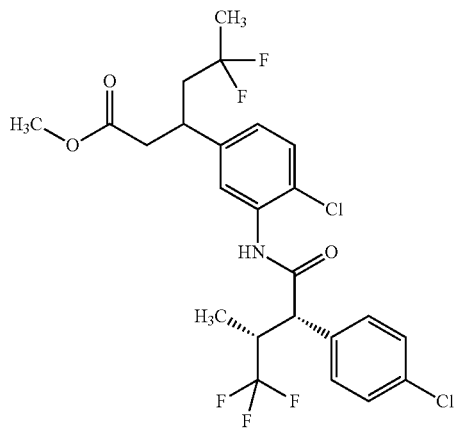 [SMILES: COC(=O)CC(CC(C)(F)F)c1ccc(Cl)c(NC(=O)[C@H](c2ccc(Cl)cc2)[C@@H](C)C(F)(F)F)c1]

Yield: 96 mg $R_t$=10.14 min; chemical purity >94%, >99% de

[Column: Daicel AZ-H, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 30° C.].

LC-MS (Method 5): $R_t$=1.33 min; m/z=540/542 (M+H)$^+$.

$^1$H-NMR (400 MHz, DMSO-d$_6$): δ [ppm]=0.80 (d, 3H), 1.47 (t, 3H), 2.19-2.32 (m, 2H), 2.46-2.60 (m, 1H, partially obscured by DMSO signal), 2.69-2.78 (m, 1H), 3.20-3.30 (m, 1H), 3.30-3.43 (m, 1H, obscured by H$_2$O signal), 3.46 (s, 3H), 4.12 (d, 1H), 7.14 (dd, 1H), 7.37 (d, 1H), 7.41 (d, 1H), 7.43-7.50 (m, 4H), 9.84 (s, 1H).

Example 124A

Methyl 3-(4-chloro-3-{[(2S,3R)-2-(4-chlorophenyl)-4,4,4-trifluoro-3-methylbutanoyl]amino}-phenyl)-3-(2,2-difluorocyclopropyl)propanoate (Isomer 1)

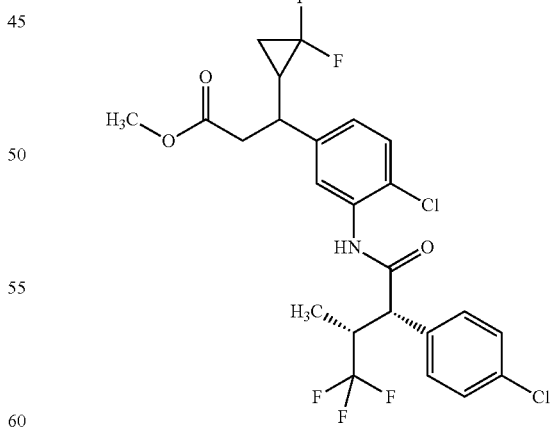

Yield: 124 mg $R_t$=9.00 min; chemical purity >96%

[Column: Daicel AZ-H, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 30° C.].

LC-MS (Method 5): R$_t$=1.34 min; m/z=538/540 (M+H)$^+$.
$^1$H-NMR (400 MHz, DMSO-d$_6$): δ [ppm]=0.80 (d, 3H), 1.06-1.18 (m, 1H), 1.38-1.51 (m, 1H), 2.01-2.16 (m, 1H), 2.64-2.82 (m, 3H), 3.28-3.54 (m, 1H, partially obscured by H$_2$O signal), 3.50 (s, 3H), 4.12 (d, 1H), 7.22 (dd, 1H), 7.41 (d, 1H), 7.43-7.50 (m, 5H), 9.88 (s, 1H).

Example 125A

Methyl 3-(4-chloro-3-{[(2S,3R)-2-(4-chlorophenyl)-4,4,4-trifluoro-3-methylbutanoyl]amino}-phenyl)-3-(2,2-difluorocyclopropyl)propanoate (Isomer 2)

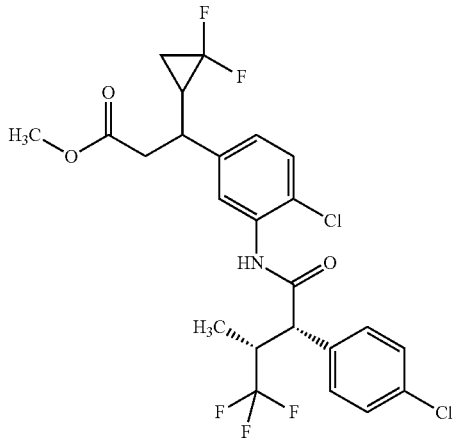 [SMILES: COC(=O)CC(c1ccc(Cl)c(NC(=O)[C@H](c2ccc(Cl)cc2)[C@@H](C)C(F)(F)F)c1)C1CC1(F)F]

Yield: 118 mg
R$_t$=9.47 min; chemical purity >99%
[Column: Daicel AZ-H, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 30° C.].
LC-MS (Method 5): R$_t$=1.33 min; m/z=538/540 (M+H)$^+$.
$^1$H-NMR (400 MHz, DMSO-d$_6$): δ [ppm]=0.80 (d, 3H), 1.06-1.18 (m, 1H), 1.38-1.52 (m, 1H), 2.01-2.15 (m, 1H), 2.63-2.83 (m, 3H), 3.28-3.58 (m, 1H, partially obscured by H$_2$O signal), 3.49 (s, 3H), 4.12 (d, 1H), 7.21 (dd, 1H), 7.40 (d, 1H), 7.42-7.50 (m, 5H), 9.87 (s, 1H).

Example 126A tert-Butyl 3-(4-chloro-3-{[(2S,3R)-2-(4-chlorophenyl)-4,4,4-trifluoro-3-methylbutanoyl]amino}-phenyl)-3-(3,3-difluorocyclobutyl)propanoate (Diastereomer Mixture)

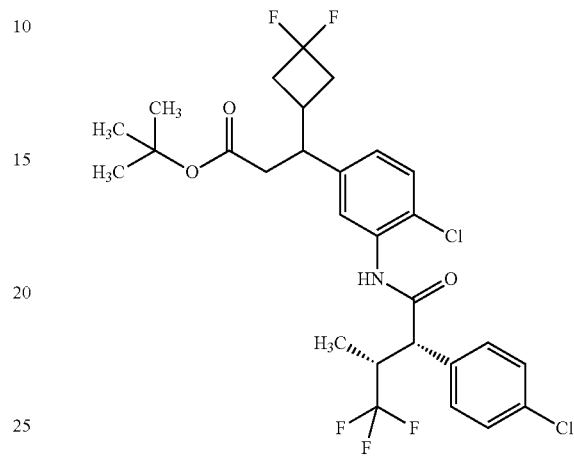

A solution of 76 mg (0.29 mmol) of (2S,3R)-2-(4-chlorophenyl)-4,4,4-trifluoro-3-methylbutanoic acid, 45 mg (0.13 mmol) of tert-butyl 3-(3-amino-4-chlorophenyl)-3-(3,3-difluorocyclobutyl)-propanoate, 119 mg (0.31 mmol) of O-(1H-7-azabenzotriazol-1-yl)-N,N,N',N'-tetramethyluronium hexafluorophosphate (HATU) and 0.51 ml of pyridine in 1 ml of DMF was stirred at room temperature overnight. After the reaction had ended, the mixture was directly, without further work-up, separated into its components by preparative HPLC. This gave 19 mg (25% of theory) of the title compound as a colourless oil.
LC-MS (Method 5): R$_t$=1.47 min; m/z=592/594 (M–H)$^-$.
The compounds listed in the table below were prepared in an analogous manner:

| Example | Name/Structure/Starting materials | Analytical data |
|---|---|---|
| 127A | tert-butyl 3-(4-chloro-3-{[(2S,3R)-2-(4-chlorophenyl)-4,4,4-trifluoro-3-methylbutanoyl]amino}-phenyl)-3-cyclobutylpropanoate (diastereomer mixture)<br><br>from (+/-)-tert-butyl 3-(3-amino-4-chlorophenyl)-3-cyclobutylpropanoate and (+)-(2S,3R)-2-(4-chlorophenyl)-4,4,4-trifluoro-3-methylbutanoic acid | LC-MS (Method 5):<br>R$_t$ = 1.57 min; m/z = 556 (M – H)$^-$.<br>$^1$H-NMR (400 MHz, DMSO-d$_6$): both diastereomers: δ [ppm] = 0.80 (d, 3H), 1.15/1.18 (2s, together 9H), 1.46-1.62 (m, 2H), 1.62-1.76 (m, 3H), 1.96-2.06 (m, 1H), 2.16-2.28 (m, 1H), 2.32-2.48 (m, 2H), 2.76-2.87 (m, 1H), 3.35-3.45 (m, 1H), 4.13-4.14 (2d, together 1H), 7.00 (dt, 1H), 7.34 (d, 1H), 7.36-7.53 (m, 5H), 9.79/9.80 (2s, together 1H). |

| Example | Name/Structure/Starting materials | Analytical data |
|---|---|---|
| 128A | tert-butyl 3-(4-chloro-3-{[(2S,3R)-2-(4-chloro-phenyl)-4,4,4-trifluoro-3-methylbutanoyl]amino}-phenyl)-4-cyclopropylbutanoate (diastereomer mixture)<br>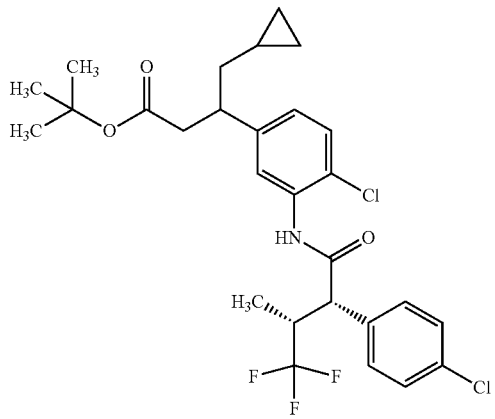<br>from tert-butyl 3-(3-amino-4-chlorophenyl)-4-cyclopropylbutanoate and (+)-(2S,3R)-2-(4-chlorophenyl)-4,4,4-trifluoro-3-methylbutanoic acid | LC-MS (Method 5):<br>$R_t$ = 1.62 min; m/z = 556/558 (M − H)⁻. |
| 129A | ethyl 3-(4-chloro-3-{[(2S,3R)-2-(4-chlorophenyl)-4,4,4-trifluoro-3-methylbutanoyl]amino}phenyl)-3-cyclopropyl-2-methylpropanoate (diastereomer mixture)<br>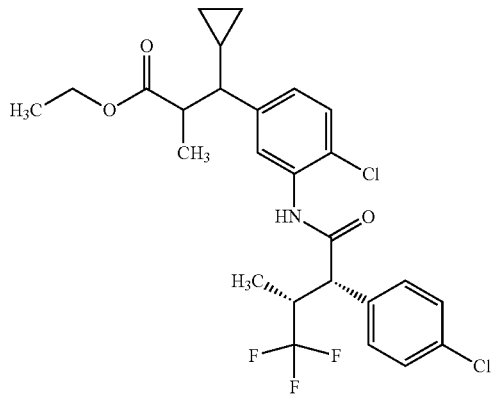<br>from ethyl 3-(3-amino-4-chlorophenyl)-3-cyclopropyl-2-methylpropanoat (diastereomer mixture) and (+)-(2S,3R)-2-(4-chlorophenyl)-4,4,4-trifluoro-3-methylbutanoic acid | LC-MS (Method 7):<br>$R_t$ = 1.49 min; m/z = 530/532 (M + H)⁺. |

| Example | Name/Structure/Starting materials | Analytical data |
|---|---|---|
| 130A | methyl 3-(4-chloro-3-{[(2S,3R)-2-(4-chlorophenyl)-4,4,4-trifluoro-3-methylbutanoyl]amino}phenyl)-3-cyclopropylbutanoate (diastereomer mixture)<br>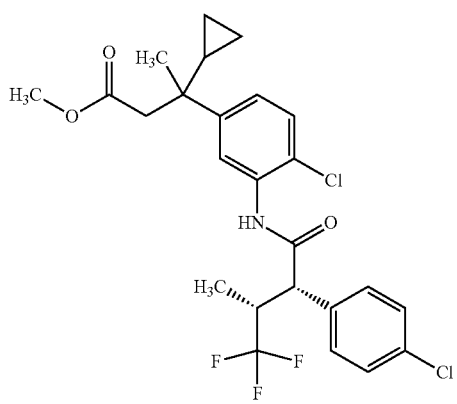<br>from methyl 3-(3-amino-4-chlorophenyl)-3-cyclopropylbutanoate (racemate) and (+)-(2S,3R)-2-(4-chlorophenyl)-4,4,4-trifluoro-3-methylbutanoic acid | LC-MS (Method 5):<br>$R_t$ = 1.41 min; m/z = 516/518 (M + H)$^+$. |

Example 131A

2-(1-Methylcyclopropyl)ethanol

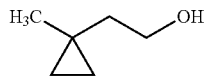

11.23 g (87.1 mmol) of zinc/copper pair were taken up in 50 ml of diethyl ether, and 6.76 ml (92.9 mmol) of chloroiodomethane were added at room temperature. 5.84 ml (58.1 mmol) of 3-methylbut-3-en-1-ol, dissolved in 10 ml of diethyl ether, were then added dropwise. After the addition had ended, the reaction mixture was heated to 40° C. and stirred at this temperature overnight. After cooling, the reaction was filtered off with suction through kieselguhr, and the kieselguhr was washed repeatedly with diethyl ether. The combined filtrates were washed with saturated aqueous sodium bicarbonate solution and with water, dried over magnesium sulphate and then concentrated to dryness under reduced pressure. The residue obtained was purified by chromatography on silica gel (mobile phase cyclohexane/ethyl acetate 10:1). This gave 3.58 g (62% of theory) of the title compound.

GC-MS (Method 1): $R_t$=1.23 min; m/z=100 (M)$^+$.

$^1$H-NMR (400 MHz, DMSO-d$_6$): δ [ppm]=0.24-0.29 (m, 2H), 0.29-0.34 (m, 2H), 1.05 (s, 3H), 1.37 (t, 1H), 1.53 (t, 2H), 3.74-3.80 (m, 2H).

The following compound was obtained analogously to Synthesis Example 1A:

| Example | Name/Structure/Starting materials | Analytical data |
|---|---|---|
| 132A | tert-butyl (2E)-4-(1-methylcyclopropyl)-but-2-enoate<br>from tert-butyl (triphenyl-λ$^5$-phosphanylidene)-acetate and 2-(1-methylcyclopropyl)ethanol | GC-MS (Method 6):<br>$R_t$ = 3.86 min; m/z = 214 (M + NH$_4$)$^+$.<br>$^1$H-NMR (400 MHz, DMSO-d$_6$):<br>δ [ppm] = 0.25-0.31 (m, 2H), 0.31-0.37 (m, 2H), 0.98 (s, 3H), 1.43 (s, 9H), 2.06-2.11 (m, 2H), 5.76-5.83 (m, 1H), 6.72-6.82 (m, 1H). |

The following compound was obtained analogously to Synthesis Example 4A/5A:

| Example | Name/Structure/Starting materials | Analytical data |
|---|---|---|
| 133A | tert-butyl (2E/Z)-3-(3-amino-4-chlorophenyl)-4-(1-methylcyclopropyl)but-2-enoate<br>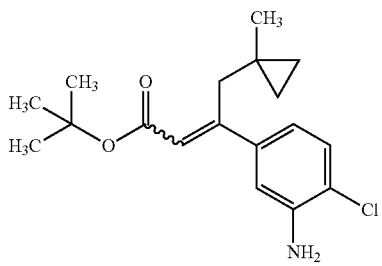<br>from tert-butyl (2E)-4-(1-methylcyclopropyl)-but-2-enoate and 5-bromo-2-chloroaniline | LC-MS (Method 5):<br>$R_t$ = 1.42 min; m/z = 322 (M + H)$^+$.<br>$^1$H-NMR (400 MHz, DMSO-d$_6$):<br>δ [ppm] = 0.04-0.10 (m, 2H), 0.17-0.24 (m, 2H), 0.85 (s, 3H), 1.46 (s, 9H), 3.02 (s, 2H), 5.40 (br. s, 2H), 5.82 (s, 1H), 6.62 (dd, 1H), 6.88 (d, 1H), 7.17 (d, 1H). |

Example 134A tert-Butyl 3-(3-amino-4-chlorophenyl)-4-(1-methylcyclopropyl)butanoate

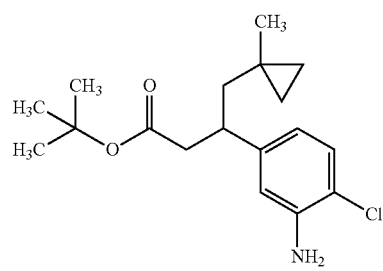 [SMILES: CC1(CC(CC(=O)OC(C)(C)C)c2ccc(Cl)c(N)c2)CC1]

187 mg (0.58 mmol) of tert-butyl (2E/Z)-3-(3-amino-4-chlorophenyl)-4-(1-methylcyclopropyl)but-2-enoate were dissolved in 10 ml of ethyl acetate, and 11 mg (0.06 mmol) of platinum(IV) oxide were added. At RT, the reaction mixture was stirred under an atmosphere of hydrogen at atmospheric pressure overnight. Another 11 mg (0.06 mmol) of platinum(IV) oxide were added, and the mixture was then once more stirred at RT under an atmosphere of hydrogen at atmospheric pressure overnight. The reaction mixture was then filtered off with suction through kieselguhr, and the filtrate was concentrated. This gave 36 mg (19% of theory) of the target compound.

LC-MS (Method 5): $R_t$=1.37 min; m/z=324 (M+H)$^+$.

$^1$H-NMR (400 MHz, DMSO-d$_6$): δ [ppm]=−0.10-0.03 (m, 1H), −0.03-0.04 (m, 1H), 0.13-0.25 (m, 2H), 0.95 (s, 3H), 1.27 (s, 9H), 1.40-1.52 (m, 2H), 2.24-2.33 (m, 1H), 2.47-2.58 (m, 1H, partially obscured by DMSO signal), 2.95-3.05 (m, 1H), 5.19 (br. s, 2H), 6.41 (dd, 1H), 6.65 (d, 1H), 7.05 (d, 1H).

The following compound was prepared analogously to Synthesis Example 99A:

| Example | Name/Structure/Starting materials | Analytical data |
|---|---|---|
| 135A | tert-butyl 3-(4-chloro-3-{[(2S,3R)-2-(4-chloro-phenyl)-4,4,4-trifluoro-3-methylbutanoyl]amino}-phenyl)-4-(1-methylcyclopropyl)butanoate (diastereomer mixture)<br>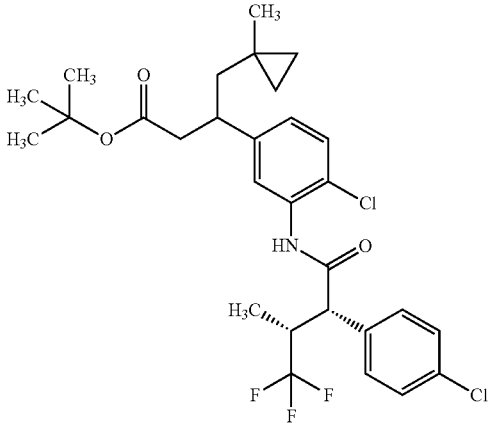<br>from tert-butyl 3-(3-amino-4-chlorophenyl)-4-(1-methylcyclopropyl)butanoate and (2S,3R)-2-(4-chlorophenyl)-4,4,4-trifluoro-3-methylbutanoic acid | LC-MS (Method 8): $R_t$ = 3.27 min; m/z = 570/571 (M − H)⁻.<br>$^1$H-NMR (400 MHz, DMSO-$d_6$): δ [ppm] = −0.14−−0.07 (m, 1H), −0.07-0.02 (m, 1H), 0.12-0.19 (m, 1H), 0.19-0.25 (m, 1H), 0.80 (d, 3H), 0.93 (d, 3H), 1.19 (2s, 9H), 1.39-1.55 (m, 2H), 2.26-2.38 (m, 1H), 2.48-2.63 (m, 1H, partially obscured by DMSO signal), 3.05-3.16 (m, 1H), 3.29-3.44 (m, 1H, partially obscured by H₂O signal), 4.14 (dd, 1H), 7.06 (d, 1H), 7.34 (d, 1H), 7.39-7.51 (m, 5H), 9.80 (d, 1H). |

Working Examples:

Example 1

(+)-3-(4-Chloro-3-{[(2S,3R)-2-(4-chlorophenyl)-4,4,4-trifluoro-3-methylbutanoyl]amino}phenyl)-4-methylpentanoic acid (Diastereomer 1)

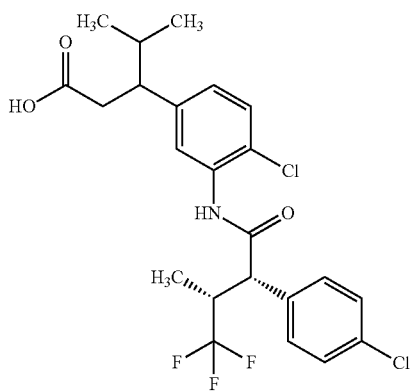 [SMILES: CC(C)C(CC(=O)O)c1ccc(Cl)c(NC(=O)[C@H](c2ccc(Cl)cc2)[C@@H](C)C(F)(F)F)c1]

4 ml of concentrated acetic acid and 2 ml of concentrated hydrochloric acid were added to 225 mg (0.45 mmol) of methyl 3-(4-chloro-3-{[(2S,3R)-2-(4-chlorophenyl)-4,4,4-trifluoro-3-methylbutanoyl]amino}phenyl)-4-methylpentanoate (diastereomer 1; Example 96A). The reaction mixture was stirred at 100° C. for 2 h. After cooling, the reaction mixture was added to ice-water, and the crystals formed were filtered off with suction. The crystals were washed twice with water and then dried in a high vacuum drying cabinet at 40° C. overnight. This gave 193 mg (88% of theory) of the title compound as a white solid.

LC-MS (Method 7): $R_t$=1.30 min; m/z=490/492 (M+H)⁺.
$^1$H-NMR (400 MHz, DMSO-$d_6$): δ [ppm]=0.68 (d, 3H), 0.80 (d, 3H), 0.84 (d, 3H), 1.70-1.80 (m, 1H), 2.36-2.48 (m, 1H), 2.61-2.70 (m, 1H), 2.70-2.80 (m, 1H), 3.29-3.43 (m, 1H, partially obscured by H₂O signal), 4.13 (d, 1H), 7.00 (dd, 1H), 7.31-7.37 (m, 2H), 7.43-7.50 (m, 4H), 9.82 (s, 1H), 11.95 (br. s, 1H).
$[α]_D^{20}$=+111°, c=0.285, methanol.

Example 2

(+)-3-(4-Chloro-3-{[(2S,3R)-2-(4-chlorophenyl)-4,4,4-trifluoro-3-methylbutanoyl]amino}phenyl)-4-methylpentanoic acid (Diastereomer 2)

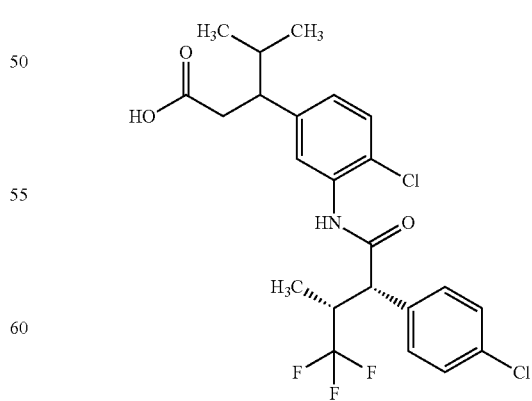

4 ml of concentrated acetic acid and 2 ml of concentrated hydrochloric acid were added to 218 mg (0.43 mmol) of methyl 3-(4-chloro-3-{[(2S,3R)-2-(4-chlorophenyl)-4,4,4- trifluoro-3-methylbutanoyl]amino}phenyl)-4-methylpentanoate (diastereomer 2; Example 97A). The reaction mixture was stirred at 100° C. for 2 h. After cooling, the reaction mixture was added to ice-water, and the crystals formed were filtered off with suction. The crystals were washed twice with water and then dried in a high vacuum drying cabinet at 40° C. overnight. This gave 188 mg (89% of theory) of the title compound as a white solid.

LC-MS (Method 7): $R_t$=1.30 min; m/z=490/492 (M+H)$^+$.

$^1$H-NMR (400 MHz, DMSO-d$_6$): δ [ppm]=0.67 (d, 3H), 0.80 (d, 3H), 0.84 (d, 3H), 1.69-1.80 (m, 1H), 2.39-2.48 (m, 1H), 2.62-2.70 (m, 1H), 2.71-2.79 (m, 1H), 3.29-3.44 (m, 1H, partially obscured by H$_2$O signal), 4.13 (d, 1H), 7.00 (dd, 1H), 7.32-7.38 (m, 2H), 7.41-7.51 (m, 4H), 9.82 (s, 1H), 11.96 (br. s, 1H).

$[α]_D^{20}$=+82°, c=0.275, methanol.

The compounds listed in the table below were prepared in an analogous manner:

| Example | Name/Structure/Starting material | Analytical data |
|---|---|---|
| 3 | 3-(4-chloro-3-{[(2S,3R)-2-(4-chlorophenyl)-4,4,4-trifluoro-3-methylbutanoyl]amino}phenyl)-3,4-dimethylpentanoic acid (diastereomer 1)<br><br>from methyl 3-(4-chloro-3-{[(2S,3R)-2-(4-chlorophenyl)-4,4,4-trifluoro-3-methylbutanoyl]amino}-phenyl)-3,4-dimethylpentanoate (diastereomer 1) | LC-MS (Method 5):<br>$R_t$ = 1.30 min; m/z = 504/506 (M + H)$^+$.<br>$^1$H-NMR (400 MHz, DMSO-d$_6$): δ [ppm] = 0.55 (d, 3H), 0.80 (d, 6H), 1.30 (s, 3H), 1.75-1.88 (m, 1H), 2.46-2.58 (d, 1H, obscured by DMSO signal), 2.69 (d, 1H), 3.28-3.45 (m, 1H, partially obscured by H$_2$O signal), 4.13 (d, 1H), 7.12 (dd, 1H), 7.33 (d, 1H), 7.43-7.51 (m, 5H), 9.81 (s, 1H), 11.75 (br. s, 1H).<br>$[α]_D^{20}$ = +95°, c = 0.285, methanol. |
| 4 | 3-(4-chloro-3-{[(2S,3R)-2-(4-chlorophenyl)-4,4,4-trifluoro-3methylbutanoyl]amino}phenyl)-3,4-dimethylpentanoic acid (diastereomer 2)<br><br>from methyl 3-(4-chloro-3-{[(2S,3R)-2-(4-chlorophenyl)-4,4,4-trifluoro-3-methylbutanoyl]amino}-phenyl)-3,4-dimethylpentanoate (diastereomer 2) | LC-MS (Method 5):<br>$R_S$ = 1.30 min; m/z = 504/506 (M + H)$^+$.<br>$^1$H-NMR (400 MHz, DMSO-d$_6$): δ [ppm] = 0.56 (d, 3H), 0.80 (d, 6H), 1.30 (s, 3H), 1.75-1.89 (m, 1H), 2.46-2.57 (d, 1H, obscured by DMSO signal), 2.69 (d, 1H), 3.29-3.45 (m, 1H, partially obscured by H$_2$O signal), 4.13 (d, 1H), 7.12 (dd, 1H), 7.32 (d, 1H), 7.42-7.48 (m, 4H), 7.49 (d, 1H), 9.81 (s, 1H), 11.75 (br. s, 1H).<br>$[α]_D^{20}$ = +105.7°, c = 0.305, methanol. |

-continued

| Example | Name/Structure/Starting material | Analytical data |
|---|---|---|
| 5 | 3-(4-chloro-3-{[(2S,3R)-2-(4-chlorophenyl)-4,4,4-trifluoro-3-methylbutanoyl]amino}phenyl)-3-cyclobutylbutanoic acid (diastereomer 1)<br><br>from methyl 3-(4-chloro-3-{[(2S,3R)-2-(4-chlorophenyl)-4,4,4-trifluoro-3-methylbutanoyl]amino}-phenyl)-3-cyclobutylbutanoate (diastereomer 1) | LC-MS (Method 5): $R_t$ = 1.32 min; m/z = 516/518 $(M + H)^+$.<br>$^1$H-NMR (400 MHz, DMSO-$d_6$): δ [ppm] = 0.80 (d, 3H), 1.31 (s, 3H), 1.41-1.52 (m, 1H), 1.52-1.66 (m, 3H), 1.66-1.78 (m, 2H), 2.37 (d, 1H), 2.45-2.58 (m, 1H, obscured by DMSO signal), 2.64 (d, 1H), 3.28-3.47 (m, 1H, partially obscured by H$_2$O signal), 4.13 (d, 1H), 7.10 (dd, 1H), 7.33 (d, 1H), 7.40-7.52 (m, 5H), 9.81 (s, 1H), 11.83 (br. s, 1H).<br>$[α]_D^{20}$ = +105°, c = 0.250, methanol. |
| 6 | 3-(4-chloro-3-{[(2S,3R)-2-(4-chlorophenyl)-4,4,4-trifluoro-3-methylbutanoyl]amino}phenyl)-3-cyclobutylbutanoic acid (diastereomer 2)<br><br>from methyl 3-(4-chloro-3-{[(2S,3R)-2-(4-chloro-phenyl)-4,4,4-trifluoro-3-methylbutanoyl]amino}-phenyl)-3-cyclobutylbutanoate (diastereomer 2) | LC-MS (Method 5): $R_t$ = 1.32 min; m/z = 516/518 $(M + H)^+$.<br>$^1$H-NMR (400 MHz, DMSO-$d_6$): δ [ppm] = 0.80 (d, 3H), 1.31 (s, 3H), 1.42-1.52 (m, 1H), 1.52-1.67 (m, 3H), 1.67-1.79 (m, 2H), 2.37 (d, 1H), 2.45-2.58 (m, 1H, obscured by DMSO signal), 2.64 (d, 1H), 3.30-3.47 (m, 1H, partially obscured by H$_2$O signal), 4.13 (d, 1H), 7.10 (dd, 1H), 7.33 (d, 1H), 7.41-7.52 (m, 5H), 9.81 (s, 1H), 11.84 (br. s, 1H).<br>$[α]_D^{20}$ = +100°, c = 0.30, methanol. |

| Example | Name/Structure/Starting material | Analytical data |
|---|---|---|
| 7 | 3-(4-chloro-3-{[(2S,3R)-2-(4-chlorophenyl)-4,4,4-trifluoro-3-methylbutanoyl]amino}phenyl)-3-cyclobutylbutanoic acid (diastereomer mixture)<br>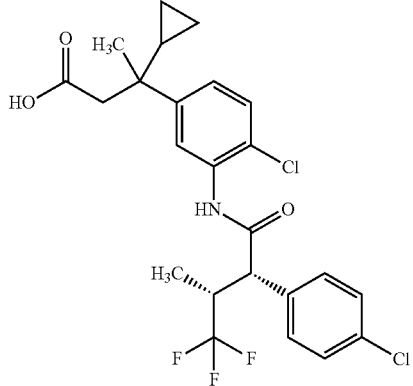<br>from methyl 3-(4-chloro-3-{[(2S,3R)-2-(4-chlorophenyl)-4,4,4-trifluoro-3-methylbutanoyl]amino}-phenyl)-3-cyclopropylbutanoate (diastereomer mixture) | LC-MS (Method 4):<br>$R_t$ = 1.54 min; m/z = 500/502 $(M - H)^-$.<br>$^1$H-NMR (400 MHz, DMSO-$d_6$):<br>δ [ppm] = 0.77-0.85 (m, 5H), 0.87-1.02 (m, 1H), 1.15-1.28 (m, 2H), 1.42 (s, 3H), 2.62-2.72 (m, 1H), 3.01 (d, 1H), 3.28-3.43 (m, 1H, partially obscured by H$_2$O signal), 4.09-4.17 (m, 1H), 7.08 (dd, 1H), 7.38-7.53 (m, 6H), 9.92 (d, 1H). |
| 8 | 3-(4-chloro-3-{[(2S,3R)-2-(4-ethylphenyl)-4,4,4-trifluoro-3-methylbutanoyl]amino}phenyl)-4-methylpentanoic acid (diastereomer 1)<br>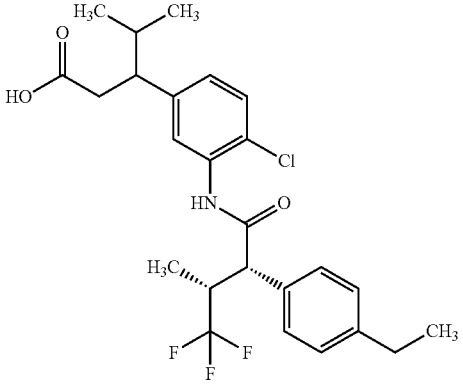<br>from methyl 3-(4-chloro-3-{[(2S,3R)-2-(4-ethyl-phenyl)-4,4,4-trifluoro-3-methylbutanoyl]amino}-phenyl)-4-methylpentanoate (diastereomer 1) | LC-MS (Method 5):<br>$R_t$ = 1.32 min; m/z = 484 $(M + H)^+$.<br>$^1$H-NMR (400 MHz, DMSO-$d_6$):<br>δ [ppm] = 0.68 (d, 3H), 0.79 (d, 3H), 0.84 (d, 3H), 1.17 (t, 3H), 1.68-1.81 (m, 1H), 2.36-2.47 (m, 1H), 2.56-2.69 (m, 3H), 2.70-2.79 (m, 1H), 3.27-3.40 (m, 1H, partially obscured by H$_2$O signal), 4.07 (d, 1H), 6.98 (dd, 1H), 7.20 (d, 2H), 7.30-7.41 (m, 4H), 9.73 (s, 1H), 11.95 (br. s, 1H). |

| Example | Name/Structure/Starting material | Analytical data |
|---|---|---|
| 9 | 3-(4-chloro-3-{[(2S,3R)-2-(4-chloro-3-fluoro-phenyl)-4,4,4-trifluoro-3-methylbutanoyl]-amino}phenyl)-4-methylpentanoic acid (diastereomer 1)<br><br>from methyl 3-(4-chloro-3-{[(2S,3R)-2-(4-chloro-3-fluorophenyl)-4,4,4-trifluoro-3-methylbutanoyl]-amino}phenyl)-4-methylpentanoate (diastereomer 1) | LC-MS (Method 5):<br>$R_t$ = 1.28 min; m/z = 508/510 $(M + H)^+$.<br>$^1$H-NMR (400 MHz, DMSO-$d_6$):<br>δ [ppm] = 0.68 (d, 2.79H, major diastereomer), 0.84 (t, 6H), 1.25 (d, 0.21H, minor diastereomer), 1.69-1.81 (m, 1H), 2.39-2.48 (m, 1H), 2.61-2.70 (m, 1H), 2.70-2.81 (m, 1H), 3.37-3.48 (m, 1H), 4.15 (d, 1H), 7.01 (dd, 1H), 7.29-7.38 (m, 3H), 7.50 (dd, 1H), 7.62 (t, 1H), 9.87 (s, 0.93H, major diastereomer), 10.01 (s, 0.07H, minor diastereomer), 11.96 (br. s, 1H) (86% de). |
| 10 | 3-(4-chloro-3-{[(2S,3R)-4,4,4-trifluoro-2-(4-isopropylphenyl)-3-methylbutanoyl]amino}-phenyl)-4-methylpentanoic acid (diastereomer 1)<br><br>from methyl 3-(4-chloro-3-{[(2S,3R)-4,4,4-trifluoro-2-(4-isopropylphenyl)-3-methyl-butanoyl]amino}phenyl)-4-methylpentanoate (diastereomer 1) | LC-MS (Method 5):<br>$R_t$ = 1.35 min; m/z = 498/500 $(M + H)^+$.<br>$^1$H-NMR (400 MHz, DMSO-$d_6$):<br>δ [ppm] = 0.68 (d, 3H), 0.79 (d, 3H), 0.84 (d, 3H), 1.19 (d, 6H), 1.67-1.80 (m, 1H), 2.36-2.47 (m, 1H), 2.60-2.70 (m, 1H), 2.70-2.79 (m, 1H), 2.81-2.93 (m, 1H), 3.26-3.40 (m, 1H, obscured by H$_2$O signal), 4.07 (d, 1H), 6.98 (dd, 1H), 7.20-7.28 (m, 2H), 7.30-7.43 (m, 4H), 9.73 (s, 1H), 11.95 (br. s, 1H). |

| Example | Name/Structure/Starting material | Analytical data |
|---|---|---|
| 11 | 3-(4-chloro-3-{[(2S,3R)-4,4,4-trifluoro-2-(4-fluorophenyl)-3-methylbutanoyl]amino}-phenyl)-4-methylpentanoic acid (diastereomer 1)<br>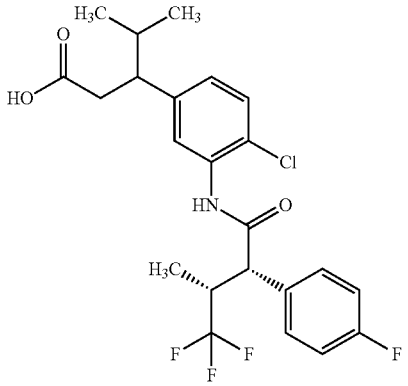<br>from methyl 3-(4-chloro-3-{[(2S,3R)-4,4,4-trifluoro-2-(4-fluorophenyl)-3-methyl-butanoyl]amino}phenyl)-4-methylpentanoate (diastereomer 1) | LC-MS (Method 5):<br>$R_t$ = 1.19 min; m/z = 474/476 $(M + H)^+$.<br>$^1$H-NMR (400 MHz, DMSO-$d_6$):<br>δ [ppm] = 0.68 (d, 2.76H, major diasteromer), 0.80 (d, 3H), 0.84 (d, 3H), 1.25 (d, 0.24H, minor diastereomer), 1.68-1.80 (m, 1H), 2.36-2.47 (m, 1H), 2.60-2.70 (m, 1H), 2.70-2.80 (m, 1H), 3.29-3.44 (m, 1H, partially obscured by H$_2$O signal), 4.12 (d, 1H), 7.00 (dd, 1H), 7.22 (t, 2H), 7.31-7.37 (m, 2H), 7.45-7.52 (m, 2H), 9.80 (s, 0.92H, major diastereomer), 9.94 (s, 0.08H, minor diastereomer), 11.96 (br. s, 1H) (84% de). |
| 12 | 3-(4-chloro-3-({4,4,4-trifluoro-3-methyl-2-[4-(2,2,2-trifluoroethyl)phenyl]butanoyl}-amino)phenyl]-4-methylpentanoic acid (diastereomer mixture)<br>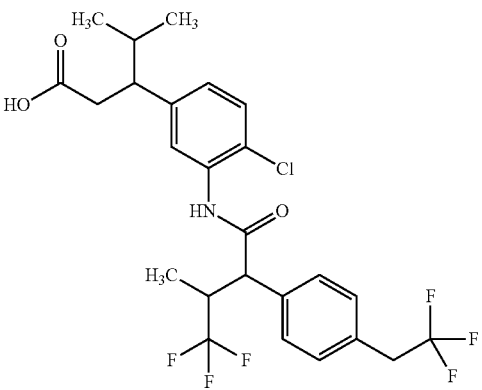<br>from methyl 3-(4-chloro-3-({4,4,4-trifluoro-3-methyl-2-[4-(2,2,2-trifluoroethyl)phenyl]-butanoyl}amino)phenyl]-4-methylpentanoate (diastereomer mixture) | LC-MS (Method 5):<br>$R_t$ = 1.26 min; m/z = 538/540 $(M + H)^+$.<br>$^1$H-NMR (400 MHz, DMSO-$d_6$):<br>δ [ppm] = 0.64-0.71 (m, 3H), 0.79 (d, 3H), 0.84 (d, 3H), 1.68-1.81 (m, 1H), 2.38-2.47 (m, 1H), 2.61-2.69 (m, 1H), 2.70-2.80 (m, 1H), 3.28-3.44 (m, 1H, partially obscured by H$_2$O signal), 3.64 (q, 2H), 4.11 (d, 1H), 6.99 (d, 1H), 7.30-7.39 (m, 4H), 7.46 (d, 2H), 9.80 (s, 1H), 11.95 (br. s, 1H). |

-continued

| Example | Name/Structure/Starting material | Analytical data |
|---|---|---|
| 13 | 3-[4-chloro-3-({(2S,3R)-2-[4-(2,2-difluorocyclo-propyl)phenyl]-4,4,4-trifluoro-3-methylbutanoyl}-amino)phenyl]-4-methylpentanoic acid (diastereomer mixture)<br>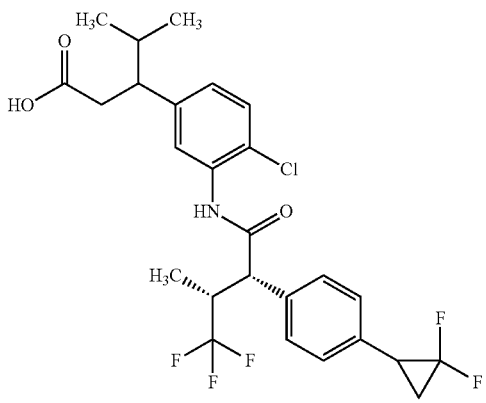<br>from methyl 3-[4-chloro-3-({(2S,3R)-2-[4-(2,2-difluorocyclopropyl)phenyl]-4,4,4-trifluoro-3-methylbutanoyl]amino)phenyl]-4-methylpentanoate (diastereomer mixture) | LC-MS (Method 5):<br>$R_t$ = 1.26 min; m/z = 532/534 $(M + H)^+$.<br>$^1$H-NMR (400 MHz, DMSO-$d_6$): δ [ppm] = 0.68 (d, 3H), 0.79 (d, 3H), 0.84 (d, 3H), 1.68-1.80 (m, 1H), 1.87-2.04 (m, 2H), 2.36-2.47 (m, 1H), 2.61-2.69 (m, 1H), 2.70-2.79 (m, 1H), 2.93-3.06 (m, 1H), 3.29-3.44 (m, 1H, partially obscured by H$_2$O signal), 4.10 (d, 1H), 6.99 (dd, 1H), 7.27 (d, 2H), 7.33 (d, 1H), 7.37 (s, 1H), 7.42 (d, 2H), 9.77 (s, 1H), 11.95 (br. s, 1H). |
| 14 | 3-(3-{[(2S,3R)-2-(4-tert-butylphenyl)-4,4,4-trifluoro-3-methylbutanoyl]amino}-4-chlorophenyl)-4-methylpentanoic acid (diastereomer 1)<br>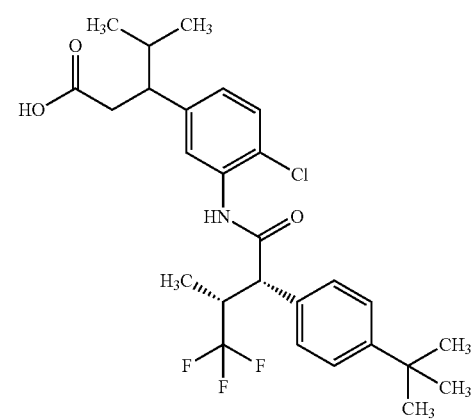<br>from methyl 3-(3-{[(2S,3R)-2-(4-tert-butylphenyl)-4,4,4-trifluoro-3-methylbutanoyl]amino}-4-chlorophenyl)-4-methylpentanoate (diastereomer 1) | LC-MS (Method 5):<br>$R_t$ = 1.39 min; m/z = 512/514 $(M + H)^+$.<br>$^1$H-NMR (400 MHz, DMSO-$d_6$): δ [ppm] = 0.68 (d, 3H), 0.79 (d, 3H), 0.84 (d, 3H), 1.27 (s, 9H), 1.68-1.80 (m, 1H), 2.36-2.47 (m, 1H), 2.60-2.69 (m, 1H), 2.70-2.79 (m, 1H), 3.27-3.43 (m, 1H, partially obscured by H$_2$O signal), 4.08 (d, 1H), 6.97 (dd, 1H), 7.30-7.44 (m, 6H), 9.73 (s, 0.96H, major diastereomer), 9.86 (s, 0.04H, minor diastereomer), 11.95 (br. s, 1H) (92% de). |

-continued

| Example | Name/Structure/Starting material | Analytical data |
|---|---|---|
| 15 | 3-(4-chloro-3-{[(2S,3R)-2-(4-chloro-3-methoxy-phenyl)-4,4,4-trifluoro-3-methylbutanoyl]amino}-phenyl)-4-methylpentanoic acid (diastereomer 1)<br>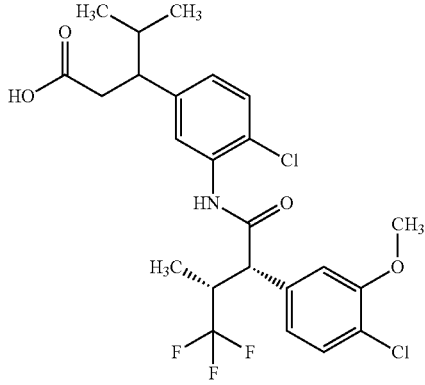<br>from methyl 3-(4-chloro-3-{[(2S,3R)-2-(4-chloro-3-methoxyphenyl)-4,4,4-trifluoro-3-methyl-butanoyl]amino}phenyl)-4-methylpentanoate (diastereomer 1) | LC-MS (Method 5):<br>$R_t$ = 1.24 min; m/z = 520/522 $(M + H)^+$.<br>$^1$H-NMR (400 MHz, DMSO-$d_6$):<br>δ [ppm] = 0.68 (d, 3H), 0.80-0.88 (m, 6H), 1.68-1.81 (m, 1H), 2.35-2.48 (m, 1H), 2.61-2.70 (m, 1H), 2.70-2.81 (m, 1H), 3.36-3.49 (m, 1H), 3.87 (s, 3H), 4.10 (d, 1H), 7.01 (t, 2H), 7.23 (d, 1H), 7.32-7.37 (m, 2H), 7.43 (d, 1H), 9.81 (s, 1H), 11.96 (br. s, 1H). |
| 16 | 3-(4-chloro-3-{[(2S,3R)-4,4,4-trifluoro-3-methyl-2-(4-methylphenyl)butanoyl]amino}phenyl)-4-methylpentanoic acid (diastereomer 1)<br>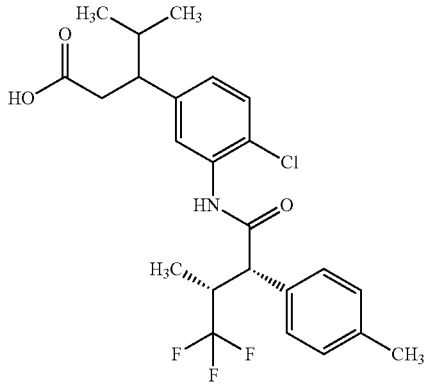<br>from methyl 3-(4-chloro-3-{[(2S,3R)-4,4,4-trifluoro-3-methyl-2-(4-methylphenyl)-butanoyl]amino}phenyl)-4-methylpentanoate (diastereomer 1) | LC-MS (Method 8):<br>$R_t$ = 2.70 min; m/z = 470/472 $(M + H)^+$.<br>$^1$H-NMR (400 MHz, DMSO-$d_6$):<br>δ [ppm] = 0.68 (d, 3H), 0.79 (d, 3H), 0.84 (d, 3H), 1.68-1.80 (m, 1H), 2.29 (s, 3H), 2.36-2.47 (m, 1H), 2.61-2.69 (m, 1H), 2.70-2.79 (m, 1H), 3.26-3.40 (m, 1H, partially obscured by H$_2$O signal), 4.05 (d, 1H), 6.98 (dd, 1H), 7.17 (d, 2H), 7.29-7.39 (m, 4H), 9.73 (s, 0.96H, major diasteromer), 9.87 (s, 0.04H, minor diastereomer), 11.95 (br. s, 1H) (92% de) |

| Example | Name/Structure/Starting material | Analytical data |
|---|---|---|
| 17 | 3-(4-chloro-3-{[(2S,3R)-2-(4-chloro-3-methyl-phenyl)-4,4,4-trifluoro-3-methylbutanoyl]amino}-phenyl)-4-methylpentanoic acid (diastereomer 1)<br>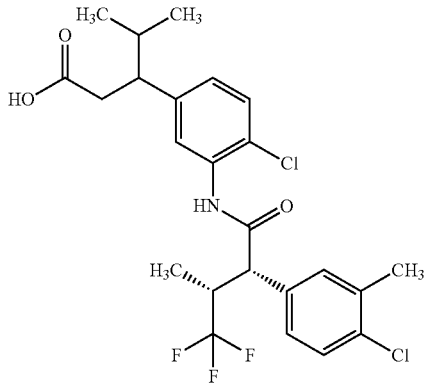<br>from methyl 3-(4-chloro-3-{[(2S,3R)-2-(4-chloro-3-methylphenyl)-4,4,4-trifluoro-3-methylbutanoyl]-amino}phenyl)-4-methylpentanoate (diastereomer 1) | LC-MS (Method 5):<br>$R_t$ = 1.33 min; m/z = 504/506 (M + H)+.<br>$^1$H-NMR (400 MHz, DMSO-$d_6$): δ [ppm] = 0.68 (d, 3H), 0.75-0.89 (m, 6H), 1.68-1.81 (m, 1H), 2.33 (s, 3H), 2.36-2.59 (m, 1H, partially obscured by DMSO signal), 2.61-2.70 (m, 1H), 2.70-2.81 (m, 1H), 3.25-3.43 (m, 1H, partially obscured by H$_2$O signal), 4.07 (d, 1H), 7.00 (d, 1H), 7.25-7.39 (m, 3H), 7.39-7.47 (m, 2H), 9.81 (s, 1H), 11.95 (br. s, 1H). |
| 18 | 3-(4-chloro-3-{[(4-chlorophenyl)(3,3-difluoro-cyclopentyl)acetyl]amino}phenyl)-4-methyl-pentanoic acid (isomer 1)<br>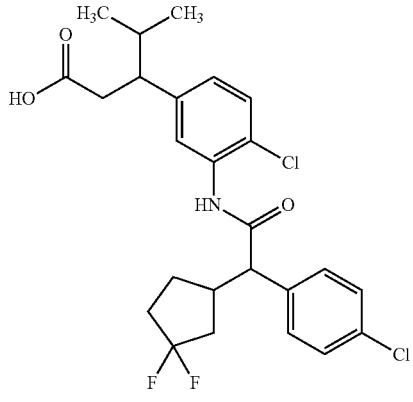<br>from methyl 3-(4-chloro-3-{[(4-chlorophenyl)-(3,3-difluorocyclopentyl)acetyl]amino}phenyl)-4-methylpentanoate (isomer 1) | LC-MS (Method 8):<br>$R_t$ = 2.71 min; m/z = 498/500 (M + H)+.<br>$^1$H-NMR (400 MHz, DMSO-$d_6$): δ [ppm] = 0.67 (d, 3H), 0.84 (d, 3H), 1.52-1.69 (m, 2H), 1.70-1.81 (m, 1H), 1.81-1.96 (m, 1H), 1.98-2.31 (m, 3H), 2.36-2.47 (m, 1H), 2.61-2.70 (m, 1H), 2.70-2.80 (m, 1H), 2.80-2.93 (m, 1H), 3.78 (d, 1H), 7.02 (dd, 1H), 7.31-7.39 (m, 2H), 7.44 (q, 4H), 9.78 (s, 1H), 11.95 (br. s, 1H). |

| Example | Name/Structure/Starting material | Analytical data |
| --- | --- | --- |
| 19 | 3-(4-chloro-3-{[(4-chlorophenyl)(3,3-difluoro-cyclopentyl)acetyl]amino}phenyl)-4-methyl-pentanoic acid (isomer 2)<br><br>from methyl 3-(4-chloro-3-{[(4-chlorophenyl)-(3,3-difluorocyclopentyl)acetyl]amino}phenyl)-4-methylpentanoate (isomer 2) | LC-MS (Method 8):<br>$R_t$ = 2.71 min; m/z = 498/500 (M + H)$^+$.<br>$^1$H-NMR (400 MHz, DMSO-$d_6$): δ [ppm] = 0.67 (d, 3H), 0.85 (d, 3H), 1.52-1.69 (m, 2H), 1.70-1.81 (m, 1H), 1.81-1.96 (m, 1H), 1.98-2.31 (m, 3H), 2.36-2.48 (m, 1H), 2.61-2.70 (m, 1H), 2.70-2.79 (m, 1H), 2.80-2.93 (m, 1H), 3.79 (d, 1H), 7.01 (dd, 1H), 7.32-7.39 (m, 2H), 7.43 (q, 4H), 9.77 (s, 1H), 11.95 (br. s, 1H). |
| 20 | 3-(4-chloro-3-{[(4-chlorophenyl)(3,3-difluoro-cyclopentyl)acetyl]amino}phenyl)-4-methyl-pentanoic acid (isomer 3)<br><br>from methyl 3-(4-chloro-3-{[(4-chlorophenyl)-(3,3-difluorocyclopentyl)acetyl]amino}phenyl)-4-methylpentanoate (isomer 3) | LC-MS (Method 8:<br>$R_t$ = 2.71 min; m/z = 498/500 (M + H)$^+$.<br>$^1$H-NMR (400 MHz, DMSO-$d_6$): δ [ppm] = 0.67 (d, 3H), 0.84 (d, 3H), 1.20-1.34 (m, 1H), 1.45-1.56 (m, 1H), 1.70-1.81 (m, 1H), 1.85-2.19 (m, 3H), 2.28-2.40 (m, 1H), 2.40-2.53 (m, 1H, partially obscured by DMSO signal), 2.61-2.70 (m, 1H), 2.70-2.90 (m, 2H), 3.75 (d, 1H), 7.02 (dd, 1H), 7.34 (d, 1H ), 7.37 (d, 1H), 7.44 (q, 4H), 9.74 (s, 1H), 11.95 (br. s, 1H). |

| Example | Name/Structure/Starting material | Analytical data |
|---|---|---|
| 21 | 3-(4-chloro-3-{[(4-chlorophenyl)(3,3-difluoro-cyclopentyl)acetyl]amino}phenyl)-4-methyl-pentanoic acid (isomer 4)<br>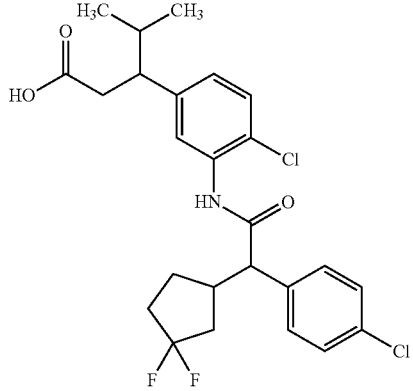<br>from methyl 3-(4-chloro-3-{[(4-chlorophenyl)-(3,3-difluorocyclopentyl)acetyl]amino}phenyl)-4-methylpentanoate (isomer 4) | LC-MS (Method 8):<br>$R_t$ = 2.71 min; m/z = 498/500 $(M + H)^+$.<br>$^1$H-NMR (400 MHz, DMSO-$d_6$):<br>δ [ppm] = 0.68 (d, 3H), 0.85 (d, 3H), 1.20-1.34 (m, 1H), 1.45-1.56 (m, 1H), 1.70-1.81 (m, 1H), 1.85-2.20 (m, 3H), 2.29-2.41 (m, 1H), 2.41-2.53 (m, 1H, partially obscured by DMSO signal), 2.62-2.70 (m, 1H), 2.70-2.90 (m, 2H), 3.75 (d, 1H), 7.02 (dd, 1H), 7.32-7.39 (m, 2H), 7.44 (q, 4H), 9.73 (s, 1H), 11.95 (br. s, 1H). |

Example 22

(+)-3-(4-Chloro-3-{[(2S,3R)-2-(4-chlorophenyl)-4,4,4-trifluoro-3-methylbutanoyl]amino}phenyl)-3-cyclopropylpropanoic acid (diastereomer 2)

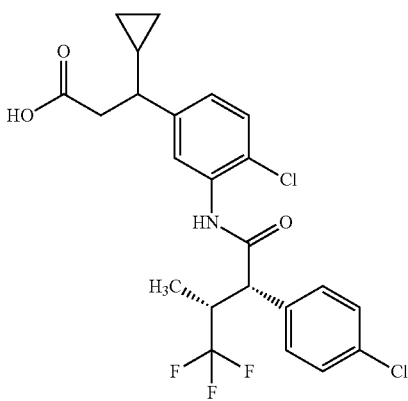 [SMILES: C[C@H]([C@H](C(=O)Nc1cc(C(CC(=O)O)C2CC2)ccc1Cl)c1ccc(Cl)cc1)C(F)(F)F]

78 mg (0.14 mmol) of tert-butyl 3-(4-chloro-3-{[(2S,3R)-2-(4-chlorophenyl)-4,4,4-trifluoro-3-methylbutanoyl]amino}phenyl)-3-cyclopropylpropanoate (diastereomer 2; Example 99A) were dissolved in 10 ml of dichloromethane, and 0.33 ml (4.3 mmol) of trifluoroacetic acid was added at RT. The reaction mixture was stirred at RT for 4 h and then diluted with 10 ml of water. The phases were separated, and the aqueous phase was then extracted three more times with dichloromethane. The combined organic phases were dried over magnesium sulphate and concentrated under reduced pressure. The crude product obtained in this manner was purified by preparative RP HPLC (mobile phase methanol/water 8:2 isocratic). This gave 56 mg of the target compound (81% of theory).

LC-MS (Method 5): $R_t$=1.20 min; m/z=488/490 $(M+H)^+$.

$^1$H-NMR (400 MHz, DMSO-$d_6$): δ [ppm]=0.02-0.10 (m, 1H), 0.19-0.33 (m, 2H), 0.44-0.53 (m, 1H), 0.80 (d, 3H), 0.89-0.99 (m, 1H), 2.20-2.29 (m, 1H), 2.47-2.68 (m, 2H, partially obscured by DMSO signal), 3.30-3.43 (m, 1H, partially obscured by H$_2$O signal), 4.13 (d, 1H), 7.10 (dd, 1H), 7.36 (d, 1H), 7.42 (d, 1H), 7.43-7.50 (m, 4H), 9.84 (s, 1H), 12.04 (br. s, 1H).

$[α]_D^{20}$=+98.8°, c=0.325, chloroform.

The compounds listed in the table below were prepared in an analogous manner:

| Example | Name/Structure/Starting material | Analytical data |
|---|---|---|
| 23 | (+)-3-(4-chloro-3-{[(2S,3R)-2-(4-chlorophenyl)-4,4,4-trifluoro-3-methylbutanoyl]amino}phenyl)-3-cyclopropylpropanoic acid (diastereomer 1)<br>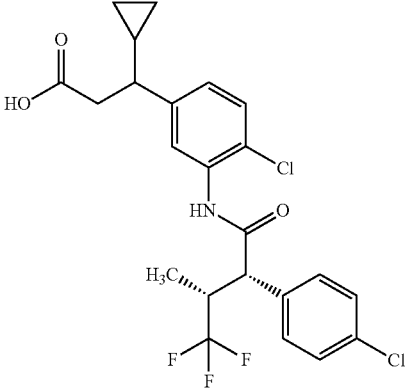<br>from tert-butyl 3-(4-chloro-3-{[(2S,3R)-2-(4-chlorophenyl)-4,4,4-trifluoro-3-methyl-butanoyl]amino}phenyl)-3-cyclopropylpropanoate (diastereomer 1) | LC-MS (Method 5):<br>$R_t$ = 1.20 min; m/z = 488/490 $(M + H)^+$.<br>$^1$H-NMR (400 MHz, DMSO-$d_6$):<br>δ [ppm] = 0.03-0.12 (m, 1H), 0.19-0.35 (m, 2H), 0.44-0.54 (m, 1H), 0.80 (d, 3H), 0.88-0.99 (m, 1H), 2.20-2.29 (m, 1H), 2.47-2.69 (m, 2H, partially obscured by DMSO signal), 3.29-3.43 (m, 1H, partially obscured by H$_2$O signal), 4.13 (d, 1H), 7.10 (dd, 1H), 7.36 (d, 1H), 7.41 (d, 1H), 7.43-7.50 (m, 4H), 9.84 (s, 1H), 12.03 (br. s, 1H).<br>$[α]_D^{20}$ = +57.3°, c = 0.355, chloroform. |
| 24 | 3-(4-chloro-3-{[(2S,3R)-2-(4-chlorophenyl)-4,4,4-trifluoro-3-methylbutanoyl]amino}phenyl)-3-cyclobutylpropanoic acid (diastereomer mixture)<br>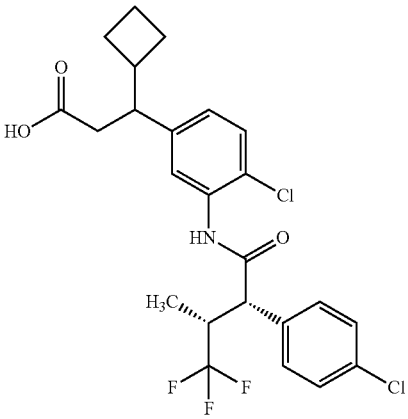<br>from tert-butyl 3-(4-chloro-3-{[(2S,3R)-2-(4-chlorophenyl)-4,4,4-trifluoro-3-methyl-butanoyl]amino}phenyl)-3-cyclobutylpropanoate (diastereomer mixture) | LC-MS (Method 5):<br>$R_t$ = 1.31 min; m/z = 502 $(M + H)^+$.<br>$^1$H-NMR (400 MHz, DMSO-$d_6$):<br>δ [ppm] = 0.80 (d, 3H), 1.44-1.62 (m, 2H), 1.62-1.75 (m, 3H), 1.97-2.02 (m, 1H), 2.29 (dd, 1H), 2.33-2.42 (m, 1H), 2.46 (dd, 1H), 2.87 (td, 1H), 3.36-3.42 (m, 1H), 4.13 (d, 1H), 7.01 (dd, 1H), 7.33 (d, 1H), 7.37 (t, 1H), 7.43-7.51 (m, 4H), 9.81 (s, 1H), 11.99 (br. s, ca. 1H). |

| Example | Name/Structure/Starting material | Analytical data |
|---|---|---|
| 25 | 3-(4-chloro-3-{[(2S,3R)-2-(4-chlorophenyl)-4,4,4-trifluoro-3-methylbutanoyl]amino}phenyl)-4-methoxy-4-methylpentanoic acid (diastereomer mixture)<br/>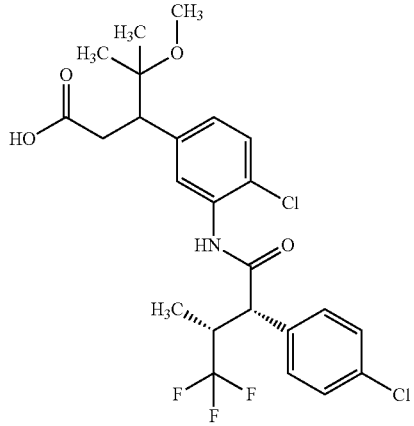<br/>from tert-butyl 3-(4-chloro-3-{[(2S,3R)-2-(4-chlorophenyl)-4,4,4-trifluoro-3-methylbutanoyl]amino}phenyl)-4-methoxy-4-methyl-pentanoate (diastereomer mixture) | LC-MS (Method 7):<br/>$R_t$ = 1.26 min; m/z = 520/522 (M + H)$^+$.<br/>$^1$H-NMR (400 MHz, DMSO-d$_6$):<br/>δ [ppm] = 0.80 (d, 3H), 0.94 (d, 3H), 1.00 (d, 3H), 1.33-1.40 (m, 1H), 2.70-2.78 (m, 1H), 3.10 (s, 3H), 3.11-3.18 (m, 1H), 3.32-3.44 (m, 1H, partially obscured by H$_2$O signal), 4.12 (d, 1H), 7.08 (dd, 1H), 7.33 (dd, 1H), 7.42 (d, 1H), 7.43-7.50 (m, 4H), 9.83 (d, 1H), 11.91 (br. s, ca. 1H). |
| 26 | 3-(4-chloro-3-{[(2S,3R)-2-(4-chlorophenyl)-4,4,4-trifluoro-3-methylbutanoyl]amino}phenyl)-3-(1-methylcyclopropyl)propanoic acid (diastereomer mixture)<br/>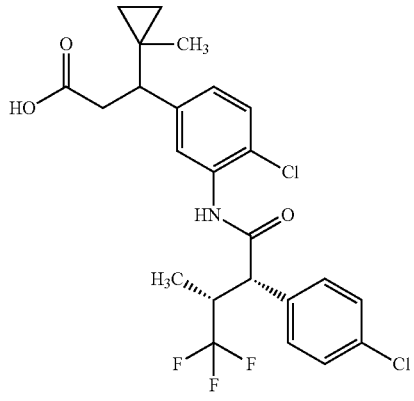<br/>from tert-butyl 3-(4-chloro-3-{[(2S,3R)-2-(4-chlorophenyl)-4,4,4-trifluoro-3-methyl-butanoyl]amino}phenyl)-3-(1-methylcyclopropyl)-propanoate (diastereomer mixture) | LC-MS (Method 5):<br/>$R_t$ = 1.27 min (diastereomer 1), m/z = 502/504 (M + H)$^+$;<br/>$R_t$ = 1.31 min (diastereomer 2), m/z = 502/504 (M + H)$^+$.<br/>$^1$H-NMR (400 MHz, DMSO-d$_6$):<br/>δ [ppm] = 0.80 (d, 3H), 0.88-0.96 (m, 5H), 1.66-1.78 (m, 2H), 2.76-2.85 (m, 1H), 3.05-3.17 (m, 1H), 3.30-3.45 (m, 1H, partially obscured by H$_2$O signal), 3.57-3.66 (m, 1H), 4.10-4.18 (m, 1H), 7.19 (dd, 1H), 7.40-7.51 (m, 6H), 9.92 (d, 1H). |

| Example | Name/Structure/Starting material | Analytical data |
|---|---|---|
| 27 | 3-(4-chloro-3-{[(2S,3R)-2-(4-chlorophenyl)-4,4,4-trifluoro-3-methylbutanoyl]amino}phenyl)-3-(1-fluorocyclopropyl)propanoic acid (diastereomer mixture)<br>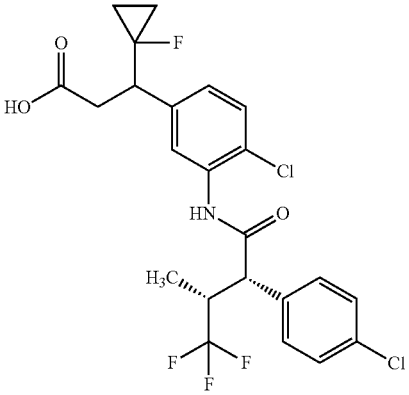<br>from tert-butyl 3-(4-chloro-3-{[(2S,3R)-2-(4-chlorophenyl)-4,4,4-trifluoro-3-methyl-butanoyl]amino}phenyl)-3-(1-fluorocyclopropyl)-propanoate (diastereomer mixture) | LC-MS (Method 5):<br>$R_t$ = 1.18 min; m/z = 506/508 $(M + H)^+$.<br>$^1$H-NMR (400 MHz, DMSO-$d_6$):<br>δ [ppm] = 0.65-0.90 (m, 2H), 0.80 (d, 3H), 0.90-1.08 (m, 1H), 1.11-1.31 (m, 1H), 1.56-1.73 (m, 1H), 2.69-2.89 (m, 2H), 3.30-3.44 (m, 1H, partially obscured by H$_2$O signal), 4.13 (d, 1H), 7.14 (dd, 1H), 7.39 (d, 1H), 7.42-7.52 (m, 5H), 9.87 (s, 1H), 11.85-12.70 (br. s, 1H). |
| 28 | 3-(4-chloro-3-{[(2S,3R)-2-(4-chlorophenyl)-4,4,4-trifluoro-3-methylbutanoyl]amino}phenyl)-3-(3,3-difluorocyclobutyl)propanoic acid (diastereomer mixture)<br>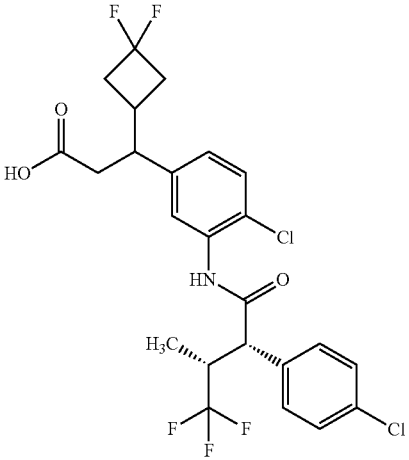<br>from tert-butyl 3-(4-chloro-3-{[(2S,3R)-2-(4-chlorophenyl)-4,4,4-trifluoro-3-methyl-butanoyl]amino}phenyl)-3-(3,3-difluoro-cyclobutyl)propanoate (diastereomer mixture) | LC-MS (Method 5):<br>$R_t$ = 1.24 min; m/z = 538/540 $(M + H)^+$.<br>$^1$H-NMR (400 MHz, DMSO-$d_6$):<br>δ [ppm] = 0.80 (d, 2.29H), 1.21-1.31 (m, 1.71H), 2.02-2.17 (m, 1H), 2.18-2.39 (m, 3H), 2.40-2.75 (m, 2H, partially obscured by DMSO signal), 2.91-3.03 (m, 1H), 3.17-3.44 (m, 1H, partially obscured by H$_2$O signal), 4.13 (d, 1H), 7.05-7.16 (m, 1H), 7.33-7.53 (m, 6H), 9.85 (s, 0.7H), 9.98 (s, 0.3H), 11.96-12.18 (br. s, 1H). |

| Example | Name/Structure/Starting material | Analytical data |
| --- | --- | --- |
| 29 | 3-(4-chloro-3-{[(2S,3R)-2-(4-chlorophenyl)-4,4,4-trifluoro-3-methylbutanoyl]amino}phenyl)-4-cyclopropylbutanoic acid (diastereomer mixture)<br>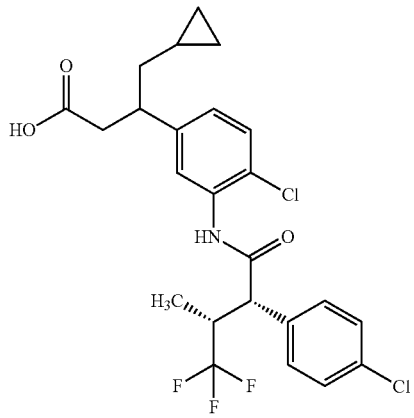<br>from tert-butyl 3-(4-chloro-3-{[(2S,3R)-2-(4-chlorophenyl)-4,4,4-trifluoro-3-methylbutanoyl]amino}phenyl)-4-cyclopropylbutanoate (diastereomer mixture) | LC-MS (Method 5):<br>$R_t$ = 1.29 min; m/z = 502/504 (M + H)$^+$. |

Example 30

3-(4-Chloro-3-{[(3R)-2-(4-chlorophenyl)-4,4,4-trifluoro-3-methylbutanoyl]amino}phenyl)-3-cyclopropyl-2-methylpropanoic acid (Diastereomer Mixture)

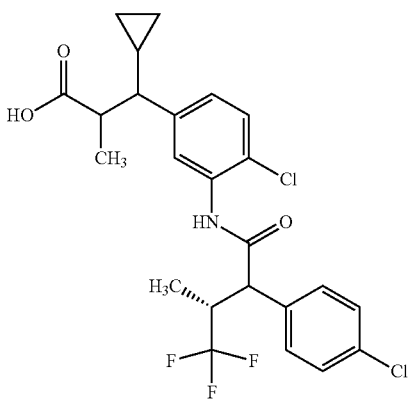 [SMILES: CC(C(=O)O)C(c1ccc(Cl)c(NC(=O)C(c2ccc(Cl)cc2)[C@@H](C)C(F)(F)F)c1)C1CC1]

250 mg (0.47 mmol) of ethyl 3-(4-chloro-3-{[(2S,3R)-2-(4-chlorophenyl)-4,4,4-trifluoro-3-methylbutanoyl]amino}phenyl)-3-cyclopropyl-2-methylpropanoate (diastereomer mixture; Example 129A) were dissolved in a mixture of 1.0 ml of methanol, 0.5 ml of THF and 0.5 ml of water, and 40 mg (0.94 mmol) of lithium hydroxide monohydrate were added at 0° C. The mixture was stirred initially at 0° C. for 1 h and then at RT overnight. Another 40 mg (0.94 mmol) of lithium hydroxide monohydrate were then added, and the reaction solution was warmed to 50° C. After further stirring at this temperature overnight, 1 ml of methanol was metered into the reaction mixture, and the mixture was stirred at 60° C. for a further 12 h. The solution was then diluted with water and acidified with 1 N hydrochloric acid (pH about 2). The aqueous phase was extracted three times with ethyl acetate. The combined organic phases were dried over magnesium sulphate and concentrated under reduced pressure. This gave 204 mg (86% of theory) of the title compound as a diastereomer mixture.

LC-MS (Method 7): $R_t$=1.26 min, m/z=502/504 (M+H)$^+$ (diastereomer 1); $R_t$=1.27 min, m/z=502/504 (M+H)$^+$ (diastereomer 2); $R_t$=1.28 min, m/z=502/504 (M+H)$^+$ (diastereomer 3); $R_t$=1.30 min, m/z=502/504 (M+H)$^+$ (diastereomer 4).

$^1$H-NMR (400 MHz, DMSO-d$_6$): δ [ppm]=−0.20-0.05 (m, 0.85H), 0.13-0.36 (m, 2H), 0.47-0.65 (m, 0.85H), 0.68-0.75 (m, 0.3H), 0.80 (d, 2.63H), 0.93-1.09 (m, 1H), 1.17 (d, 1.5H), 1.21-1.29 (m, 1.87H), 1.84-2.08 (m, 1H), 2.61-2.77 (m, 1H), 3.16-3.27 (m, 0.5H), 3.28-3.43 (m, 0.5H, partially obscured by H₂O signal), 4.09-4.17 (m, 1H), 6.70-6.78 (m, 0.16H), 7.02-7.13 (m, 1H), 7.30-7.53 (m, 5.84H), 9.80-10.01 (m, 1H), 11.79-12.35 (br. m, 1H).

Example 31

3-(4-Chloro-3-{[(3R)-2-(4-chlorophenyl)-4,4,4-trifluoro-3-methylbutanoyl]amino}phenyl)-3-(2,2-difluorocyclopropyl)propanoic acid (Diastereomer Mixture 1)

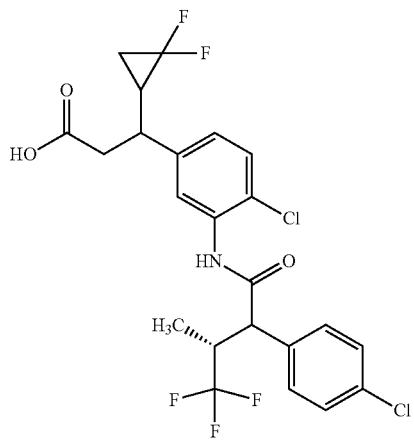 [SMILES: C[C@H](C(C(=O)Nc1cc(C(CC(=O)O)C2CC2(F)F)ccc1Cl)c1ccc(Cl)cc1)C(F)(F)F]

114 mg (0.21 mmol) of methyl 3-(4-chloro-3-{[(2S,3R)-2-(4-chlorophenyl)-4,4,4-trifluoro-3-methylbutanoyl]amino}phenyl)-3-(2,2-difluorocyclopropyl)propanoate (isomer 1; Example 124A) were dissolved in a mixture of 2 ml of dioxane and 1 ml of water, and 27 mg (0.64 mmol) of lithium hydroxide monohydrate were added. The mixture was stirred at RT overnight. The solution was then diluted with water and acidified with 1 N hydrochloric acid (pH about 2). The precipitated solid was filtered off with suction and dried under high vacuum overnight. This gave 89 mg (80% of theory) of the title compound as a diastereomer mixture in the form of a white solid.

LC-MS (Method 5): R*t*=1.26 min; m/z=524/526 (M+H)⁺.

¹H-NMR (400 MHz, DMSO-d₆): δ [ppm]=0.80 (d, 1.63H), 1.04-1.19 (m, 1H), 1.26 (d, 1.37H), 1.36-1.50 (m, 1H), 1.97-2.14 (m, 1H), 2.46-2.82 (m, 3H, partially obscured by DMSO signal), 3.15-3.43 (m, 1H, partially obscured by H₂O signal), 4.07-4.17 (m, 1H), 7.17-7.26 (m, 1H), 7.36-7.53 (m, 6H), 9.87 (s, 0.55H), 10.01 (s, 0.45H), 12.16 (br. s, 1H).

Example 32

3-(4-Chloro-3-{[(3R)-2-(4-chlorophenyl)-4,4,4-trifluoro-3-methylbutanoyl]amino}phenyl)-3-(2,2-difluorocyclopropyl)propanoic acid (Diastereomer Mixture 2)

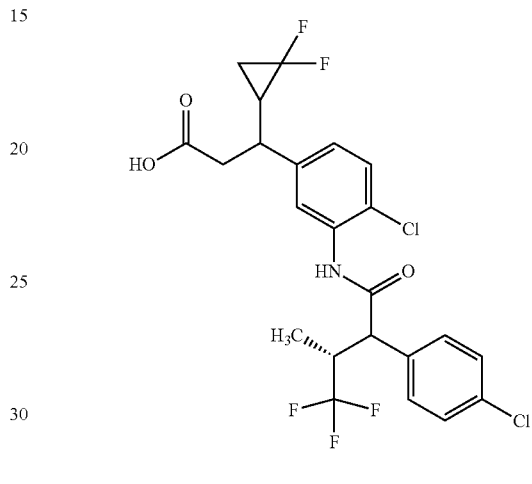

115 mg (0.21 mmol) of methyl 3-(4-chloro-3-{[(2S,3R)-2-(4-chlorophenyl)-4,4,4-trifluoro-3-methylbutanoyl]amino}phenyl)-3-(2,2-difluorocyclopropyl)propanoate (isomer 2; Example 125A) were dissolved in a mixture of 2 ml of dioxane and 1 ml of water, and 27 mg (0.64 mmol) of lithium hydroxide monohydrate were added. The mixture was stirred at RT overnight. The solution was then diluted with water and acidified with 1 N hydrochloric acid (pH about 2). The aqueous phase was extracted three times with dichloromethane. The combined organic phases were dried over magnesium sulphate and concentrated under reduced pressure. This gave 101 mg (90% of theory) of the title compound as a diastereomer mixture in the form of a colourless oil.

LC-MS (Method 5): R*t*=1.26 min; m/z=524/526 (M+H)⁺.

¹H-NMR (400 MHz, DMSO-d₆): δ [ppm]=0.80 (d, 1.68H), 1.05-1.18 (m, 1H), 1.26 (d, 1.32H), 1.35-1.50 (m, 1H), 1.96-2.12 (m, 1H), 2.44-2.82 (m, 3H, partially obscured by DMSO signal), 3.15-3.42 (m, 1H, partially obscured by H₂O signal), 4.08-4.16 (m, 1H), 7.17-7.25 (m, 1H), 7.37-7.52 (m, 6H), 9.87 (s, 0.56H), 10.01 (s, 0.44H), 12.16 (br. s, 1H).

Example 33 and Example 34

(+)-3-(4-Chloro-3-{[(2S,3R)-2-(4-chlorophenyl)-4,4,4-trifluoro-3-methylbutanoyl]amino}phenyl)-3-cyclobutylpropanoic acid (Diastereomers 1 and 2)

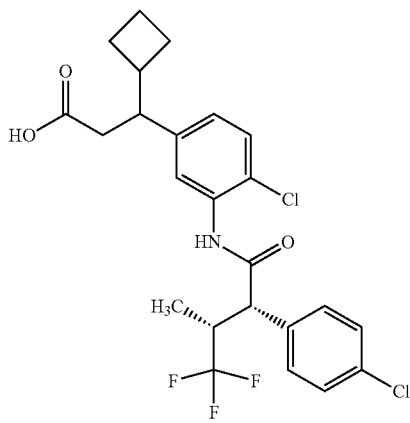 [SMILES: C[C@H]([C@H](C(=O)Nc1cc(C(CC(=O)O)C2CCC2)ccc1Cl)c1ccc(Cl)cc1)C(F)(F)F]

The diastereomer mixture obtained above of 3-(4-chloro-3-{[(2S,3R)-2-(4-chlorophenyl)-4,4,4-tri-fluoro-3-methylbutanoyl]amino}phenyl)-3-cyclobutylpropanoic acid (Example 24) was separated further by preparative HPLC on a chiral phase [column: Daicel Chiralpak AD-H, 5 μm, 250 mm×20 mm; injection volume: 0.40 ml; mobile phase: 90% isohexane/10% isopropanol; flow rate: 15 ml/min; detection: 220 nm; temperature: 25° C.]. 63 mg of diastereomer mixture gave 29 mg of diastereomer 1 (Example 33) and 32 mg of diastereomer 2 (Example 34).

Example 33 (Diastereomer 1):

LC-MS (Method 5): $R_t$=1.31 min; m/z=502 (M+H)$^+$.

$^1$H-NMR (400 MHz, DMSO-d$_6$): δ [ppm]=0.80 (d, 3H), 1.45-1.62 (m, 2H), 1.62-1.79 (m, 3H), 1.97-2.03 (m, 1H), 2.24-2.39 (m, 2H), 2.42-2.47 (m, 1H), 2.87 (td, 1H), 3.35-3.40 (m, 1H), 4.13 (d, 1H), 7.01 (dd, 1H), 7.23-7.39 (m, 2H), 7.42-7.54 (m, 4H), 9.81 (s, 1H), 11.98 (br. s, 1H).

$[α]_D^{20}$=+69°, c=0.260, chloroform.

Example 34 (Diastereomer 2):

LC-MS (Method 5): $R_t$=1.31 min; m/z=502 (M+H)$^+$.

$^1$H-NMR (400 MHz, DMSO-d$_6$): δ [ppm]=0.80 (d, 3H), 1.45-1.63 (m, 2H), 1.63-1.76 (m, 3H), 1.98-2.04 (m, 1H), 2.22-2.42 (m, 2H), 2.44-2.48 (m, 1H), 2.87 (td, 1H), 4.13 (d, 1H), 7.02 (dd, 1H), 7.33 (d, 1H), 7.37 (d, 1H), 7.42-7.51 (m, 4H), 9.81 (s, 1H), 12.00 (br. s, 1H).

$[α]_D^{20}$=+53°, c=0.250, chloroform.

Example 35 and Example 36

3-(4-Chloro-3-{[(2S,3R)-2-(4-chlorophenyl)-4,4,4-trifluoro-3-methylbutanoyl]amino}phenyl)-4-cyclopropylbutanoic acid (Diastereomers 1 and 2)

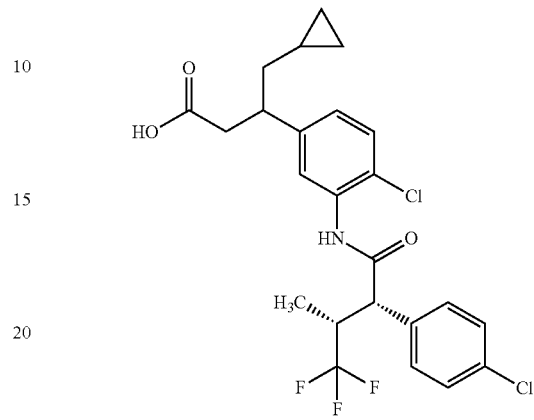

55 mg (0.11 mmol) of the diastereomer mixture of 3-(4-chloro-3-{[(2S,3R)-2-(4-chlorophenyl)-4,4,4-trifluoro-3-methylbutanoyl]amino}phenyl)-4-cyclopropylbutanoic acid (Example 29) were separated further by preparative HPLC on a chiral phase [column: Daicel Chiralpak AD-H, 5 μm, 250 mm×20 mm; mobile phase: isohexane/ethanol 90:10 (v/v); flow rate: 15 ml/min; UV detection: 220 nm; temperature: 30° C.]:

Example 35 (Diastereomer 1):

Yield: 28 mg $R_t$=7.47 min; chemical purity >99%; >99% de

[Column: Chiralpak AD-H, 5 μm, 250 mm×4.6 mm; mobile phase: isohexane/(ethanol+0.2% trifluoroacetic acid+1% water) 90:10 (v/v); flow rate: 1 ml/min; UV detection: 220 nm; temperature: 30° C.].

LC-MS (Method 5): $R_t$=1.26 min; m/z=502/504 (M+H)$^+$.

$^1$H-NMR (400 MHz, DMSO-d$_6$): δ [ppm]=−0.14-0.06 (m, 1H), −0.06-0.03 (m, 1H), 0.22-0.37 (m, 2H), 0.39-0.50 (m, 1H), 0.80 (d, 3H), 1.27-1.36 (m, 1H), 1.45-1.56 (m, 1H), 2.39-2.47 (m, 1H), 2.57-2.66 (m, 1H), 2.99-3.09 (m, 1H), 3.28-3.43 (m, 1H, partially obscured by H$_2$O signal), 4.13 (d, 1H), 7.07 (dd, 1H), 7.35 (d, 1H), 7.41 (d, 1H), 7.43-7.50 (m, 1H), 9.82 (s, 1H), 12.02 (br. s, 1H).

$[α]_D^{20}$=+41°, c=0.260, chloroform.

Example 36 (Diastereomer 2):

Yield: 25 mg $R_t$=8.75 min; chemical purity >99%; >98.7% de

[Column: Chiralpak AD-H, 5 μm, 250 mm×4.6 mm; mobile phase: isohexane/(ethanol+0.2% trifluoroacetic acid+1% water) 90:10 (v/v); flow rate: 1 ml/min; UV detection: 220 nm; temperature: 30° C.].

LC-MS (Method 5): $R_t$=1.26 min; m/z=502/504 (M+H)$^+$.

$^1$H-NMR (400 MHz, DMSO-d$_6$): δ [ppm]=−0.14-0.07 (m, 1H), −0.06-0.02 (m, 1H), 0.22-0.36 (m, 2H), 0.38-0.49 (m, 1H), 0.80 (d, 3H), 1.27-1.36 (m, 1H), 1.46-1.55 (m, 1H), 2.39-2.47 (m, 1H), 2.58-2.66 (m, 1H), 2.99-3.09 (m, 1H), 3.28-3.43 (m, 1H, partially obscured by H$_2$O signal), 4.13 (d, 1H), 7.07 (dd, 1H), 7.35 (d, 1H), 7.42 (d, 1H), 7.43-7.50 (m, 4H), 9.82 (s, 1H), 12.02 (br. s, 1H).

The following compound was prepared analogously to Example 22:

| Example | Name/Structure/Starting material | Analytical data |
|---|---|---|
| 37 | 3-(4-chloro-3-{[(2S,3R)-2-(4-chlorophenyl)-4,4,4-trifluoro-3-methylbutanoyl]amino}phenyl)-4-(1-methylcyclopropyl)butanoic acid (diastereomer mixture)<br>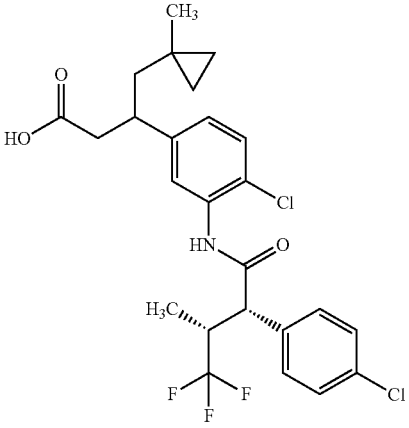<br>from tert-butyl 3-(4-chloro-3-{[(2S,3R)-2-(4-chlorophenyl)-4,4,4-trifluoro-3-methylbutanoyl]amino}phenyl)-4-(1-methylcyclopropyl)butanoate (diastereomer mixture) | LC-MS (Method 7): $R_t$ = 1.34 min; m/z = 516/518 $(M + H)^+$.<br>$^1$H-NMR (400 MHz, DMSO-$d_6$): δ [ppm] = −0.160−−0.09 (m, 1H), −0.09−−0.02 (m, 1H), 0.11-0.18 (m, 1H), 0.18-0.25 (m, 1H), 0.80 (d, 3H), 0.92 (d, 3H), 1.47-1.55 (m, 2H), 2.31-2.42 (m, 1H), 2.57-2.65 (m, 1H), 3.05-3.20 (m, 1H), 3.28-3.43 (m, 1H, partially obscured by H$_2$O signal), 4.12 (d, 1H), 7.01-7.13 (m, 1H), 7.33 (d, 1H), 7.39-7.51 (m, 5H), 9.81 (d, 1H), 12.03 (br. s, 1H). |

B. Assessment of the Pharmacological Activity

The pharmacological effect of the compounds according to the invention can be shown in the following assays:

B-1. Stimulation of Recombinant Soluble Guanylate Cyclase (sGC) In Vitro

Investigations on the stimulation of recombinant soluble guanylate cyclase (sGC) by the compounds according to the invention with and without sodium nitroprusside, and with and without the haem-dependent sGC inhibitor 1H-1,2,4-oxadiazolo[4,3a]quinoxalin-1-one (ODQ), are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The haem-free guanylate cyclase is obtained by adding Tween 20 to the sample buffer (0.5% in the final concentration).

The activation of sGC by a test substance is reported as x-fold stimulation of the basal activity. The result for Example 22 is shown in Table 1:

TABLE 1

Stimulation (x-fold) of recombinant soluble guanylate cyclase (sGC) in vitro by Example 22

| Concentration | Haem-containing sGC | | | Haem-free |
|---|---|---|---|---|
| Example 22 [μM] | Basal (n = 5) | +0.01 μM DEA/NO | +10 μM ODQ | sGC Basal (n = 5) |
| 0 | 1.0 ± 0.0 | 3.6 ± 1.0 | 5.1 ± 1.5 | 1.0 ± 0.0 |
| 0.01 | 1.6 ± 0.3 | 4.4 ± 1.3 | 5.7 ± 1.6 | 1.2 ± 0.1 |
| 0.1 | 1.6 ± 0.5 | 3.4 ± 0.9 | 6.1 ± 1.7 | 1.6 ± 0.5 |

TABLE 1-continued

Stimulation (x-fold) of recombinant soluble guanylate cyclase (sGC) in vitro by Example 22

| Concentration | Haem-containing sGC | | | Haem-free |
|---|---|---|---|---|
| Example 22 [μM] | Basal (n = 5) | +0.01 μM DEA/NO | +10 μM ODQ | sGC Basal (n = 5) |
| 1.0 | 2.4 ± 1.0 | 4.4 ± 1.4 | 8.4 ± 2.2 | 4.9 ± 1.5 |
| 10 | 4.9 ± 1.2 | 7.8 ± 2.5 | 18.3 ± 5.4 | 14.2 ± 2.0 |

[DEA/NO = 2-(N,N-diethylamino)diazenolate 2-oxide; ODQ = 1H-1,2,4-oxadiazolo-[4,3a]quinoxalin-1-one].

It is evident from Table 1 that stimulation both of the haem-containing and of the haem-free enzyme is achieved. Furthermore, combination of Example 22 and 2-(N,N-diethylamino)-diazenolate 2-oxide (DEA/NO), an NO donor, shows no synergistic effect, i.e. the effect of DEA/NO is not potentiated as would be expected with an sGC activator acting via a haem-dependent mechanism. In addition, the effect of the sGC activator according to the invention is not blocked by 1H-1,2,4-oxadiazolo[4,3a]quinoxalin-1-one (ODQ), a haem-dependent inhibitor of soluble guanylate cyclase, but is in fact increased. The results in Table 1 thus confirm the mechanism of action of the compounds according to the invention as activators of soluble guanylate cyclase.

B-2. Action at a Recombinant Guanylate Cyclase Reporter Cell Line

The cellular action of the compounds according to the invention is determined at a recombinant guanylate cyclase reporter cell line, as described in F. Wunder et al., *Anal. Biochem.* 339, 104-112 (2005).

Representative results for the compounds according to the invention are listed in Table 2:

TABLE 2 sGC-activating activity in the CHO reporter cell in vitro

| Example No. | MEC [nM] |
|---|---|
| 1 | 3 |
| 2 | 6.5 |
| 3 | 0.3 |
| 4 | 3 |
| 5 | 0.3 |
| 6 | 1 |
| 7 | 300 |
| 8 | 1 |
| 9 | 1 |
| 10 | 0.3 |
| 11 | 3 |
| 12 | 1 |
| 13 | 0.3 |
| 14 | 0.3 |
| 15 | 3 |
| 16 | 3 |
| 17 | 1 |
| 18 | 300 |
| 19 | 30 |
| 20 | 1000 |
| 21 | 10 |
| 22 | 1.8 |
| 23 | 3 |
| 25 | 10 |
| 26 | 10 |
| 27 | 3 |
| 28 | 30 |
| 30 | 10 |
| 31 | 3 |
| 32 | 3 |
| 33 | 1 |
| 34 | 10 |
| 35 | 0.3 |
| 36 | 3 |

(MEC = minimum effective concentration).

B-3. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 µl of enzyme solution [0-10 nM soluble guanylate cyclase (prepared according to Hönicka et al., *J. Mol. Med.* 77, 14-23 (1999)) in 50 mM TEA, 2 mM MgCl$_2$, 0.1% BSA (fraction V), 0.005% Brij®, pH 7.5] are initially introduced into a microplate, and 1 µl of the substance to be tested (as a serially diluted solution in DMSO) is added. The mixture is incubated at room temperature for 10 min. Then 20 µl of detection mix [1.2 nM Firefly Luciferase (Photinus pyralis luciferase, Promega), 29 µM dehydroluciferin (prepared according to Bitler & McElroy, *Arch. Biochem. Biophys.* 72, 358 (1957)), 122 µM luciferin (Promega), 153 µM ATP (Sigma) and 0.4 mM DTT (Sigma) in 50 mM TEA, 2 mM MgCl$_2$, 0.1% BSA (fraction V), 0.005% Brij®, pH 7.5] are added. The enzyme reaction is started by adding 20 µl of substrate solution [1.25 mM guanosine 5'-triphosphate (Sigma) in 50 mM TEA, 2 mM MgCl$_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of haem-free guanylate cyclase is examined by addition of 25 µM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 3:

TABLE 3

Activating action at the sGC enzyme in vitro

| Example No. | MEC [nM] | EC$_{50}$ [nM] |
|---|---|---|
| 1 | 1 | 22 |
| 2 | 4 | 89 |
| 3 | 1 | 37 |
| 4 | 2.4 | 110 |
| 5 | 0.3 | 5.2 |
| 6 | 1.1 | 56 |
| 10 | 0.5 | 10 |
| 12 | 1.1 | 17 |
| 13 | 0.5 | 14 |
| 14 | 0.5 | 8.4 |
| 22 | 2.4 | 68 |
| 25 | 5.1 | 220 |
| 27 | 1.7 | 68 |
| 30 | 17 | 640 |
| 33 | 0.4 | 11 |
| 35 | 1 | 11 |

(MEC = minimum effective concentration; EC$_{50}$ = concentration at 50% of maximum efficacy).

B-4. Vasorelaxant Effect In Vitro

Rabbits are anaesthetized and sacrificed by intravenous injection of thiopental sodium (about 50 mg/kg) and exsanguinated. The saphenous artery is removed and divided into rings 3 mm wide.

The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; CaCl$_2$×2 H$_2$O 1 mM; MgSO$_4$×7 H$_2$O 1.4 mM; KH$_2$PO$_4$ 1.2 mM; NaHCO$_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the level of the contraction achieved under the influence of the test substance is compared with the level of the contraction reached in the last preceding run. The concentration necessary to reduce the contraction reached in the preceding control by 50% is calculated from this (IC$_{50}$). The standard application volume is 5 µl. The proportion of DMSO in the bath solution corresponds to 0.1%.

Representative results for the compounds according to the invention are listed in Table 4:

TABLE 4

Vasorelaxant effect in vitro

| Example No. | IC$_{50}$ [nM] |
|---|---|
| 3 | 801 |
| 10 | 131 |
| 14 | 269 |

TABLE 4-continued

Vasorelaxant effect in vitro

| Example No. | IC$_{50}$ [nM] |
|---|---|
| 16 | 767 |
| 22 | 137 |

B-5. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitters, (2) receivers, which are linked via a multiplexer to a (3) data acquisition computer. The telemetry system makes it possible to continuously record the blood pressure and heart rate of conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 μm.

The telemetry transmitters (TAM PA-C40, DSI) employed are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and layered closure of the wound is performed. An antibiotic (Tardomyocel COMP, Bayer AG, 1 ml/kg s.c.) is administered postoperatively for prophylaxis of infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A. R. T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measured values is repeated under computer control at 5-minute intervals. The source data obtained as absolute value are corrected in the diagram with the currently measured barometric pressure and stored as individual data. Further technical details are given in the documentation from the manufacturing company (DSI).

The test substances are administered at 9.00 am on the day of the experiment. Following the administration, the parameters described above are measured over 24 hours. After the end of the experiment, the acquired individual data are sorted using the analysis software (Dataquest™ A. R. T. Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average, 30-minute average) and transferred as a text file to a storage medium. The measured values presorted and compressed in this way are transferred into Excel templates and tabulated.

C. Exemplary Embodiments of Pharmaceutical Compositions

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound having a formula selected from the group consisting of:

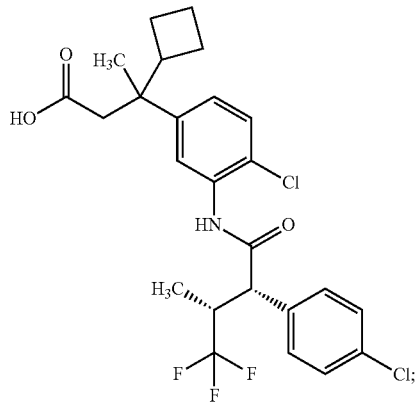

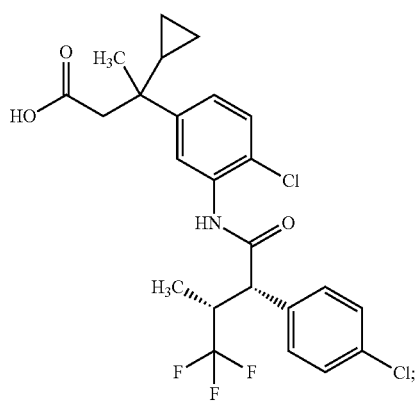

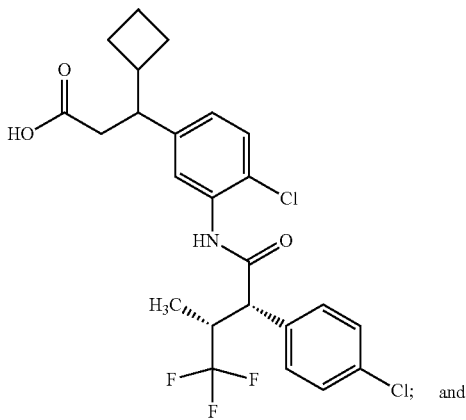

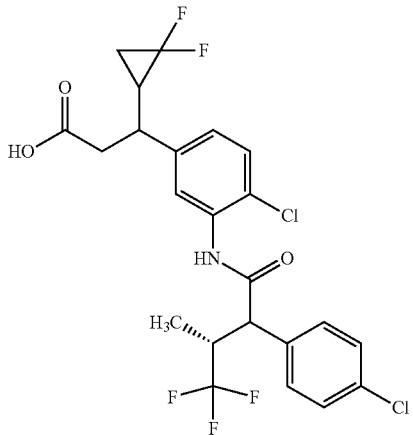 [SMILES: C[C@H](C(C(=O)Nc1cc(C(CC(=O)O)C2CC2(F)F)ccc1Cl)c1ccc(Cl)cc1)C(F)(F)F]

and hydrolysable ester derivatives thereof.

2. The compound of claim 1 having the formula

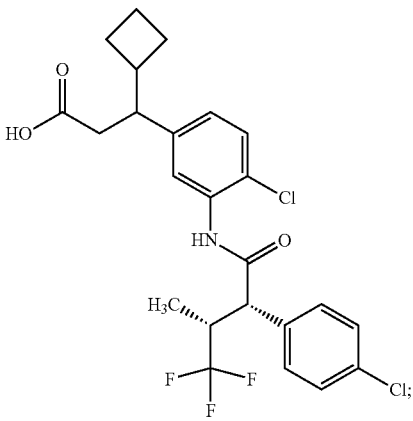 [SMILES: C[C@H]([C@H](C(=O)Nc1cc(C(CC(=O)O)C2CCC2)ccc1Cl)c1ccc(Cl)cc1)C(F)(F)F]

and hydrolysable ester derivatives thereof.

3. The compound of claim 1 having the formula and hydrolysable ester derivatives thereof.

4. The hydrolysable ester derivative of the compound as defined in claim 1.

5. A medicament comprising the compound as defined in claim 1 in combination with one or more inert, non-toxic, pharmaceutically suitable excipients.

6. A medicament comprising the compound as defined in claim 1 in combination with one or more further active compounds selected from the group consisting of organic nitrates, NO donors, cGMP-PDE inhibitors, stimulators of guanylate cyclase, agents having antithrombotic activity, agents lowering blood pressure, and agents altering lipid metabolisms.

* * * * *